US008067187B2

(12) United States Patent
Gebbink et al.

(10) Patent No.: US 8,067,187 B2
(45) Date of Patent: Nov. 29, 2011

(54) CROSS-β STRUCTURE BINDING COMPOUNDS

(75) Inventors: Martijn Frans Ben Gerard Gebbink, Eemnes (NL); Barend Bouma, Houten (NL)

(73) Assignee: Crossbeta Biosciences B.V., Utrecht (NL)

( * ) Notice: Subject to any disclaimer, the term of this patent is extended or adjusted under 35 U.S.C. 154(b) by 611 days.

(21) Appl. No.: 11/995,497

(22) PCT Filed: Jul. 13, 2006

(86) PCT No.: PCT/NL2006/000364
§ 371 (c)(1),
(2), (4) Date: Mar. 19, 2008

(87) PCT Pub. No.: WO2007/008072
PCT Pub. Date: Jan. 18, 2007

(65) Prior Publication Data
US 2008/0267948 A1  Oct. 30, 2008

(30) Foreign Application Priority Data
Jul. 13, 2005 (EP) .................... 05076613

(51) Int. Cl.
G01N 33/53 (2006.01)
G01N 31/00 (2006.01)
(52) U.S. Cl. ........ 435/7.21; 435/7.1; 436/501; 436/518; 530/300; 530/350; 424/94.64
(58) Field of Classification Search ........................ None
See application file for complete search history.

(56) References Cited

U.S. PATENT DOCUMENTS

| | | | |
|---|---|---|---|
| 5,051,185 A | 9/1991 | Watanabe et al. |
| 5,151,082 A | 9/1992 | Gorsuch et al. |
| 5,180,615 A | 1/1993 | Havens |
| 5,216,127 A | 6/1993 | Hirai et al. |
| 5,221,628 A | 6/1993 | Anderson et al. |
| 5,230,996 A | 7/1993 | Rath et al. |
| 5,276,059 A | 1/1994 | Caughey et al. |
| 5,278,189 A | 1/1994 | Rath et al. |
| 5,288,490 A | 2/1994 | Budzynski et al. |
| 5,449,663 A | 9/1995 | Bicher |
| 5,491,129 A | 2/1996 | Shaltiel |
| 5,589,154 A | 12/1996 | Anderson |
| 5,591,431 A | 1/1997 | Schasteen et al. |
| 5,599,678 A | 2/1997 | Kraus et al. |
| 5,624,908 A | 4/1997 | Bicher |
| 5,650,418 A | 7/1997 | Rath et al. |
| 5,700,447 A | 12/1997 | Bucala et al. |
| 5,731,007 A | 3/1998 | Chung et al. |
| 5,733,524 A | 3/1998 | Bucala et al. |
| 5,733,933 A | 3/1998 | Bucala et al. |
| 5,750,349 A | 5/1998 | Suzuki |
| 5,780,587 A | 7/1998 | Potter |
| 5,780,615 A | 7/1998 | Bucala et al. |
| 5,785,187 A | 7/1998 | Lipman et al. |
| 5,786,324 A | 7/1998 | Gray et al. |
| 5,801,200 A | 9/1998 | Bucala et al. |
| 5,817,626 A | 10/1998 | Findeis et al. |
| 5,834,028 A | 11/1998 | Kunihiro et al. |
| 5,851,996 A | 12/1998 | Kline |
| 5,854,215 A | 12/1998 | Findeis et al. |
| 5,869,534 A | 2/1999 | Bucala et al. |
| 5,935,927 A | 8/1999 | Vitek et al. |
| 5,948,763 A | 9/1999 | Soto-Jara et al. |
| 5,955,343 A | 9/1999 | Holmes et al. |
| 5,958,883 A | 9/1999 | Snow |
| 5,981,697 A | 11/1999 | Kraus et al. |
| 5,985,242 A | 11/1999 | Findeis et al. |
| 5,985,607 A | 11/1999 | Delcuve et al. |
| 6,001,331 A | 12/1999 | Caprathe et al. |
| 6,034,211 A | 3/2000 | Kelly |
| 6,037,327 A | 3/2000 | Castillo et al. |
| 6,037,458 A | 3/2000 | Hirai et al. |
| 6,136,548 A | 10/2000 | Anderson |
| 6,161,547 A | 12/2000 | Barbut |
| 6,184,030 B1 | 2/2001 | Katoot et al. |
| 6,242,473 B1 | 6/2001 | Hellstrand et al. |
| 6,310,046 B1 | 10/2001 | Duffy et al. |
| 6,319,498 B1 | 11/2001 | Findeis et al. |
| 6,340,783 B1 | 1/2002 | Snow |
| 6,372,473 B1 | 4/2002 | Moore et al. |
| 6,399,314 B1 | 6/2002 | Krishnamurthy |
| 6,410,598 B1 | 6/2002 | Vitek et al. |
| 6,436,969 B1 | 8/2002 | Khalifah et al. |
| 6,462,171 B1 | 10/2002 | Soto-Jara et al. |
| 6,471,960 B1 | 10/2002 | Anderson |
| 6,537,969 B1 | 3/2003 | Blass |
| 6,641,815 B2 | 11/2003 | Duffy et al. |
| 6,686,144 B2 | 2/2004 | McLeod et al. |
| 6,689,275 B1 | 2/2004 | Gupta |
| 6,960,465 B1 | 11/2005 | Papoutsakis et al. |
| 7,041,287 B2 | 5/2006 | Muzykantov et al. |
| 7,135,181 B2 | 11/2006 | Jensen et al. |
| 7,172,875 B2 | 2/2007 | Kuret et al. |
| 7,196,064 B2 | 3/2007 | McAnalley et al. |

(Continued)

FOREIGN PATENT DOCUMENTS

AU   2003214375 B2   10/2003
(Continued)

OTHER PUBLICATIONS

Bouma Barend et al. (Journal of Biological Chemistry, American society of biochemical biologist, vol. 278, No. 43, Oct. 24, 2001, pp. 41810-41819).*

(Continued)

*Primary Examiner* — Lisa Cook
(74) *Attorney, Agent, or Firm* — TraskBritt

(57) ABSTRACT

The invention relates to the field of biochemistry, biophysical chemistry, molecular biology, structural biology and medicine. More in particular, the invention relates to cross-β structure conformation. Even more particular, the invention relates to compounds capable of binding to a compound with cross-β structure conformation, i.e., cross-β structure binding compounds and uses thereof.

8 Claims, 30 Drawing Sheets

U.S. PATENT DOCUMENTS

| | | | |
|---|---|---|---|
| 7,517,525 | B2 | 4/2009 | Prenner et al. |
| 2002/0065327 | A1 | 5/2002 | Jiao et al. |
| 2002/0114796 | A1 | 8/2002 | Eibl |
| 2002/0133019 | A1 | 9/2002 | Klunk et al. |
| 2002/0187157 | A1 | 12/2002 | Jensen et al. |
| 2002/0187158 | A1 | 12/2002 | Mahler et al. |
| 2003/0017995 | A1 | 1/2003 | Khalifah et al. |
| 2003/0050245 | A1 | 3/2003 | Gebbink et al. |
| 2003/0059921 | A1 | 3/2003 | Sahni et al. |
| 2003/0072770 | A1 | 4/2003 | McAnalley et al. |
| 2003/0086938 | A1 | 5/2003 | Jensen et al. |
| 2003/0087407 | A1 | 5/2003 | Soto-Jara et al. |
| 2003/0109435 | A1 | 6/2003 | Prenner et al. |
| 2003/0118593 | A1 | 6/2003 | Dan et al. |
| 2003/0143223 | A1 | 7/2003 | Cabezas et al. |
| 2003/0165458 | A1 | 9/2003 | Cabezas et al. |
| 2003/0176365 | A1 | 9/2003 | Blass |
| 2003/0236391 | A1 | 12/2003 | Klunk et al. |
| 2004/0013647 | A1 | 1/2004 | Solomon et al. |
| 2004/0253595 | A1 | 12/2004 | Nakamura et al. |
| 2005/0142208 | A1 | 6/2005 | Yoo et al. |
| 2005/0142611 | A1 | 6/2005 | Vodyanoy et al. |
| 2006/0045853 | A1 | 3/2006 | Kroon-Batenburg et al. |
| 2006/0058232 | A1 | 3/2006 | Luo et al. |
| 2006/0270599 | A1 | 11/2006 | Gebbink et al. |
| 2006/0292683 | A1 | 12/2006 | Gebbink et al. |
| 2007/0003552 | A1 | 1/2007 | Gebbink et al. |
| 2007/0015133 | A1 | 1/2007 | Gerard et al. |
| 2007/0015206 | A1 | 1/2007 | Gebbink et al. |
| 2007/0151133 | A1 | 7/2007 | Hunsaker |
| 2008/0118529 | A1 | 5/2008 | Gebbink et al. |
| 2008/0207488 | A1 | 8/2008 | Gebbink et al. |
| 2008/0220446 | A1 | 9/2008 | Gebbink et al. |
| 2008/0241165 | A1 | 10/2008 | Kroon-Batenburg et al. |
| 2008/0249606 | A1 | 10/2008 | Gebbink et al. |
| 2008/0267948 | A1 | 10/2008 | Gebbink et al. |
| 2008/0299212 | A1 | 12/2008 | Kim et al. |
| 2009/0142377 | A1 | 6/2009 | Gebbink et al. |
| 2009/0155254 | A1 | 6/2009 | Gebbink et al. |
| 2009/0191228 | A1 | 7/2009 | Gebbink et al. |
| 2009/0202980 | A1 | 8/2009 | Gebbink et al. |
| 2010/0015126 | A1 | 1/2010 | Gebbink et al. |

FOREIGN PATENT DOCUMENTS

| | | |
|---|---|---|
| DE | 197 35 902 A1 | 2/1999 |
| EP | 0 234 051 | 9/1987 |
| EP | 0 319 144 A1 | 6/1989 |
| EP | 0 321 703 A1 | 6/1989 |
| EP | 0 494 848 A1 | 7/1992 |
| EP | 0589181 | 3/1994 |
| EP | 0 955 312 A2 | 11/1999 |
| EP | 1 130 031 A1 | 9/2001 |
| EP | 1 179 588 A1 | 2/2002 |
| EP | 1 152 004 B1 | 5/2003 |
| EP | 1 380 290 | 1/2004 |
| EP | 1 449 536 A1 | 8/2004 |
| EP | 1 978 362 A2 | 10/2008 |
| EP | 1 536 778 B1 | 12/2008 |
| EP | 1 257 582 B1 | 4/2009 |
| JP | 171638/1989 | 7/1998 |
| JP | 509457/1998 | 9/1998 |
| JP | 2001-519753 | 10/2001 |
| WO | WO 90/14102 | 11/1990 |
| WO | WO 91/18610 | 12/1991 |
| WO | WO 91/19488 | 12/1991 |
| WO | WO 92/11847 | 7/1992 |
| WO | WO 92/15677 | 9/1992 |
| WO | WO 94/01116 | 1/1994 |
| WO | WO 94/20083 | 9/1994 |
| WO | WO 94/28909 | 12/1994 |
| WO | WO 95/20979 | 8/1995 |
| WO | WO 96/15799 | 5/1996 |
| WO | WO 96/39834 | 12/1996 |
| WO | WO 97/21728 | 6/1997 |
| WO | WO 97/26919 | 7/1997 |
| WO | WO 97/46547 | 12/1997 |
| WO | WO 98/06418 | 2/1998 |
| WO | WO 99/02545 | 1/1999 |
| WO | WO 99/09999 | 3/1999 |
| WO | WO 99/21565 | 5/1999 |
| WO | WO 00/04052 | 1/2000 |
| WO | WO 00 09562 A1 | 2/2000 |
| WO | WO 00/59493 | 10/2000 |
| WO | WO 00/66717 | 11/2000 |
| WO | WO 00/68263 | 11/2000 |
| WO | WO 01/07474 A1 | 2/2001 |
| WO | WO 01/12598 A2 | 2/2001 |
| WO | WO 01/50134 A2 | 7/2001 |
| WO | WO 01/53335 A3 | 7/2001 |
| WO | WO 01/58476 A2 | 8/2001 |
| WO | WO 01/62284 A2 | 8/2001 |
| WO | WO 01/62799 A2 | 8/2001 |
| WO | WO 02/16333 A2 | 2/2002 |
| WO | WO 02/053092 | 7/2002 |
| WO | WO 02/097444 A2 | 12/2002 |
| WO | WO 02/099098 A1 | 12/2002 |
| WO | WO03/002141 | 1/2003 |
| WO | WO 03/006893 A2 | 1/2003 |
| WO | WO 03/064446 A2 | 8/2003 |
| WO | WO 03/073106 A2 | 9/2003 |
| WO | WO 2004/004698 A2 | 1/2004 |
| WO | WO 2004/007545 | 1/2004 |
| WO | WO 2005/019434 A2 | 3/2005 |
| WO | WO 2005/042569 A1 | 5/2005 |
| WO | WO 2006/006172 A2 | 1/2006 |
| WO | WO 2006/098621 A2 | 9/2006 |
| WO | WO 2006/101387 | 9/2006 |
| WO | WO 2007/008069 A2 | 1/2007 |
| WO | WO 2007/008070 A2 | 1/2007 |
| WO | WO 2007/008071 A2 | 1/2007 |
| WO | WO 2007/008072 A2 | 1/2007 |
| WO | WO 2007/008073 A2 | 1/2007 |
| WO | WO 2007/018400 A1 | 2/2007 |
| WO | WO 2007/094668 | 8/2007 |
| WO | WO 2007/108675 A1 | 9/2007 |

OTHER PUBLICATIONS

Adessi et al., Abstract, Beta-sheet breaker strategy for the treatment of Alzheimer's disease. Drug Development Res 56(2): 184-193, 2002.

Baldwin et al., Stable-isotope-labeled peptides in study of protein aggregation, Methods Enzymol., 1999, pp. 576-591, vol. 309.

Blondelle et al., Abstract, Polyalanine-based peptides as models for self-associated beta-pleated-sheet complexes. Biochemistry 36: 8393-8400, 1997.

Bouma et al., "Glycation Induces Formation of Amyloid Cross-β Structure in Albumin," The Journal of Biological Chemistry, Oct. 24, 2003, pp. 41810-41819, vol. 278, No. 43.

Bronsveld et al., "Use of glucose-insulin-potassium (GIK) in human septic shock," Critical Care Medicine, 1985, pp. 566-570, vol. 13, No. 7.

Cardoso et al., "Aprotinin binding to amyloid fibrils," Eur. J. Biochem., 2000, pp. 2307-2311, vol. 267.

Chauhan et al., "Metal Cations Defibrillize the Amyloid Beta-Protein Fibrils," Neurochemical Research, 1997, pp. 805-809, vol. 22, No. 7.

Chothia et al., Canonical structures for the hypervariable regions of immunoglobulins, J. Mol. Biol., 1987, pp. 901-917, vol. 196.

Claessen et al., A Novel Class of Secreted Hydrophobic Proteins is Involved in Aerial Hyphae formation in *Streptomyces coelicolor* by Forming Amyloid-like Fibrils, Genes & Development, 2003, pp. 1714-1726, vol. 17, Cold Spring Harbor Laboratory Press.

Delgado et al., Antibodies against human cell receptors, CD36, CD41a and CD62P crossreact with porcine platelets, Cytometry Part B (Clinical Cytometry), 2003, pp. 62-67, vol. 56b.

Esler et al., Deposition of soluble amyloid-beta onto amyloid templates: With application for the identification of amyloid fibril extension inhibitors, Methods Enzymol., 1999, pp. 350-374, vol. 309.

Gebbink et al., Amyloids—A Functional Coat for Microorganisms, Nature Reviews Microbiology, Apr. 2005, pp. 333-341, vol. 3.

Golabek et al., The interaction between Apolipoprotein E and Alzheimer's amyloid beta-peptide is dependent on beta-peptide conformation. J Biol Chem 271(18): 10602-10606, 1996.

Hetenyi et al., Abstract, Computational studies on the binding of the beta-sheet breaker (BSB) peptides on amyloid betaA(1-42). J. Molec. Structure, 2001, pp. 25-31, vol. 542.

Jackson et al., "Glucose Infusions Increase Plasma Levels of Amyloid Proteins in High Density Lipoproteins," Biomedicine, 1980, pp. 245, vol. 33.

Kim et al., Thermodynamic beta-sheet propensities measured using a zinc-finger host peptide, Nature, 1993, pp. 267-270, vol. 362.

Korol et al., "Glucose, memory, and aging," Am. J. Clin. Nutr., 1998, pp. 746S-771S, vol. 67 (Suppl.).

Kranenburg et al., "Tissue-Type Plasminogen Activator is a Multiligand Cross-Beta Structure Receptor," Current Biology, Oct. 29, 2002, pp. 1833-1839, vol. 12.

Levine III, et al., Screening for pharmacologic inhibitors of amyloid fibril formation, Methods Enzymol., 1999, pp. 467-476, vol. 309.

Lodish et al., Molecular Cell biology, 4*th* Edition, 2000, W.H. Freeman & Co., Figure 22.

Maesaki et al., The structural basis of rho effector recognition revealed by the crystal structure of human rhoA complexed with the effector domain of PKN/PRK1, Mol. Cell., 1999, pp. 793-803, vol. 4.

Maggio et al., "Brain Amyloid—A Physicochemical Perspective," Brain Pathology, 1996, pp. 147-162, vol. 6.

Marks et al., Infective Endocarditis Successfully Treated in Extremely Low Birth Weight Infants With Recombinant Tissue Plasminogen Activator, Pediatrics, Jan. 2002, pp. 153-158, vol. 109, No. 1.

Minor et al., Context is a major determinant of beta-sheet propensity, Nature, 1994, pp. 264-267, vol. 371.

Ockenhouse et al., Sequestrin, a CD36 recognition protein on *Plasmodium falciparum* malaria-infected erythrocytes identified by anti-idiotype antibodies, Proc. Natl. Acad. Sci. USA, 1991, pp. 3175-3179, vol. 88.

Partial European Search Report, EP 02 07 7797, dated Dec. 13, 2002.

Partial European Search Report, EP 05 07 5656, dated Sep. 7, 2005.

PCT International Preliminary Examination Report, PCT/NL03/00501, dated Oct. 28, 2004.

PCT International Search Report, PCT/NL2003/000501, dated Mar. 31, 2004.

PCT International Search Report, PCT/NL2006/000143, dated Jan. 22, 2007.

Pepys, M. B., "Pathogenesis, diagnosis and treatment of systemic amyloidosis," Philosophical Transactions of the Royal Society of London B Biological, 2001, pp. 203-211, vol. 356, No. 1406.

Permanne et al., Reduction of amyloid load and cerebral damage in a transgenic mouse model of Alzheimer's disease by treatment with a beta-sheet breaker peptide. Faseb J. 16(8):860-862, 2002.

Reinbold, J., "Akuttherapie der diabetischen Notfalle," Notfallmedizin, 2002, pp. 82-84, vol. 28.

Reixach et al., Inhibition of beta-amyloid-induced neurotoxicity by imidazopyridoindoles derived from a synthetic combinatorial library, J. Struct. Biol. 2000, pp. 247-258, vol. 130.

Sigurdsson et al., Abstract, In vivo reversal of amyloid-beta lesions in the rat brain. J Neruopath Exp Neurol 59(1): 11-17, 2000.

Soto C et al., Beta-sheet breaker peptides inhibit fibrillogenesis in a rat brain model of amyloidosis: implications for Alzheimer's therapy. Nat Med. 4(7):822-826, 1998.

Soto C et al., Abstract, Inhibition of Alzheimer's amyloidosis by peptides that prevent beta-sheet conformation. Biochem Biophys Res Commun. 226(3):672-680, 1996.

Soto C., Abstract, Alzheimer's and prion disease as disorders of protein conformation: implications for the design of novel therapeutic approaches. J Mol Med. 77(5):412-418, 1999.

Soto C., Abstract, Beta-amyloid disrupting drugs. CNS Drugs 12(5): 347-356, 1999.

Soto C., Abstract, Plaque busters: strategies to inhibit amyloid formation in Alzheimer's disease. Mol Med Today. 5(8):343-350, 1999.

Sunde et al., "Common Core Structure of Amyloid Fibrils by Synchrotron X-ray Diffraction," J. Mol. Biol., 1997, pp. 729-739, vol. 273.

Testa et al, "The Effect of Different Glucose Endovenous Administrations on Amylin and Insulin Blood Concentration in Healthy Subjects," J. Biol. Res.—Boll. Soc. It. Biol. Sper., 1996, pp. 103-108, vol. 72, No. 3-4.

Vartio et al., Monoclonal antibody against the N-terminal end of human plasma fibronectin, Biochem. J., 1983, pp. 147-151, vol. 215.

Walsh et al., Amyloid beta-protein fibrillogenesis, J. Biol. Chem., 1999, pp. 25945-25952, vol. 274.

Wasterlain et al., "Status Epilepticus in Immature Rats," Arch Neurol, Dec. 1976, pp. 821-827, vol. 33.

Wood et al., Abstract, Prolines and amyloidogenicity in fragments of the Alzheimer's peptide beta/A4. Biochemistry 34: 724-730, 1995.

Yutani et al., "The Process of Amyloid-like Fibril Formation by Methionine Aminopeptidase from a Hyperthermophile, *Pyrococcus furiosus*," Biochemistry, 2000, pp. 2769-2777, vol. 39.

Zhang et al., The anatomy of protein beta-sheet topology, J. Mol. Biol., 2000, pp. 1075-1089, vol. 299.

Dubois et al., Thrombin binding to GPIbalpha induces integrin alphaIIbbeta3 dependent platelet adhesion to fibrin in ex vivo flowing whole blood, Thrombosis and Haemostasis, Feb. 2004; pp. 233-237, vol. 91, No. 2.

PCT International Search Report, PCT/NL2006/000149, dated May 14, 2007.

Roth et al., Abstract, Differential Engagement of Platelet CD36 in Fibrin Clot Retraction Versus Aggregation, Blood and 45th Annual Meeting of the American Society of Hematology, Nov. 16, 2003, pp. 62b, vol. 102, No. 11.

Faculty of 1000 Biology: Evaluations for Maas C et al., J Biol Chem Jan. 26, 2007 282 (4): 2229-36, http://www.f1000biology.com/article/id/1060927/evaluation.

Maas et al., "A Role for Protein Misfolding in Immunogenicity of Biopharmaceuticals," J Biol Chem, Jan. 26, 2007, pp. 2229-2236, vol. 282, No. 4. Abstract.

Rosenberg et al., "Effects of Protein Aggregates: An Immunologic Perspective," The AAPS Journal 2006, pp. E501-E507, vol. 8, No. 3.

Maas et al., "A Role for Protein Misfolding in Immunogenicity of Biopharmaceuticals," Daily Updated-Technology citing J Biol Chem, Jan. 26, 2007, pp. 2229-2236, vol. 282, No. 4.

Frid et al., Congo red and protein aggregation in neurodegenerative diseases, Brain. Res. Rev., 2007, pp. 135-160, vol. 53, No. 1.

Lueking et al., Protein biochips: a new and versatile platform technology for molecular medicine, Drug. Discov. Today, 2005, pp. 789-794, vol. 10.

Narang et al., Enhanced biosensor performance using an avidin-biotin bridge for antibody immobilization, Proc. SPIE, 1997, pp. 1987-2194, vol. 2980.

Torrent et al., Insights into alternative prion protein topologies induced under high hydrostatic pressure, J. Phys., Condense. Matter., 2004, pp. SI059-S1065, vol. 16, Issue 14.

Gupta-Bansal et al., Congo red inhibits proteoglycan and serum amyloid P binding to amyloid beta fibrils, J. Neurochem. 1998, pp. 292-298, vol. 10, No. 1.

Voropai et al. Spectral properties of thioflavin T and its complexes with amyloid fibrils, J. Appl. Spectrosc., 2003, pp. 868-874, vol. 70.

Yakovlev et al., Biochemistry, 2000, pp. 15730-15741, vol. 39.

Lowe et al., Journal of Molecular Recognition, 1998, pp. 194-199, vol. 11.

O'Nuallain et al., Conformational Abs recognizing a generic amyloid fibril epitope, Proceedings of the National Academy of Sciences of USA, Feb. 5, 2002, pp. 1485-1490, vol. 99, No. 3, National Academy of Science, Washington, DC, USA.

Hock et al., Generation of antibodies specific for beta-amyloid by vaccination of patients with Alzheimer disease, Nature Medicine, Nov. 2002, pp. 1270-1275, vol. 8, No. 11, Nature America, New York, US.

Goldsteins et al., Exposure of cryptic epitopes on transthyretin only in amyloid and in amyloidogenic mutants, Proceedings of the National Academy of Sciences of USA, Mar. 16, 1999, pp. 3108-3113, vol. 96, No. 6, National Academy of Science, Washington, DC, USA.

Hrncic et al., Antibody-mediated resolution of light chain-associated amyloid deposits, American Journal of Pathology, Oct. 2000, pp. 1239-1246, vol. 157, No. 4, Philadelphia, PA, US.

Marciani, Vaccine adjuvants: Role and mechanisms of action in vaccine immunogenicity, Drug Discovery Today, Oct. 15, 2003, pp. 934-943, vol. 8, No. 20.

Wallberg et al., Vaccination with myelin oligodendrocyte glycoprotein adsorbed to alum effectively protects DBA/1 mice from experimental autoimmune encephalomyelitis, European Journal of Immunology, Jun. 2003, pp. 1539-1547, vol. 33, No. 6.

Speidel et al., Priming of Cytotoxic T Lymphocytes by Five Heataggregated Antigens in Vivo: Conditions, Efficiency, and Relation to Antibody Responses, European Journal of Immunology, /Sep. 1997, pp. 2391-2399, vol. 27, No. 9.

Lu Xiuhua et al., A mouse model for the evaluation of pathogenesis and immunity to influenza A (H5N1) viruses isolated from humans, Journal of Virology, Jul. 1999, pp. 5903-5911, vol. 73, No. 7, The American Soceity for Microbiology, US.

Welters et al., Chemically synthesized protein as tumour-specific vaccine: immunogenicity and efficacy of synthetic HPV16 E7 in the TC-1 mouse tumour model, Dec. 2, 2004, pp. 305-311, vol. 23, No. 3.

Kim Tae-Yoon et al., Both E7 and CpG-oligodeoxynucleotide are required for protective immunity against challenge with human papillomavirus 16 (E6/E7) immortalized tumor cells: Involvement of CD4+ and CD8+ T cells in protection, Cancer Research, Dec. 15, 2002, pp. 7234-7240, vol. 62, No. 24.

Tumpey et al., Mucosal delivery of inactivated influenza vaccine induces B-cell-dependent heterosubtypic cross-protection against lethal influenza A H5N1 virus infection, Journal of Virology, Jun. 2001, pp. 5141-5150, vol. 75, No. 11, The American Society for Microbiology, US.

Heckels et al., Vaccination Against Gonorrhoea: The Potential Protective Effect of Immunization with a Synthetic Peptide Containing a Conserved Epitope of Gonococcal Outer Membrane Protein IB, Vaccine, Jun. 1, 1990, pp. 225-230, vol. 8, No. 3, Butterworth Scientific, Guildford, GB.

Fan et al., Preclinical study of influenza virus A M2 peptide conjugate vaccines in mice, ferrets, and rhesus monkeys, Vaccine, Aug. 13, 2004, pp. 2993-3003, vol. 22, No. 23-24, Butterworth Scientific, Guildford, GB.

Cockerill et al., In vivo characterization of bioconjugate B cell toleragens with specificity for autoantibodies in antiphospholipid syndrome, International Immunopharmacology, Nov. 2003, pp. 1667-1675, vol. 3, No. 12.

PCT International Search Report, PCT/NL2006/000362, dated Feb. 5, 2007.

PCT International Search Report, PCT/NL2006/000361, dated Mar. 29, 2007.

PCT International Search Report, PCT/NL2006/000365, dated Jan. 12, 2007.

PCT International Search Report, PCT/NL2006/000364, dated Mar. 28, 2007.

PCT International Search Report, PCT/NL2006/000363, dated Dec. 21, 2006.

Tang et al., Anti-inflammatory properties of triblock siloxane copolymer-blended materials, Biomaterials, 1999, pp. 1365-1370, vol. 20, No. 15.

Grudzielanek et al., Solvational Tuning of the Unfolding, Aggregation and Amyloidogenesis of Insulin, Journal of Molecular Biology, Aug. 26, 2005, pp. 879-894, vol. 352, No. 4.

Kawahara et al., Aluminum promotes the aggregation of Alzheimer's amyloid bet-protein in vitro, Biochemical and Biophysical Research Communications, Jan. 28, 1994, pp. 531-535, vol. 198, No. 2.

Renard et al., Catheter Complications Associated with Implantable Systems for Peritoneal Insulin Delivery, Diabetes Care, Mar. 1995, pp. 300-306, vol. 18, No. 3.

Gonzalez-McQuire et al., Fabrication of hydroxyapatite sponges by dextran sulphate/amino acid templating, Biomaterials, Jun. 3, 2005, pp. 6652-6656, vol. 26, No. 33.

Muramatsu et al., In vitro evaluation of the heparin-coated Gyro C1E3 blood pump, Artificial Organs, Jul. 2001, pp. 585-590, vol. 25, No. 7.

Van Beusekom et al., Abstract, Fibrin and basement membrane components, as a biocompatible and thromboresistant coating for metal stents, European Heart Journal, pp. 378, vol. 15.

Adachi et al., Direct observation of photolysis-induced tertiary structural changes in hemoglobin, PNAS, Jun. 10, 2003, pp. 7039-7044, vol. 100, No. 12.

Bode et al., Antibody-directed Fibrinolysis. The Journal of Biological Chemistry (1989). pp. 944-948, vol. 264, No. 2.

Boehm et al., Antiangiogenic therapy of experimental cancer does not induce acquired drug resistance, Nature. 1997, pp. 404-407, vol. 390.

Bouma et al., Efficacy and Stability of a Subunit Vaccine Based on Glycoprotein E2 of Classical Swine Fever Virus, Vet Microbiol., 66, 101-114 (1999).

Bouma, B. et al., Adhesion Mechanism of Human Beta(2)-Glycoprotein 1 to Phospholipids Based on its Crystal Structure, EMBO J., 18, 5166-5174 (1999).

Brandenburg, K., Koch, M.H. & Seydel, T.J., Biophysical Characterisation of Lysozyme Binding to LPS Re and Lipid A, Eur. J. Biochem., 258, 686-695 (1998).

Butovsky, et al. Activation of Microglia by Aggregated Beta-Amyloid or Lipopolysaccharide Impairs MHC-II Expression and Renders them Cytotoxic whereas IFN-gamma and IL-4 Render them Protective. Mol. Cell Neurosci., (2005).

De Laat, B., et al., IgG Antibodies That Recognize Epitope Gly40-Arg43 in Domain I of {beta}2-glycoprotein 1 Cause LAC and Their Presence Correlates Strongly with Thrombosis. Blood. 105, 1540-1545 (2005).

De Laat, et al., Beta2-glycoprotein I-dependent lupus anticoagulant highly correlates with thrombosis in the antiphospholipid syndrome, Blood, 104, 3598-3602 (2004).

Doig et al., Binding of Laminin and Fibronectin by the Trypsin-resistant Major Structural Domain of the Crystalline Virulence Surface Array Protein of Aeromonas salmonicida, The Journal of Biological Chemistry, 1992, pp. 43-49. vol. 267, No. 1.

Dooley et al., Three-Dimensional Structure of an Open Form of the Surface Layer from the Fish Pathogen Aeromonas salmonicida, Journal of Bacteriology, Jan. 1989. pp. 190-197. vol. 171.

Fassbender, K. et al., The LPS receptor (CD14) Links Innate Immunity with Alzheimer's Disease, FASEB J., 18, 203-205 (2004).

Fleury et al., Abstract. Molecular assembly of plasminogen and tissue-type plasminogen activator on an evolving fibrin surface, Eur. J. Biochem., 1993, pp. 549-556, vol. 216.

Folkman, J., Clinical applications of research on angiogenesis, Semin. Med. Beth Israel Hosp., 1995b, pp. 1757-1763, vol. 333.

Folkman, J., Fighting cancer by attacking its blood supply, SE Am., 1996, pp. 150-154, vol. 275.

Folkman, Judah, Abstract. Angiogenesis in cancer, vascular, rheumatoid and other diseases, Nat. Med., 1995, pp. 27-31, vol. 1.

Fu et al. (2008) Sulfate stabilizes the folding intermediate more than the native structure of endostatin. Archives of Biochemistry and Biophysics 471: 232-239.

Ge et al., Fibrinogen Degradation Product Fragment D Induces Endothelial Cell Detachment by Activation of Cell-mediated Fibrinolysis, J. Clin. Invest, Dec. 1992. pp. 2508-2516, vol. 90.

Genbank Public DNA Database. Accession No. 2B4X__I, Mourey et al., Sep. 27, 2005. pp. 1-3 <http://www.ncbi.nlm.nih.gov...> (visited Jan. 15, 2009).

Genbank Public DNA Database. Accession No. 2B4X__L, Mourey et al., Sep. 27, 2005, pp. 1-3 <http://www.ncbi.nlm.nih.gov...> (visited Jan. 15, 2009).

Han et al. (2007) Contributions of Zn(II)-binding to the structural stability of endostatin. FEBS Letters 581: 3027-3032.

He et al. (2006) Deficiency of disulfide bonds facilitating fibrillogenesis of endostatin. J. Biol. Chem. 281(2): 1048-1057.

Hoppener. J.W. et al., Extensive Islet Amyloid Formation is Induced by Development of Type II Diabetes Mellitus and Contributes to its Progression: Pathogenesis of Diabetes in a Mouse Mode, Diabetologia, 42, 427-434(1999).

Hoppener et al., Islet Amyloid and Type 2 Diabetes Mellitus. N. Engl. J. Med., 343, 411-419 (2000).

Horbach et al., Lupus Anticoagulant is the Strongest Risk Factor for both Venous and Arterial Thrombosis in Patients with Systemic Lupus Erythematosus. Comparison between Different Assays for the Detection of Antiphospholipid Antibodies, Thromb. Haemost., 76. 916-924 (1996).

Horbach, et al., The Prevalence of a Non-phospholipid-binding Form of Beta2-Glycoprotein I in Human Plasma—Consequences for the Development of Anti-Beta2-glycoprotein 1 Antibodies. Thromb. Haemost., 80, 791-797 (1998).

Hu et al., Abstract. Procoagulant activity in cancer cells is dependent on tissue factor expression, Oncol Res., 1994. pp. 321-327, vol. 6, No. 7.

Hu et al., Angiogenin Enhances Actin Acceleration of Plasminogen Activation, Biochemical and Biophysical Communications, Dec. 15, 1993. pp. 682-687. vol. 197. No. 2.

Huang et al., Probing Three-Dimensional Structure of Bovine Serum Albumin by Chemical Cross-Linking and Mass Spectrometry, Journal of American Soc. Mass Spectrum. Aug. 2004, pp. 1237-1247, vol. 15, No. 8.

Hulst et al., Glycoprotein El of Hog Cholera Virus Expressed in Insect Cells Protects Swine from Hog Cholera. J Virol., 67, 5435-5442 (1993).

Isik et al., Abstract. Vitronectin decreases microvascular endothelial cell apoptosis, J. Cell Physiol., May 1998, pp. 149-155, vol. 175, No. 2.

Jurgens. G. et al., Investigation into the Interaction of Recombinant Human Serum Albumin with Re-lipopolysaccharide and Lipid A., J. Endotoxin. Res., 8, 115-126 (2002).

Kayed. R. et al., Common Structure of Soluble Amyloid Oligomers Implies Common Mechanism of Pathogenesis. Science, 300. 486-489 (2003) with Supporting Online Materials.

Kim et al., Molecular Packing of Lysozyme, Fibrinogen, and Bovine Serum Albumin on Hydrophilic and Hydrophobic Surfaces Studies by Infrared—Visible Sum Frequency Generation and Fluorescence Microscopy. J. Am. Chem. Soc., Articles, published on Web Feb. 12, 2003, pp. 3150-3158, vol. 125.

Kost et al., Limited plasmin proteolysis of vitronectin. Characterization of the adhesion protein as morpho-regulatory and angiostatin-binding factor, European Journal of Biochemistry, Mar. 1, 1996, pp. 682-688, vol. 236, No. 2.

Kranenburg et al., Recombinant endostatin forms amyloid fibrils that bind and are cytotoxic to murine neuroblastoma cells in vitro, FEBS Letters, 2003. pp. 149-155.

Kuiper et al., Abstract, Clinical research on antiangiogenic therapy, Pharmacol Res., 1998. pp. 1-16, vol. 37. No. 1.

Landman, W.J., Amyloid Arthropathy in Chickens. Vet. Q., 21, 78-82 (1999).

Levine et al. Induction of Anti Phospholipid Autoantibodies by Beta2-Glycoprotein I Bound to Apoptotic Thymocytes, J. Autoimmun., 11, 413-424 (1998).

Liu, Y. et al., LPS receptor (CD14): a Receptor for Phagocytosis of Alzheimer's Amyloid Peptide. Brain, (2005).

Luijkx, et al., Relative Immunogenicity of PorA Subtypes in a Multivalent *Neisseria meningitidis* Vaccine is not Dependent on Presentation Form, Infect Immun., 71, 6367-6371 (2003).

Lutters, et al. Dimers of Beta 2-Glycoprotein I Mimic the in Vitro Effects of Beta 2-Glycoprotein I-Anti-Beta 2-Glycoprotein I Antibody Complexes., J. Biol. Chem., 276, 3060-3067 (2001).

Maas et al., Misfolded proteins activate Factor XII in humans, leading to kallikrein formation without initiating coagulation, Research article. The Journal of Clinical Investigation, Sep. 2008, pp. 3208-3218, vol. 118, No. 9.

Maas et al., Identification of fibronectin type I domains as amyloid-binding modules on tissue-type plasminogen activator and three homologs, Amyloid, Sep. 2008, pp. 166-180, vol. 15, No. 3.

Machovich et al., Denatured Proteins as Cofactors for Plasminogen Activation, Archives of Biochemistry and Biophysics, Aug. 15, 1997, pp. 343-349, vol. 344. No. 2.

Machovich et al., Myosin as cofactor and substrate in fibrinolysis. FEBS Letters. 1997, pp. 93-96, vol. 407, No. 1.

Mackay et al., Protein interactions: is seeing believing?, Trends in Biochemical Sciences, 2007. pp. 530-531, vol. 32, No. 12.

Mahdavi et al., Vaccines Against Human Papillomavirus and Cervical Cancer: Promises and Challenges, The Oncologist, 2005, pp. 528-538, vol. 10.

Mandriota, et al., Vascular endothelial growth factor-induced in vitro angiogenesis and plasminogen activator expression are dependent on endogenous basic fibroblast growth factor, J. Cell Sci., 1997. pp. 2293-2302. vol. 110.

Matsuura et al., Anticardiolipin Antibodies Recognize Beta 2-Glycoprotein I Structure Altered by Interacting with an Oxygen Modified Solid Phase Surface, J. Exp. Med., 179, 457-462 (1994).

Matzinger, P, An Innate Sense of Danger, Ann. N.Y. Acad. Sci., 961, 341-342 (2002).

Morrison, et al., Direct Evidence for Hageman Factor (Factor XII) Activation by Bacterial Lipopolysaccharides (Endotoxins), J. Exp. Med., 140, 797-811 (1974).

Munro et al., Consequences of the Non-specific Binding of a Protein to a Linear Polymer. Reconciliation of Stoichiometric and Equilibrium Titration Data for the Thrombin-Heparin Interaction, J. theor. Biol., 2000, pp. 407-418, vol. 203.

Nesheim et al., Abstract, Thrombin, thrombomodulin and TAF1 in the molecular link between coagulation and fibrinolysis, Thromb Haemost, Jul. 1997, pp. 386-391, vol. 78, No. 1.

Nguyen, Tam Luong, Three-dimensional Model of the Pore Form of Anthrax Protective Antigen. Structure and Biological Implications, Journal of Biomolecular Structure & Dynamics. 2004, pp. 253-265, vol. 22, No. 3.

Nieuwenhuizen et al., Identification of a Site in Fibrin(ogen) Which is Involved in the Acceleration of Plasminogen Activation by Tissue-Type Plasminogen Activator. Biochimica et Biopysica Acta, 1983, pp. 86-92, vol. 784.

O'Reilly et al., Endostatin: An Endogenous Inhibitor of Angiogenesis and Tumor Growth, Cell, Jan. 24, 1997, pp. 277-285.

Orgel et al., The In Situ Supermolecular Structure of Type 1 Collagen, Structure, Nov. 2001, pp. 1061-1069, vol. 9.

Ossowski et al., Abstract, Antibodies to plasminogen activator inhibit human tumor metastasis, Cell, Dec. 1983, pp. 611-619, vol. 35.

Paris et al., Anti-angiogenic activity of the mutant Dutch Aβ peptide on human brain microvascular endothelial cells, Molecular Brain Research, 2005, pp. 212-230, vol. 136.

Paris et al., Inhibition of angiogenesis by Aβ peptides, Angiogenesis, 2004, pp. 75-85, vol. 7.

PCT International Preliminary Examination Report, PCT/NL01/00155, dated May 10, 2002.

PCT International Search Report, PCT/NL01/00155, dated Sep. 4, 2001.

Poland, G.A., Vaccines against Avian Influenza—A Race against Time, N Engl J Med., 354, 1411-1413 (2006).

Radcliffe et al., A Critical Role of Lysine Residues in the Stimulation of Tissue Plasminogen Activator by Denatured Proteins and Fibrin Clots. Biochimica et Biopysica Acta, 1983, pp. 422-430, vol. 743.

Reijerkerk et al., European Journal of Cancer, 2000, pp. 1695-1705, vol. 36.

Ruf et al., Abstract, Tissue factor in cancer angiogenesis and metastasis, Curr Opin Hematol., 1996, pp. 379-384, vol. 3, No. 5.

Sara et al., Crystalline Bacterial Cell Surface Layers (S-Layers) from Cell Structure to Biomimetics, Prog. Biophys., Molec. Biol., 1996, pp. 83-111, vol. 65.

Sparknotes (2008, updated), Amino Acids and proteins. <http://www.sparknotes.com/health/aminoacids/section1.html>, p. 1.

Stack et al., Abstract, Regulation of plasminogen activation by components of the extracellular matrix, Biochemistry, May 22, 1990, pp. 4966-4970, vol. 29, No. 20.

Subang, R. et al., Phospholipid-Bound Beta2-GLycoprotein I Induces the Production of Anti-Phospholipid Antibodies, J. Autoimmun., 15, 21-32 (2000).

Takada et al., Detoxification of Lipopolysaccharide (LPS) by Egg White Lysozyme, FEMS Immunol. Med. Microbiol., 9. 255-263 (1994).

Treanor et al., Safety and Immunogenicity of an Inactivated Subvirion Influenza A (H5N1) Vaccine, N. Engl J Med., 354, 1343-1351 (2006).

Treanor et al., Dose-Related Safety and Immunogenicity of a Trivalent Baculovirus-Expressed Influenza-Virus Hemagglutinin Vaccine in Elderly Adults, J. Infect Dis., 193, 1223-1228 (2006).

UniProtKB/Swiss-Prot entry O97507, <http://www.expasy.org/cgi-bin/niceprot.pl/printable?ac=O97507>, Apr. 6, 2006 visited Feb. 25, 2008.
UniProtKB/Swiss-Prot entry P00748, <http://www.expasy.org/cgi-bin/niceprot.pl/printable?ac=p00748>, Jul. 21, 1986 visited Feb. 25, 2008.
UniProtKB/Swiss-Prot entry P98140. <http://www.expasy.org/cgi-bin/niceprot.pl/printable?ac=P98140>, Feb. 1, 1996 visited Feb. 25, 2008.
UniProtKB/Swiss-Prot entry Q04962, <http://www.expasy.org/cgi-bin/niceprot.pl/printable?ac=Q04962>, Feb. 1, 1996 visited Feb. 25, 2008.
UniProtKB/Swiss-Prot entry Q5M879, <http://www.uniprot.org/uniprot/O5M8979>, Feb. 1, 2005 visited May 15, 2009.
UniProtKB/Swiss-Prot entry Q6PER0, <http://www.expasy.org/cgi-bin/niceprot.pl/printable?ac=Q6PER0>, Jul. 5, 2007 visited Feb. 25, 2008.
Van Rijn et al., Classical Swine Fever Virus (CSFV) Envelope Glycoprotein E2 Containing one Structural Antigenic Unit Protects Pigs from Lethal CSFV Challenge, J Gen Virol., 77, 2737-2745 (1996).
Vaughn et al., The establishment of two cell lines from the insect Spodoptera frugiperda (Lepidoptera: Noctuidae), In Vitro, 13, 213-217, (1977).
Verheijen et al., EMBO 1986, vol. 5, pp. 3525-3530.
Voest, E.E., Abstract, Inhibitors of angiogenesis in a clinical perspective, Anticancer Drugs, Sep. 1996, pp. 723-727, vol. 7, No. 7.
Wang et al., A Study of the Mechanism of Inhibition of Fibrinolysis by Activated Thrombin-activable Fibrinolysis Inhibitor, The Journal of Biological Chemistry, Oct. 16, 1996, pp. 27176-27181, vol. 273, No. 42.
Wensvoort et al., Production of Monoclonal Antibodies Against Swine Fever Virus and Their use in Laboratory Diagnosis. Vet Microbiol., 12, 101-108 (1986).
Wensvoort et al., Antigenic Differentiation of Pestivirus Strains with Monoclonal Antibodies Against Hog Cholera Virus, Vet Microbiol., 21, 9-20 (1989).
Zucker et al., Abstract, Vascular endothelial growth factor induces tissue factor and matrix metalloproteinase production in endothelial cells: conversion of prothrombin to thrombin results in progelatinase A activation and cell proliferation, Int J. Cancer, Mar. 2, 1998, p. 780-786, vol. 75, No. 5.
Nunc (2009, updated) Immobilizer™ F96 MicroWell™ Plates (2009, updated) http://www.nuncbrand.com/us/page.aspx?ID_10212, p. 1.
Geylis et al., Human monoclonal antibodies against amyloid-beta from healthy adults, Neurobiol. Aging, 2005, vol. 26, pp. 597-606.
Elangovan et al., The ubiquitin-interacting motif of 26S proteaosome subunit S5a induces A549 lung cancer cell death, Biophys. Res. Comm., 2007, pp. 226-230, vol. 364.
Oomen et al., J. Mol. Biol., May 16, 2003, pp. 1083-1089, vol. 328, No. 5.
Cudic et al., Tetrahedron Letters, 2000, pp. 4527-4531, vol. 41.
Turn (biochemistry) (2009), available at http://en.wikipedia.org/wiki/Beta-turn (last modified on Jul. 21, 2009).
Sipe et al., Review: History of the Amyloid Fibril, Journal of Structural Biology, 2000, pp. 88-98.
Diaz-Avalos et al., Cross-beta Order and Diversity in Nanocrystals of an Amyloid-fonning Peptide, Journal of Molecular Biology, 2003. pp. 1165-1175.
Rochet et al., Amyloid fibrillogenesis: themes and variations, Current Opinion in Structural Biology, 2000, pp. 60-68.
Marsh et al., The Structure of Tussah Silk Fibroin, World Scientific Series in 20th Century Chemistry—vol. 10, Selected Scientific Papers, pp. 1078-1083, vol. II—Biomolecular Sciences, reprinted from Acta Crystallographica, Nov. 1955, vol. 8, Part 11.
Keck et al., Proteasome inhibition by paired helical filament-tau in brains of patients with Alzheimer's disease, Journal of Neurochemistry, 2003, pp. 115-122, vol. 85.
Giannetti et al., Fibers of tau fragments, but no full length tau, exhibit a cross β-structure: Implications for the formation of paired helical filaments, Protein Science, 2000, pp. 2427-2434, vol. 9.

Yan et al., Receptor-dependent cell stress and amyloid accumulation in systemic amyloidosis, Nature Medicine, Jun. 2000, pp. 643-651, vol. 6, No. 6.
Husemann et al., Scavenger receptor class B type I (SR-Bi) mediates adhesion of neonatal murine microglia to fibrillar β-amyloid, Journal of Neuroimmunology, 2001, pp. 142-150, vol. 114.
Yan et al., Cellular cofactors potentiating induction of stress and cytotoxicity by amyloid β-peptide, Biochimica et Biophysica Aeta, 2000, pp. 145-157, vol. 1502.
Coraci et al., CD36, a Class B Scavenger Receptor, is Expressed on Microglia in Alzheimer's Disease Brains and can Mediate Production of Reactive Oxygen species in Response to β-Amyloid Fibrils, American Journal of Pathology, Jan. 2002, pp. 101-112, vol. 160, No. 1.
Sousa et al., Familial Amyloid Polyneuropathy: Receptor for Advanced Glycation End Products-Dependent Triggering of Neuronal Inflammatory and Apoptotic Pathways, The Journal of Neuroscience, Oct. 1, 2001, pp. 7576-7586, vol. 21, No. 19.
Schmidt et al., The biology of the receptor for advanced glycation end products and its ligands, Biochimica et Biophysica Acta, 2000, pp. 99-111, vol. 1498.
Khoury et al., Microglia, Scavenger Receptors, and the Pathogenesis of Alzheimer's Disease, Neurobiology of Aging, 1998.
Fulmer, Tim, New Islets—No Immunosuppressives, Science-Business eXchange. Sep. 25, 2008, pp. 1-19, vol. 1, No. 34.
Gur et al., Editorial in Cell, Lon Takes in the Aromatic Fragrance of Unfolded Proteins, Genes Dev., 2008, pp. 2267-2277, vol. 22.
Kaganovich et al., Editorial in Cell, Misfolded Proteins Have a Parting of Ways, Nature, 2008, pp. 1088-1095, vol. 454.
Maas et al., Editorial in Cell, Aggregates Set Off Factor XII, J. Clin. Invest., 2008, pp. 3208-3218, vol. 118.
Mueller et al., Editorial in Cell. Unruly Glycoproteins are Discharged from the ER by SEL1L and Partners, Proc. Natl. Acad. Sci, 2008, pp. 12325-12330, vol. 105.
Schmaier et al., The Elusive Physiologic Role of Factor XII, The Journal of Clinical Investigation, Sep. 2008. pp. 3006-3009, vol. 118, No. 9.
Steele et al., Editorial in Cell, HSF1 Provides Protection from PrP, Proc. Natl. Acad. Sci., 2008, pp. 13626-13631, vol. 105.
Thiru Malai et al., Emerging ideas on the molecular basis of protein and peptide aggregation, Curr. Opin. Struct. Biol., 2003, pp. 146-159, vol. 13, No. 2.
Jhamb et al., Immobilized chaperones: A productive alternative to refolding of bacterial inclusion body proteins, Process Biochem., 2008, pp. 587-597, vol. 43.
Wu et al., The binding of thioflavin T and its neutral analog BTA-1 to protofibrils of the Alzheimer's disease Abeta (16-22) peptide probed by molecular dynamics simulations, J. Mol. Biol., 2008, pp. 718-729, vol. 384, No. 4.
Wang et al., Bacterial inclusion bodies contain amyloid-like structure, PLoS Biol., 2008, pp. 1791-1801, vol. 6, No. 8.
Wikipedia, 2009, updated Hsp27, en.wikipedia.org/wiki/Hsp27, pp. 1-4.
Hatters et al., The molecular chaperone, alpha-crystallin, inhibits amyloid formation by apolipoprotein, C-11, J. Biol. Chem., 2001, pp. 33755-33761, vol. 276, No. 36.
Nemes et al., Cross-linking of ubiquitin, HSP27, parkin and α-synuclein by γ-glutamyl-ε-lysine bonds in Alzheimer's neurofibrillary tangles, The FASEB Journal, Published online May 7, 2004.
Wilhelmus et al., Specific association of small heat shock proteins with the pathological hallmarks of Alzheimer's disease brains, Neuropathology and Applied Neurobiology, 2006, pp. 119-130, vol. 32.
Serpell, Louise C., Alzheimer's amyloid fibrils: structure and assembly, Biochimica et Biophysics Acta, 2000, pp. 16-30, vol. 1502.
Baumketner et al., Amyloid beta-protein monomer structure: A computational and experimental study, Protein Science, 2006, pp. 420-428, vol. 15.
Ott et al., Enhancement of humoral response against human influenza vaccine with the simple submicron oil/water emulsion adjuvant MF59, Vaccine, 1995, pp. 1557-1562, vol. 13, No. 16.

Tollis et al., Abstract, Recent Development in Avian Influenza Research: Epidemiology and Immuno prophylaxis, Veterinary Journal, 2002, pp. 202-215, vol. 164.
Office Action for U.S. Appl. No. 11/033,105 dated May 3, 2007.
Office Action for U.S. Appl. No. 11/033,105 dated Nov. 21, 2007.
Office Action for U.S. Appl. No. 11/033,105 dated Aug. 25, 2008.
Office Action for U.S. Appl. No. 11/033,105 dated May 22, 2009.
Office Action for U.S. Appl. No. 11/033,105 dated Dec. 22, 2009.
Office Action for U.S. Appl. No. 11/384,169 dated Oct. 28, 2008.
Office Action for U.S. Appl. No. 11/384,169 dated Jun. 10, 2009.
Office Action for U.S. Appl. No. 11/087,102 dated Nov. 23, 2007.
Office Action for U.S. Appl. No. 11/087,102 dated Jul. 23, 2009.
Office Action for U.S. Appl. No. 11/087,102 dated Jul. 6, 2010.
Office Action for U.S. Appl. No. 11/181,012 dated Mar. 22, 2007.
Office Action for U.S. Appl. No. 11/181,012 dated Sep. 25, 2007.
Office Action for U.S. Appl. No. 11/181,012 dated May 30, 2008.
Office Action for U.S. Appl. No. 11/181,012 dated Mar. 20, 2009.
Office Action for U.S. Appl. No. 11/181,012 dated Dec. 28, 2009.
Office Action for U.S. Appl. No. 11/995,308 dated Apr. 3, 2009.
Office Action for U.S. Appl. No. 11/995,308 dated Jan. 8, 2010.
Office Action for U.S. Appl. No. 11/661,537 dated Jun. 11, 2009.
Office Action for U.S. Appl. No. 11/661,537 dated Jan. 26, 2010.
Office Action for U.S. Appl. No. 11/181,040 dated May 31, 2007.
Office Action for U.S. Appl. No. 11/181,040 dated Jul. 15, 2008.
Office Action for U.S. Appl. No. 11/181,040 dated Nov. 27, 2007.
Office Action for U.S. Appl. No. 11/181,040 dated Jan. 12, 2009.
Office Action for U.S. Appl. No. 11/181,040 dated Oct. 29, 2009.
Office Action for U.S. Appl. No. 11/181,040 dated Jun. 23, 2010.
Office Action for U.S. Appl. No. 11/982,161 dated May 28, 2010.
U.S. Appl. No. 12/224,087, filed Feb. 18, 2009, Gebbink et al., Affinity Regions.
U.S. Appl. No. 12/225,291, filed Jan. 7, 2009, Gebbink et al., Methods of Binding of Cross-Beta Structures by Chaperones.
U.S. Appl. No. 12/741,288, to be Assigned, Gebbink et al., Immunogenic Compositions Capable of Activating T-Cells.
U.S. Appl. No. 12/291,398, filed Nov. 7, 2008, Gebbink et al., Immunogenic Compositions Capable of Activating T-Cells.
U.S. Appl. No. 12/291,369, filed Nov. 7, 2008, Gebbink et al., Improved Immunogenic Compositions.
PCT/EP2010/002180, Apr. 7, 2010, Schijns et al., Tumor Vaccines.
U.S. Appl. No. 12/800,700, filed May 19, 2010, Bouma et al., Modulating Compound.
U.S. Appl. No. 61/216,605, filed May 19, 2009, Bouma et al., Modulating Compounds.
U.S. Appl. No. 12/741,270, Gebbink et al., Enhancement of Immunogenicity of Antigens.
Garrido C. (2002) Size matters: of the small HSP27 and its large oligomers, Cell Death Differ., vol. 9, No. 5, pp. 483-485.
Salonen et al., (1985) Plasminogen and tissue-type plasminogen activator bind to immobilized fibronectin, J. Biol. Chem., vol. 260, No. 22, pp. 12302-12307.
Luyk X et al., HPLC and tandem detections to monitor conformational properties of biopharmaceuticals, Journal of Chromatography B. 2005. pp. 45-52, vol. 821.
Vermeer, L. "Uniquie protein structure offers a basis for commercial activity." Conceptuur, Dec. 2004, No. 41 (p. 18 is relevant and has been translated).
Akiyama, et al; Abstract; Inflammation and Alzheimer's disease; Neurobiol Aging. May-Jun. 2000; 21(3): 383-421.
Bachmann, et al.; Recall Proliferation Potential of Memory CD8 + T Cells and Antiviral Protection; The Journal of Immunology; 2005, 175: 4677-4685.
Coker, et al.; Moleculr chaperone properties of serum amyloid P component; FEBS Letters 473 (2000) 199-202.
Efferson, et al; Stimulation of Human T Cells by an Influenza A Vector Expressing a CTL Epitope from the HER-2/neu Protooncogene Results in Higher Numbers of Antigen-specific TCR[hl] Cells than Stimulation with Peptide, Divergent Roles of IL-2 and IL-15; Anitcancer Research 25: 715-724 (2005).

Obrenovich et al., Glycation Stimulated Amyloid Formation, Sci. Aging Knowl. Environm., Jan. 14, 2004. pp. pe3, vol. 2004, No. 2.
Ono, et al.; Radioiodinated Flavones for in Vivo Imaging of β-Amyloid Plaques in the Brain; J. Med. Chem. 2005, 48, 7253-7260.
Rao et al., Thermo and pH stable ATP-independent chaperone activity of heat-inducible Hsp70 from *Pennisetum glaucum*, Plant. Signal Behav., 2010, pp. 110-121, vol. 5, No. 2.
Tucker et al., Journal of Neuroscience, 2000, p. 3937-3946, vol. 20.
Wheeler, C.M.; Abstract; Preventive vaccines for cervical cancer; Salud p'ublica de M'exico, (Jul.-Aug. 1997).
European Patent Office Notification of Application No. 03 762 927.6 dated Oct. 4, 2006.
European Patent Office Notification for Application No. 03 762 927.6 dated Jul. 26, 2007.
European Patent Office Notification for Application No. 03 762 927.6 dated Feb. 18, 2008.
European Patent Office Summary of Facts and Submission for Applicant No. 03 762 927.6 dated May 30, 2008.
Griffioen, et al., Anginex, a designed peptide that inhibits angiogenesis, Biochem. J., 2001. pp. 233-242, vol. 354.
Jacobsen, et al., Enhanced clearance of A beta in brain by sustaining the plasmin proteolysis cascade, PNAS, Jun. 24, 2008, pp. 8754-8759, vol. 105, No. 25.
Chauhan, et al., Media from Rhabdomyosarcoma and Neuroblastoma Cell Cultures Stimulate in Vitro Aggregation and Fibrillization of Amyloid Beta-Protein, Neurochemical Research, 1997, pp. 227-232, Vo. 22, No. 2.
Dubois et al., Thrombin binding to GPIbα induces platelet aggregation and fibrin clot retraction supported by resting allbβ3 interaction with polymerized fibrin, Thromb Haemost. 2003, pp. 853-864, vol. 89.
Elghetany et al., Methods for Staining Amyloid in Tissues: A Review, Stain Technology, Jan. 1, 1988. pp. 201-211, vol. 63, No. 4.
European Search Report (08 153 132.9) dated Oct. 1, 2009.
European Search Report (EP 1 978 362 A3) dated Oct. 2, 2008.
Hajduk et al., Discovering High-Affinity Ligands for Proteins. Science, Oct. 17, 1997, pp. 497-499, vol. 278.
Hubbard et al., Spontaneous pancreatic islet amyloidosis in 40 baboons, J. Med. Primatol, 2002, pp. 84-90, vol. 31, No. 2.
Klunk et al., Development of Small Molecule Probes for the Beta-Amyloid Protein of Alzheimer's Disease, Neurobiology of Aging, 1994, pp. 691-698, vol. 15, No. 6, Elsevier Science Ltd., USA.
Merlini et al., Interaction of the anthracycline 4'-iodo-4'deoxydoxorubicin with amyloid fibrils: Inhibition of amyloidogenesis, Proc. Natl. Acad. Sci., Mar. 1995, pp. 2959-2963, vol. 92.
Nyhlin et al., Advanced glycation end product in familial amyloidotic polyneuropathy (FAP), Journal of Internal Medicine, 2000, pp. 485-492, vol. 247.
PCT International Preliminary Examination Report for PCT/NL03/00501.
Roth et al., Differential Engagement of Platelet CD36 in Fibrin clot retraction versus aggregation, Blood, Nov. 2003, 45th Annual Meeting of the American Society of Hematology, vol. 102, No. 11, San Diego, CA, USA.
Gadek, T., Strategies and Methods in the Identification of Antagonists of Protein-Protein Interactions, Structure-Guided Drug Discovery, pp. 21-24.
Demattos et al., PNAS, 2001, pp. 8850-8855, vol. 98.
Office Action for U.S. Appl. No. 11/995,308 dated Oct. 1, 2010.
U.S. Appl. No. 12/741,288, filed Aug. 30, 2010, Gebbink, et al., Immunogenic Compositions Capable of Activatintg T-Cells.
U.S. Appl. No. 12/800,700, filed May 19, 2010, Gebbink, et al., Modulating Compounds.
U.S. Appl. No. 12/741,270, filed Aug. 26, 2010, Gebbink, et al., Enhancement of Immunogenicity of Antigens.

* cited by examiner

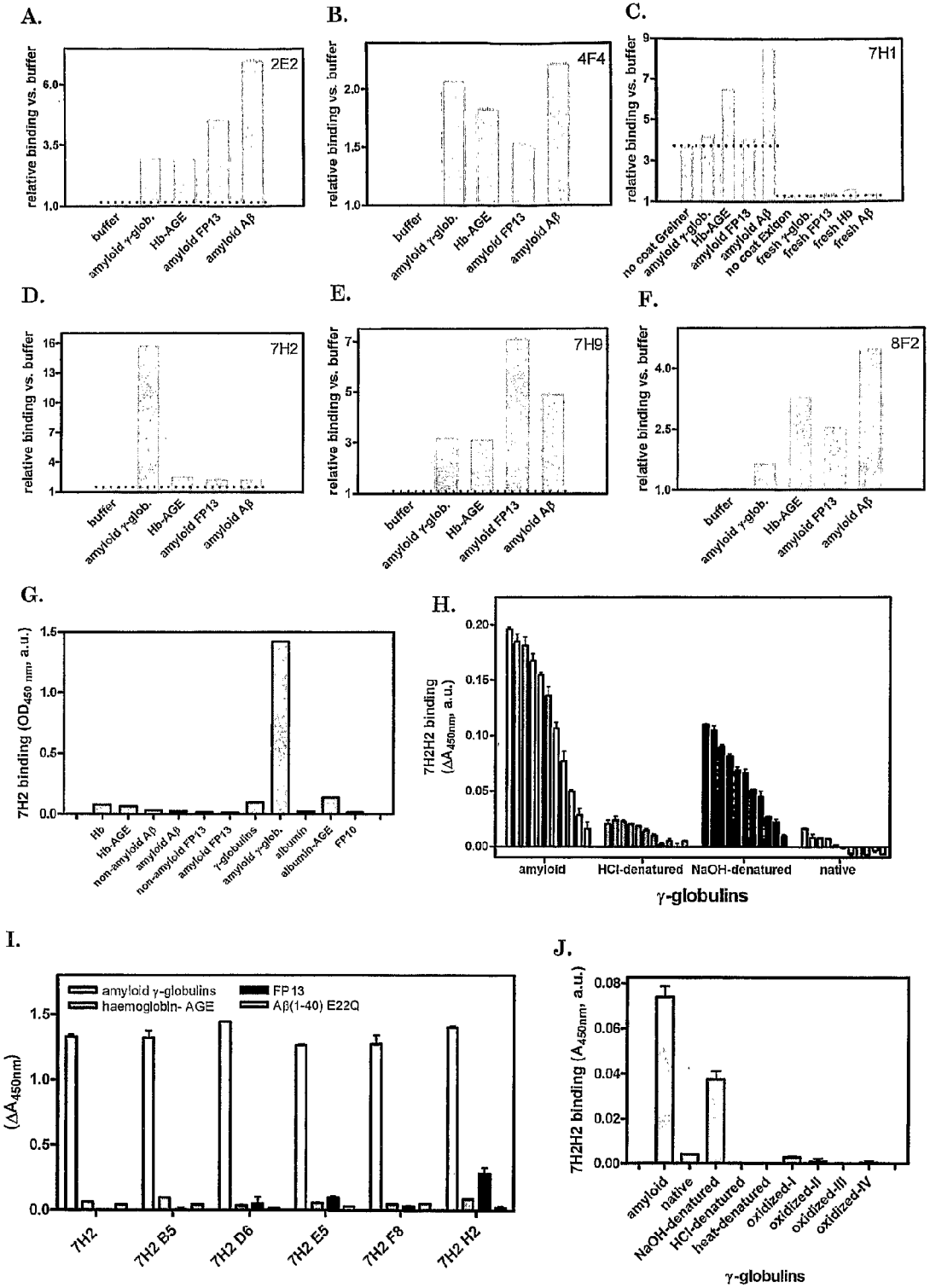

Fig. 1
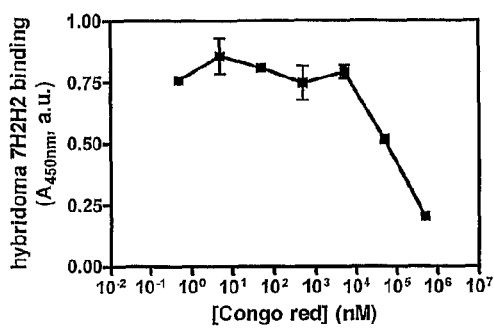
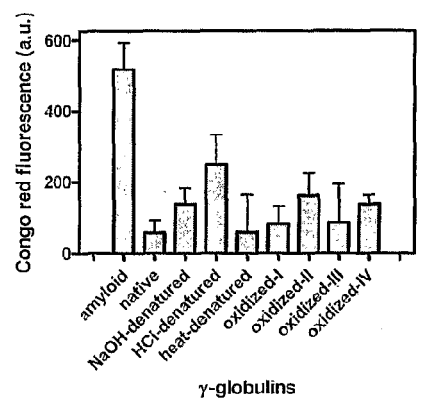
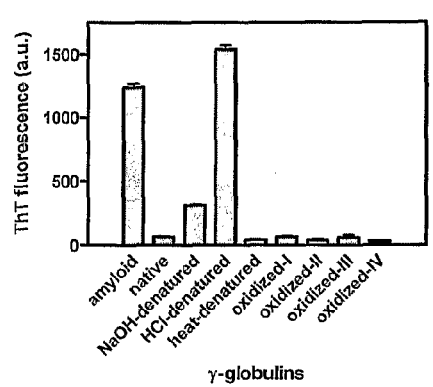
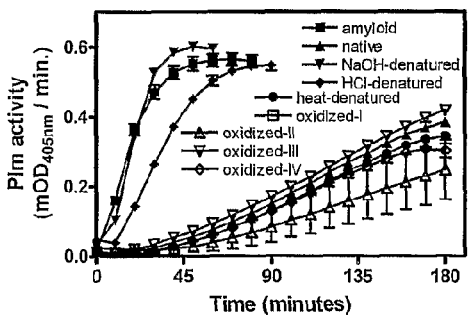
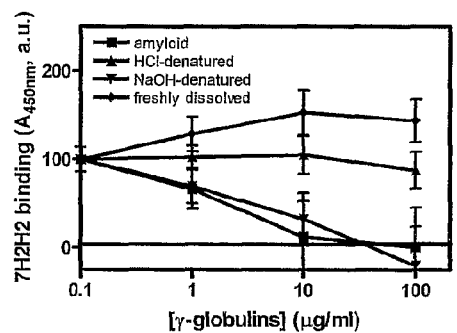

Figure 12
A
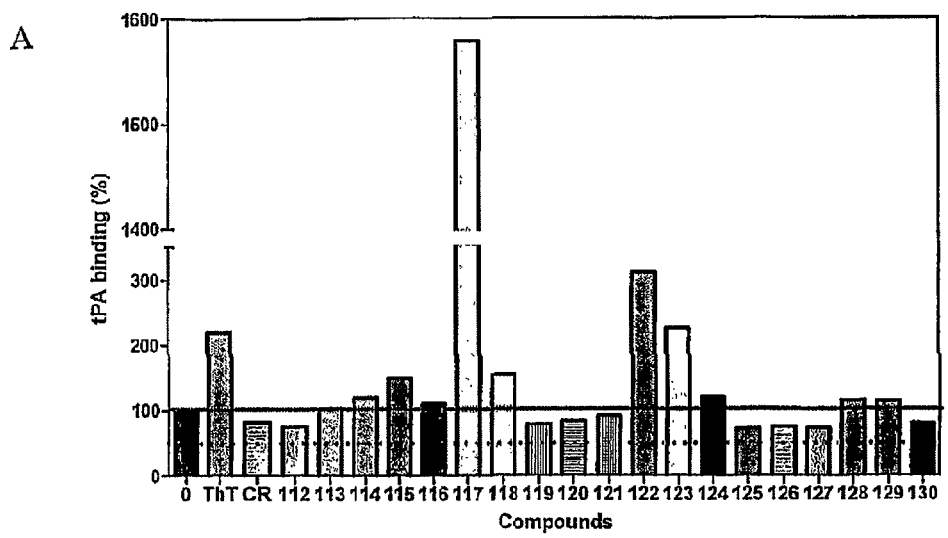
B
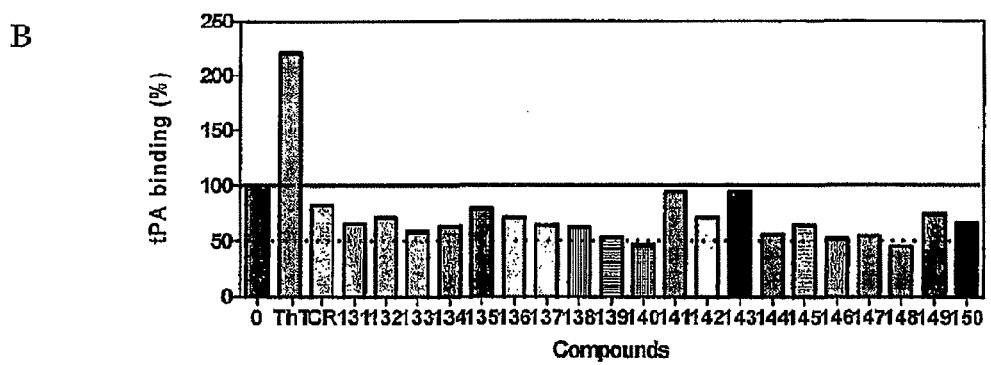
C
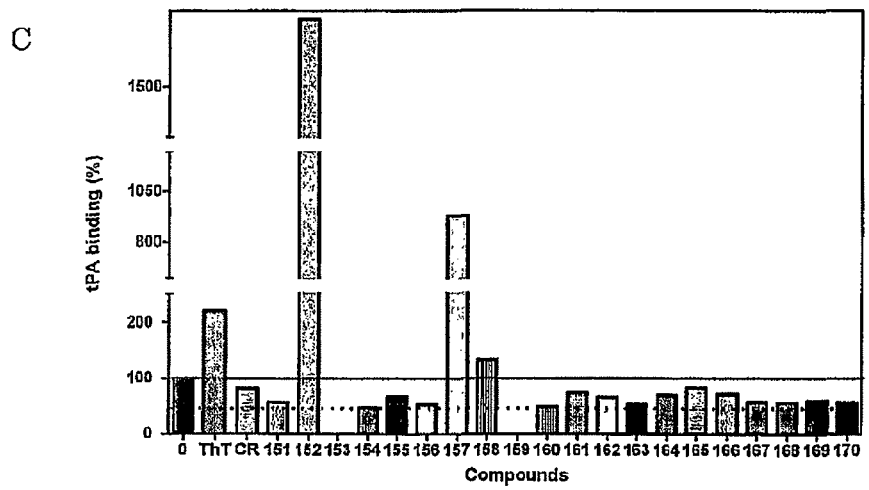

Figure 12 (continued)
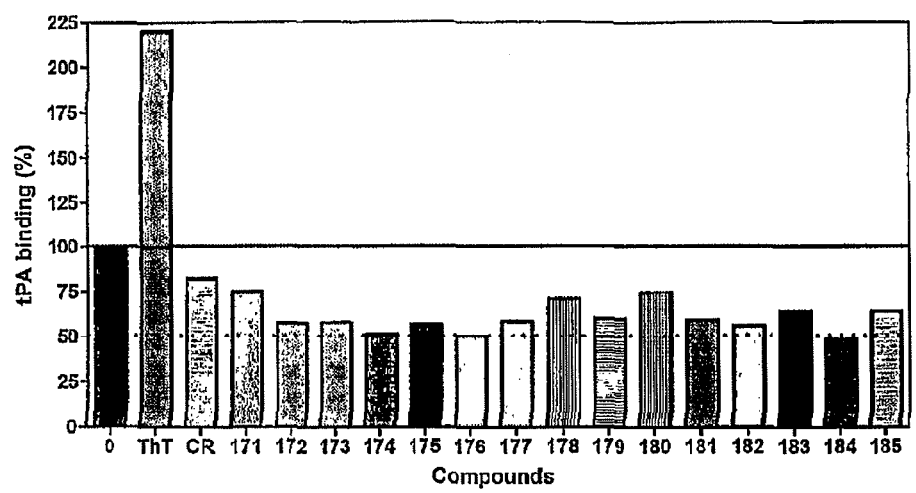
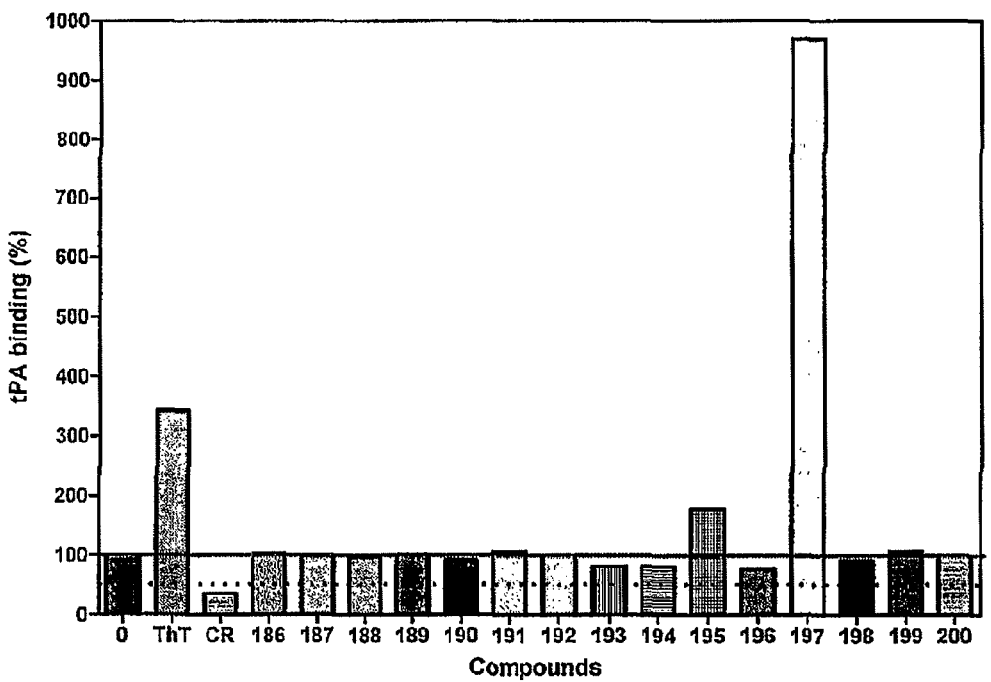

Figure 12 (continued)
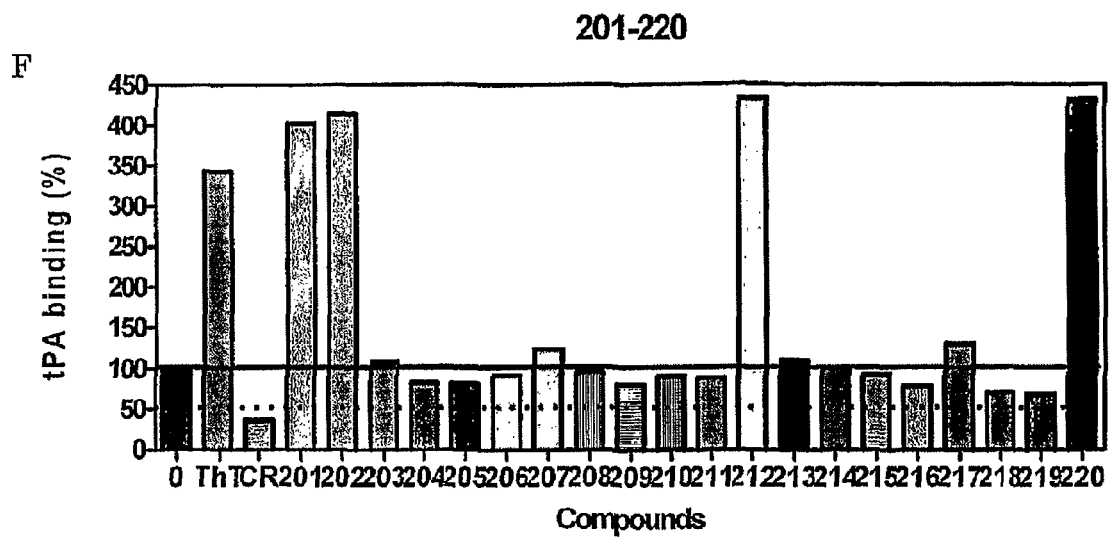
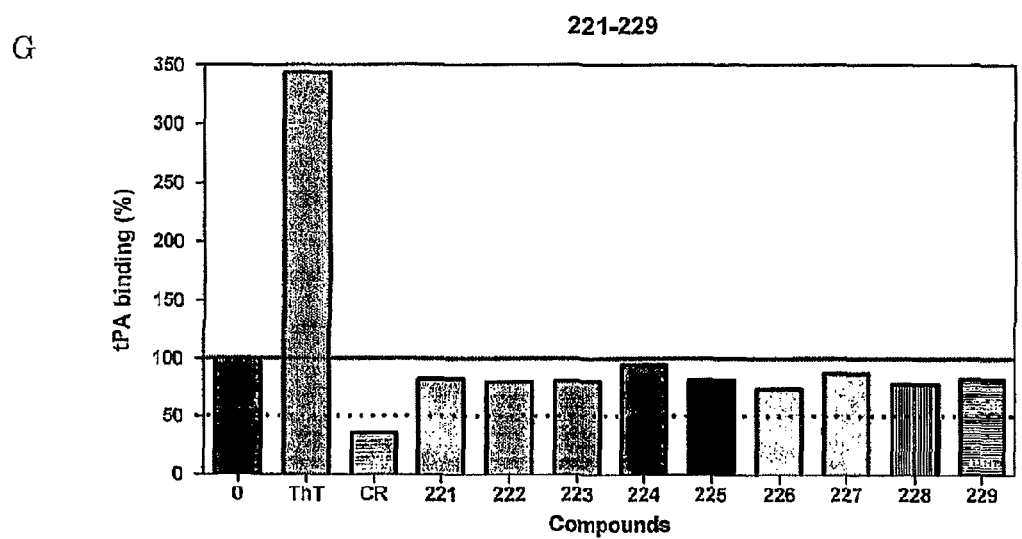

1. derivative of Dehydroglaucine
2. Thaliporphine, thalicmidine
3. Ammophedrine HBr
4. Isoboldine
5. (no name)
6. (no name)
7. (no name)
8. haematein
9. DXS500k, dextran sulphate, $5*10^5$ g/mol
10. ellagic acid hydrate
11. corynanthine
12. orcein
O. OVA heated in the presence of DMSO
C. control heated OVA
Aβ. amyloid-β positive control Figure 21 (continued)
I.
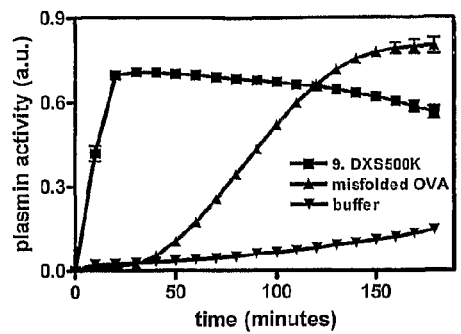
J.
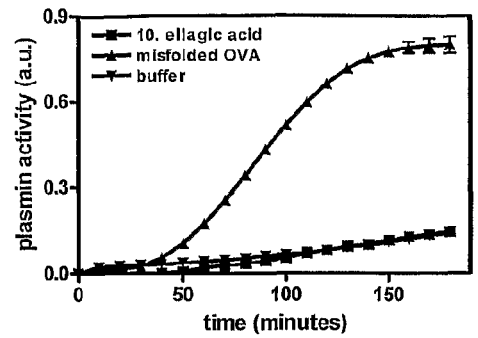
K.
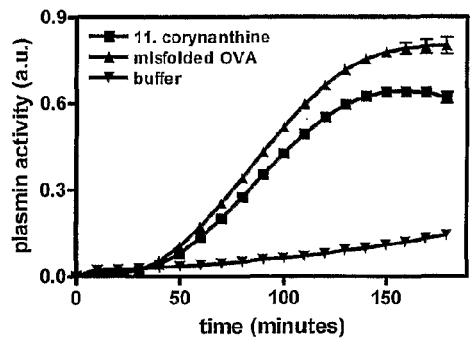
L.
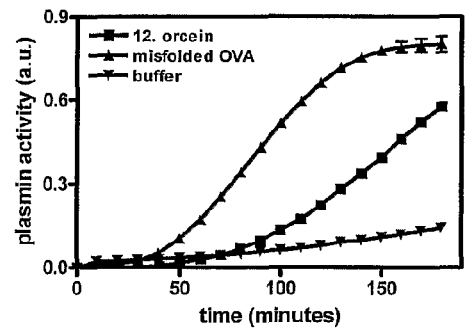

CROSS-β STRUCTURE BINDING COMPOUNDS

CROSS-REFERENCE TO RELATED APPLICATION

This application is a National Entry of PCT International Patent Application No. PCT/NL2006/000364, filed on Jul. 13, 2006, designating the United States of America, and published, in English, as PCT International Publication No. WO 2007/008072 A2 on Jan. 18, 2007, which PCT International Patent Application itself claims priority to EP 05076613.8 filed Jul. 13, 2005.

TECHNICAL FIELD

The invention relates to the field of biochemistry, biophysical chemistry, molecular biology, structural biology and medicine. More in particular, the invention relates to a cross-β structure or cross-β structure induced conformations. Even more particular, the invention relates to compounds capable of binding to a protein comprising a cross-β structure.

BACKGROUND

Nowadays, the list of proteins and peptides that are known to be able to adopt the amyloid-like cross-β structure conformation is tremendous. This has led to the idea that refolding of polypeptides from a native fold to an amyloid-like structure is an inherent property, independent of the amino-acid sequence of the polypeptides. We found that tissue-type plasminogen activator (tPA) and factor XII are specifically activated by many polypeptides, once they have adopted the cross-β structure conformation. This led us to recognize that a "cross-β structure pathway" exists that regulates the recognition and clearance of unwanted proteins.[1] Polypeptides can refold spontaneously at the end of their life cycle, or refolding can be induced by environmental factors such as pH, glycation, oxidative stress, heat, irradiation, mechanical stress, proteolysis and so on, at least part of the polypeptide refolds and adopts the amyloid-like cross-β structure conformation. This conformation is then the signal that triggers a cascade of events that induces clearance and breakdown of the obsolete particle. When clearance is inadequate unwanted polypeptides can aggregate and form toxic structures ranging from soluble oligomers up to precipitating fibrils and amorphous plaques. Such cross-β structure conformation comprising aggregates underlie various diseases, such as Alzheimer's disease, Huntington's disease, diabetes mellitus type 2, systemic amyloidoses or Creutzfeldt-Jakob's disease, depending on the underlying polypeptide that accumulates and on the part of the body where accumulation occurs.

The presence of cross-β structures in proteins triggers multiple responses. As mentioned, cross-β structure comprising proteins can activate tPA and FXII, thereby initiating the fibrinolytic system and the contact system of hemostasis. Besides activation of the coagulation system through FXII, the cross-β structure conformation may induce coagulation, platelet aggregation and blood clotting via direct platelet activation and/or the release of tissue factor (Tf) by activated endothelial cells (described in more detail in a co-pending patent application). In addition, the complement system is another example of a proteolytic cascade that is activated by cross-β structure conformation. This system can be activated by the amyloid-β peptide associated with Alzheimer's Disease or by zirconium or aluminum or titanium. The latter being compounds that can induce cross-β structure conformation in proteins. The innate and adaptive immune systems are yet another example. Amyloid-β activates the innate and adaptive immune response.[2] β2-glycoprotein I is an auto-immune antigen only upon contact with a negatively charged lipid surface, such as cardiolipin.[3] We have now shown that cardiolipin induces cross-β structure conformation in β2-glycoprotein I (described in more detail in a co-pending patent application). Moreover, we have shown that ligands for Toll-like receptors that are implicated in the regulation of immunity induce cross-β structure conformation in proteins. These ligands include lipopolysaccharide and CpG oligodeoxynucleotides (ODN) (described in more detail in a co-pending patent application).

FXII can be activated by negatively charged agents. For example, when blood is drawn into a glass tube it rapidly clots, due to activation of FXII. However, when the tube is made of plastic clotting is delayed. This mechanism of this contact system of coagulation is termed the intrinsic pathway because all clotting factors are present in plasma; in contrast to the extrinsic pathway, which requires the presence of tissue factor on the surface of cells, that is not exposed to the circulation during homeostasis. Interestingly, the nature of the FXII activator in vivo is still unknown. We now found that cross-β structure, that is formed when globular proteins unfold due to any denaturing trigger, is a trigger for FXII and contact activation. Since negatively charged surfaces, such as glass, induce denaturation of proteins, it may well be possible that activation of FXII is secondary to formation of cross-β structure by negatively charged surfaces. We have tested whether activation of FXII by dextran sulphate 500,000 Da (DXS500k) and kaolin is accompanied and mediated by cross-β structure, and our results indeed show that this is occurring. We have determined that plasma exposure to a surface of DXS500k or kaolin indeed induces cross-β structure conformation by staining with Thioflavin T (ThT) and by binding of a recombinant finger domain. In addition, we test whether the amyloid binding reagents Congo Red, ThT, recombinant finger domains of tPA, FXII, HGFA and fibronectin, or full-length tPA, FXII, HGFA, fibronectin, serum amyloid P component (SAP), anti-cross-β structure antibodies and/or a soluble fragment of receptor for advanced glycation endproducts (sRAGE) inhibit activation of FXII induced by DXS500k, kaolin, any other activating surface, or by denatured polypeptides comprising the cross-β structure conformation.

tPA is a serine protease involved in fibrin clot lysis. tPA stimulates activation of plasminogen into plasmin. Fibrin serves as an efficient cofactor in stimulating tPA mediated plasmin formation. Besides fibrin and fibrin fragments a large number of other proteins or protein fragments have been found that stimulate tPA activity, though that exhibit no apparent amino-acid sequence homology. Therefore, the anticipated common structural basis underlying the acquired tPA binding remained elusive. We recently found that the amyloid-like cross-β structure (conformation), the structural element found in amyloid deposits in diseases such as Alzheimer's disease, is a prerequisite and the common denominator in tPA-binding ligands.[1,4] FXII shows close homology with tPA and is known to be activated by amyloid-β (Aβ) and by bacteria with an amyloid core.[5] The domain structure of FXII includes, like tPA, a finger domain and its sequence shows the closest homologies with tPA. FXII also binds fibrin (Sanchez et al. 2003, ISTH XIX Congress; surface deposited fibrin activates FXII and the intrinsic coagulation pathway) and FXII can also, like tPA, mediate the conversion of plasminogen to plasmin.[6] We found that FXII, like tPA, is activated by polypeptides with amyloid-like cross-β structure conformation in general. Moreover, we established that well-known activators of FXII, DXS500k and kaolin, induce amyloid-like cross-β structure conformation in proteins and that DXS500k is only then an effective activator of FXII when an excess of protein cofactor over the amount of FXII present is added to the reaction mixture. Thus, in contrast to direct activation by binding to negatively charged surfaces, FXII is activated by (plasma) proteins that denature and form amyloid on negatively charged surfaces, or denature by any other means, e.g., pH change, exposure to radicals, proteolysis, glycation, oxidation, change in temperature. It is thus stated that the cross-β structure conformation regulates contact activation and fibrinolysis.

At present, it is assumed that activation of FXII directly involves binding to negatively charged surfaces. Based on our findings, we show that negatively charged surfaces induce amyloid cross-β structure formation and that this structure element triggers FXII activation. This finding renews the view on contact-mediated activation of blood coagulation.

In conclusion, tPA and factor XII are cross-β structure binding proteins. Moreover, cross-β structure comprising proteins can activate these proteins.

To be able to further study the role of the cross-β structure in (patho)physiology it is necessary that (more) compounds capable of binding to a protein comprising a cross-β structure, amongst others cross-β structure binding compounds, are identified. Such compounds are not only useful to be able to better understand cross-β structures, but are also very useful in respect of understanding the refolding from a native state, assembly and toxicity and are also useful for the development of diagnostic and therapeutic agents or useful as component of a diagnostic or therapeutic agent.

DISCLOSURE

The goal of the present invention is to provide methods for selecting or obtaining a cross-β structure binding compound and methods for selecting or obtaining a compound capable of binding to a cross-β structure induced conformation or capable of binding a protein comprising a cross-β structure or capable of binding selectively to a certain protein with cross-β structure and not to other proteins with cross-β structure conformation. Moreover, the invention also provides uses of such compounds.

In a first embodiment, the invention provides a method for selecting a compound capable of binding to a cross-β structure in a protein, comprising
  contacting the compound with a first protein comprising a cross-β structure and allowing the compound and the protein to interact
  determining whether the compound at least in part binds to the cross-β structure
  selecting the compound that at least in part binds to the protein with cross-β structure conformation.

A cross-β structure is defined as a part of a protein or peptide, or a part of an assembly of peptides and/or proteins, which comprises an ordered group of β-strands; typically a group of β-strands arranged in a β-sheet, in particular a group of stacked or layered β-sheets, also referred to as "amyloid." A typical form of stacked β-sheets is in a fibril-like structure in which the β-sheets may be stacked in either the direction of the axis of the fibril or perpendicular to the direction of the axis of the fibril. Of course the term peptide is intended to include oligopeptides as well as polypeptides, and the term protein includes proteins with and without post-translational modifications, such as glycosylation. It also includes lipoproteins and complexes comprising proteins, such as protein-nucleic acid complexes (RNA and/or DNA), membrane-protein complexes, etc. A β-sheet is a secondary structural element in a peptide and/or protein. A cross-β structure comprises a tertiary or quaternary structural element in a peptide and/or protein and can be formed upon, for example, denaturation, proteolysis, chemical modification, multimerization or unfolding of proteins. The cross-β structure is generally absent in non-altered globular proteins. The cross-β structure is in general composed of stacked β-sheets. In a cross-β structure the individual β-strands run either perpendicular to the long axis of a fibril, or the β-strands run in parallel to the long axis of a fibril. In some cases, the direction of the stacking of the β-sheets in cross-β structures is perpendicular to the long axis of the fibril.[1] Moreover, if it is determined that a compound binds to a cross-β structure in a protein, such a determined cross-β structure binding compound can further be used in the detection of other proteins that comprise a cross-β structure. The proteins that are detected by such a method are also included by the term cross-β binding structure.

The term cross-β structure, cross-β structure conformation and cross-β conformation will be used interchangeably herein.

We have observed that the hexapeptide FP6 can form oligomers consisting of up to 15 peptide molecules, with cross-β structure conformation. Various preparations exhibit different tPA activating properties, appear differently on TEM images, enhance Congo red fluorescence differently and have formed distinct cross-β structure conformations, as depicted from X-ray diffraction data sets. These data provide insight in the diverse nature of the cross-β structure fold. In fact, the cross-β structure fold, also referred to as β-pleated sheets, cross-β sheets or cross-β spine, is an ensemble of structures. Polypeptides differing in amino-acid sequence or length, or a polypeptide treated in different ways, may appear with cross-β structures that differ from each other to some extent. For example, the inter-β-sheet distance within a cross-β structure may vary with amino-acid sequence, peptide length, and conditions leading to the formation of a cross-β structure.

The term "first protein comprising a cross-β structure" includes a solution comprising a single type of protein or a solution comprising a set of different proteins. It is not necessary that all proteins in the solution comprise a cross-β structure. It is sufficient that only a part of the proteins comprise a cross-β structure. The term "first protein comprising a cross-β structure" also includes the situation wherein a protein is attached to the exterior a cell or wherein the protein is part of a (cell)matrix or part of a tissue. The term further includes immobilized protein in general and more specific protein immobilized on a solid surface such as an ELISA well or a bead.

Moreover, the protein also includes a fragment or an equivalent of a full-length/complete protein. The only requirement is that the fragment or equivalent comprises a cross-β structure.

Methods to determine whether a protein comprises a cross-β structure conformation are available to the skilled person. Examples of such methods include, but are not limited to staining with Congo red, Thioflavin S (ThS) or Thioflavin T (ThT), an ELISA binding assay using tPA or a functional fragment thereof, or an enzymatic assay such as a tPA activation assay, a factor XII activation assay or a X-ray fiber diffraction analysis. If it is determined or known that a certain protein or protein solution does not comprise or does not comprise sufficient cross-β structures the cross-β structure content in the protein or protein solution can be increased. Examples for the induction of a cross-β structure in a protein are provided in the experimental part herein and include factors such as those that involve changes in pH, glycation, oxidative stress, oxidation, alkylation, temperature and so on. Alternatively, a cross-β structure is induced in a protein by irradiation, mechanical stress, sonication, proteolysis, contact with or the addition of a denaturing compound, such as kaolin, dextran sulphate or an adjuvant, such as CpG-ODN or negatively charged phospholipids, including cardiolipin and so on. Hence, a method according to the invention further optionally comprises the induction of a cross-β structure in a first protein to induce or increase the amount of cross-β structure by subjecting the protein to a treatment that induces or increases the cross-β structure content. Preferably, the step is performed before the step of contacting the compound with a first protein comprising a cross-β structure and allowing the compound and the protein to interact.

The step of contacting the compound with (possible) cross-β structure binding capacity with a first protein comprising a cross-β structure can be performed in different ways. It is, for example, possible to contact a solution comprising a possible cross-β structure binding compound with a solution comprising a protein comprising a cross-β structure. It is also possible to coat a carrier (for example, a tube or a well of an ELISA plate) with the possible cross-β structure binding compound and add a solution comprising a protein comprising a cross-β structure to the coated carrier. Or the other way around, in which a protein comprising a cross-β structure is used to coat a carrier. Methods to perform coating of a carrier are well known and will, therefore, not be discussed in more detail. Independent of the exact way in which the cross-β structure binding compound and a protein comprising a cross-β structure are contacted, they are allowed to incubate/interact a sufficient amount of time to establish binding to each other. To increase the binding of a possible cross-β structure binding compound to a protein comprising a cross-β structure, the conditions for the binding are adjusted to be as optimal as possible for each situation. For example, changes of the pH, amount of salt, temperature, concentration and so on are introduced if this is considered relevant/suitable.

If either the cross-β structure binding compound or a protein comprising a cross-β structure is coated to a carrier an optional step is to separate bound and unbound material from each other by performing a washing step. In a preferred embodiment, the invention thus provides a method for selecting a compound capable of binding to a cross-β structure in a protein, the method further comprises at least one and preferably more than one (for example, two or three) washing steps to allow for separation of bound and unbound molecules. Moreover, even if no immobilization of the possible cross-β structure binding compound or a protein comprising a cross-β structure is performed, separation of unbound and bound material is still possible. In such a case, use is, for example, made of a tagged possible cross-β structure binding compound. The tagged possible cross-β structure binding compound is contacted with a protein comprising a cross-β structure. After allowing binding between the two, use is made of a counterpart of the tag. Examples of suitable tags and counterparts are the His-tag and $Ni^{2+}$-NTA or biotin and streptavidin or glutathione S-transferase (GST) and glutathion or maltose binding protein and anti-maltose binding protein antibody or GST and anti-GST antibody. Specific antibodies directed to the possible cross-β structure binding compound are also useful in this respect. After, for example, contacting a His-tagged possible cross-β structure binding compound with a first protein comprising a cross-β structure, the material is contacted with $Ni^{2+}$-NTA (immobilized) beads and hence bound and unbound protein is subsequently separated.

In one of the embodiments, the activation of tPA, or a functional equivalent thereof, factor XII or a functional equivalent thereof, or a tPA or FXII-related protease or functional equivalent thereof, is part of a method according to the invention to select the compound with cross-β structure binding capacity. In a preferred embodiment thereof, the invention provides a method for selecting a compound capable of binding to a protein with cross-β structure, comprising contacting the compound with a first protein comprising a cross-β structure and allowing the compound and the protein to interact determining whether the compound at least in part binds to the cross-β structure selecting the compound that at least in part binds to the cross-β structure, wherein the determining step is an (enzymatic, preferably competitive) assay to determine the tPA-activating or factor XII-activating ability of the first protein in the presence of the compound. Absence or decreased presence of tPA or FXII activating ability shows that the compound is capable of binding a cross-β structure; the binding results ate least in partly blocking the availability of cross-β structures to tPA or FXII.

In a preferred embodiment, the invention provides a method wherein at least one of the determining steps is performed with an enzymatic assay. An example of such an assay is described in more detail. Such an enzymatic assay comprises the use of tPA and plasminogen and plasmin substrate, preferably S-2251 (Chromogenix Spa, Milan, Italy), in a suitable buffer, preferably the buffer is HBS (10 mM HEPES, 4 mM KCl, 137 mM NaCl, Ph 7.3). Such an assay further comprises a standard curve with a control with cross-β structure conformation and titration curve with a sample before and after a treatment/exposure to a putatively denaturing condition. In an alternative assay use is made of FXII with activated FXII substrate, preferably S-2222 or S-2302 in a suitable buffer; preferably, the buffer contains 50 mM, 1 mM EDTA, 0.001% v/v Triton-X100. Standard curves with known cross-β structure rich activators of FXII; preferably DXS500k with a protein; preferably the protein is endostatin or albumin; preferably with glycated hemoglobin, Aβ, amyloid fibrin peptide $NH_2$-148KRLEVDIDIGIRS160-COOH (SEQ ID NO:2) with K157G mutation. In yet another alternative assay use is made of FXII with prekallikrein and high molecular weight kininogen and either substrate Chromozym-PK for kallikrein or a substrate for activated FXII in a suitable buffer; preferably HBS. Standard curves with known cross-β structure rich activators of FXII; preferably DXS500k or kaolin with a protein; preferably the protein is endostatin or albumin; preferably with glycated hemoglobin, Aβ, amyloid fibrin peptide $NH_2$-148KRLEVDIDIGIRS160-COOH (SEQ ID NO:2) with K157G mutation.

There are thus multiple ways in which it can be established whether a possible/suspected cross-β structure binding compounds binds (or at least binds in part) to a protein comprising a cross-β structure. One can also, for example, include one or more samples of the protein of which it is established that it does not or hardly comprise cross-β structure. Preferably, these samples are the native conformation of the protein. If a possible compound binds to a protein comprising a cross-β structure but not to an identical type of protein essentially without a cross-β structure this can be a strong indication that the possible compound binds in a cross-β structure dependent way. This is, for example, established with separate binding studies or with competition assays, for example, by immobilizing the protein with cross-β structure and contacting it with a potential cross-β structure binding compound in the presence of a concentration series of the protein essentially without cross-β structure.

Another way to determine whether the possible cross-β structure binding compound at least in part binds a protein comprising a cross-β structure is via a competition assay wherein the competition assay is performed with a compound of which it is known or of which it is established (for example, with a method according of the invention) to have cross-β structure binding capabilities. In a preferred embodiment, the invention provides a method for selecting a compound capable of binding to a cross-β structure in a protein, comprising
- contacting the compound with a first protein comprising a cross-β structure and allowing the compound and the protein to interact
- determining whether the compound at least in part binds to the cross-β structure
- selecting the compound that at least in part binds to the cross-β structure, wherein the determining step is a competition assay between the compound, a first protein comprising a cross-β structure and at least one molecule selected from Table 1 or 2 or 3. In a preferred embodiment, an enzymatic competition assay is performed.

Yet another way to determine whether the possible cross-β structure binding compound at least in part binds a protein comprising a cross-β structure is via a competition assay wherein the competition assay is performed with a compound of which it is known or of which it is established (for example, with a method according of the invention) to have cross-β structure binding capabilities. In a preferred embodiment, the invention provides a method for selecting a compound capable of binding to a cross-β structure in a protein, comprising
- contacting the compound with a first protein comprising a cross-β structure and allowing the compound and the protein to interact
- determining whether the compound at least in part binds to the cross-β structure
- selecting the compound that at least in part binds to the cross-β structure, wherein the determining step is a competition tPA and/or factor XII activation assay.

The compounds listed in Table 1 and the proteins listed in Table 2 all bind to polypeptides with a non-native fold. In literature, this non-native fold has been designated as protein aggregates, amyloid, β-fibrils, amyloid oligomers, cross-β conformation, cross-β structure, cross-β spine, denatured protein, cross-β sheet, β-structure rich aggregates, infective aggregating form of a protein, unfolded protein, tangles, amyloid-like fold/conformation, (amyloid) plaques and other. We have disclosed that the common theme amongst all polypeptides with a non-native fold, that are ligands for one or more of the compounds listed in Tables 1 and 2, is the presence of a cross-β structure conformation.

The compounds listed in Tables 1 and 2 are considered to be only a subset of all compounds known today to bind to non-native protein conformations. The lists are thus non-limiting. More compounds are known today that bind to amyloid-like protein conformation. For example, in patent AU2003214375 it is described that aggregates of prion protein, amyloid, and tau bind selectively to polyionic binding agents such as dextran sulphate or pentosan (anionic), or to polyamine compounds such as poly(Diallyldimethylammonium Chloride) (cationic). Compounds with specificity for non-native folds of proteins listed in this patent and elsewhere are in principle equally suitable for methods and devices disclosed in this patent application. Moreover, also any compound or protein related to the ones listed in Tables 1 and 2 are covered by the claims. For example, point mutants, fragments, recombinantly produced combinations of cross-β structure binding domains and deletion- and insertion mutants are part of the set of compounds as long as they are capable of binding to a cross-β structure (i.e., as long as they are functional equivalents). Even more, also any newly discovered small molecule or protein that exhibits affinity for the cross-β structure fold can in principle be used in any one of the methods and applications disclosed herein.

The compounds listed in Table 3 are also considered to be part of the "Cross-β structure pathway," and this is based on literature data that indicates interactions of the listed molecules with compounds that likely comprise the cross-β structure but that have not been disclosed as such. For example, scavenger receptor MARCO binds to acetylated low-density lipoprotein and to bacteria. We showed that protein modifications, such as oxidation and glycation introduce the cross-β structure in proteins[1] and we pointed to a role for the amyloid core structures of bacteria in the interactions with a host.[5]

A competition assay based on the use of at least two or more than two of the above-mentioned compounds is also part of the invention, i.e., any combination of the compounds mentioned in Table 1 or 2 or 3 are also included herein.

Independent on which method is used to determine whether the possible cross-β structure binding compound at least in part binds to a protein comprising a cross-β structure, the compound of which it has been established that it at least binds to a cross-β structure of a protein is selected as a cross-β structure binding compound. Uses of such a compound will be discussed in more detail at a later point.

Besides a compound that is capable of binding to a cross-β structure in a protein or at least to a part thereof, the above outlined method is also used to select a binding compound that does not bind to the cross-β structure itself but to another structure in a protein which other structure is only present in a protein that comprises a cross-β structure and which other structure is absent if the protein does not comprise a cross-β structure. Such other structure is further referred to as a cross-β structure induced conformation. Hence, the invention also provides a method for selecting a compound capable of binding to a cross-β structure induced conformation in a protein comprising a cross-β structure, comprising
- contacting the compound with a first protein comprising a cross-β structure and allowing the compound and the protein to interact,
- determining whether the compound binds to a cross-β structure induced conformation
- selecting a compound that binds to a cross-β structure induced conformation.

The contacting step is performed, mutatis mutandis, as described above for a method for selecting a compound capable of binding to a cross-β structure in a protein. Separation of bound and unbound molecules and induction of a cross-β structure in a first protein are also optional steps. In this method, a competition assay as described earlier is used to confirm that binding does not occur at the cross-β structure. A cross-β structure induced conformation binding compound obtainable with such a method is also part of the invention as well as uses of such a cross-β structure induced conformation binding compound.

Moreover, the invention also provides a bi-specific cross-β structure binding compound obtainable with a method according to the invention. The term bi-specific includes a molecule capable of binding to a cross-β structure of a protein as well as capable of binding to any other sequence present in the protein.

As already outlined above, the first protein comprising a cross-β structure is, for example, a protein in solution, preferably obtained from an organism, preferably of an organism suffering from a protein misfolding disease/conformational disease/amyloidosis, and even more preferably the first protein comprising a cross-β structure is part of or obtained from a mammalian sample. Examples of useful samples, include but are not limited to a body fluid (for example, blood or lymph fluid, or cerebrospinal fluid or a part derived thereof (for example, plasma)), or samples from tissues or cells which samples are optionally homogenized. It is clear for a person skilled in the art that the protein or a set of proteins can be directly applied in a method of the invention, but the nature, i.e., amino acid composition, of the protein or set of proteins can also be identified by proteomics, including mass spectrometry. Subsequently, the protein can be chemically synthesized or recombinantly expressed in vitro or in any cell, cell-based culture or organism and used for one of the embodiments of the present invention.

It is already clear from the compounds in Table 1 or 2 or 3 that the compound binding a protein comprising cross-β structure (binding to a cross-β structure or binding to a cross-β structure induced conformation) can be of diverse nature; it is, for example, a protein (for example, an antibody or a functional fragment and/or a functional equivalent thereof), or a (small) chemical compound. In a preferred embodiment, the compound is derived from a library, preferably from a recombinant protein library or a small compound library or an antibody library or from a phage display library or from the B-cells of an immunized animal or a hybridoma collection or a quadridoma collection. Hence, a method according to the invention is suitable for large-scale or high-throughput screening.

As already mentioned, the first protein comprising a cross-β structure is optionally immobilized on a carrier. In another embodiment, the first protein comprising a cross-β structure is provided with a label to, for example, facilitate identification. Examples of suitable labels are Universal Linkage System (ULS™), maltose binding protein, glutathione S-transferase (GST), secreted human placental alkaline phosphatase (SEAP), His-tag, biotin, green fluorescent protein, (horse radish) peroxidase, FLAG, myc, VSV. Immobilization and labeling of the cross-β structure binding compound is also possible.

In another embodiment, the invention provides a method for selecting a compound capable of binding a protein comprising a cross-β structure conformation comprising
contacting the compound with a first protein comprising a cross-β structure and allowing the compound and the protein to interact
determining whether the compound at least in part binds to the protein comprising a cross-β structure
selecting the compound that at least in part binds to the protein comprising a cross-β structure, further comprising performing a subtraction or inhibition assay with a second protein comprising a cross-β structure and selecting the compound that specifically binds to the first protein. In addition, selecting the compound that at least in part binds to the compound with cross-β structure, further comprising performing binding assays with a series of different compounds comprising a cross-β structure and selecting the compound that specifically binds to the first protein.

With this method a cross-β structure comprising protein binding compound specific for the first compound is selected. Preferably multiple second proteins are tested to improve/establish the selectivity of the cross-β structure binding compound for the first protein. Such a specific compound is extremely useful for diagnostic and therapeutic application and will be discussed in more detail below.

A cross-β structure binding compound or a cross-β structure induced conformation binding compound or a bi-specific binding compound obtainable according to a method of the invention is also included herein. Some useful applications of such a binding molecules are described and include, but are not limited to, detecting the presence of cross-β structure comprising proteins, inhibition of the formation of cross-β structure conformation, inhibition of the formation of amyloid fibrils, modulating cross-β structures induced toxicity and removal of cross-β structure containing molecules from any given sample or from the circulation of a mammal. For example, the compound is coupled to a dialysis device that facilitates the removal of cross-β structure comprising proteins from any given sample or the circulation of a mammal. Such a sample can, for example, be a solution containing proteins, preferably purified proteins, more preferably proteins that are produced recombinantly, and even more preferably proteins that are prepared for use as therapeutics for the treatment of a mammal.

A cross-β structure binding compound or a cross-β structure induced conformation binding compound obtainable according to a method of the invention provides methods for the detection or treatment of diseases associated with the formation of cross-β structure, such as, but not limited to, amyloidosis and include Alzheimer's disease (AD), light-chain amyloidosis, type II diabetes and spongiform encephalopathies.

A cross-β structure binding compound or a cross-β structure induced conformation binding compound obtainable according to a method of the invention is useful in methods to detect a compound with cross-β structure. In one embodiment, such a binding compound is bound or affixed to a solid surface, preferably a microtiter plate or preferably a chip of a surface plasmon resonance apparatus. The solid surfaces useful in this embodiment would be known to one of skill in the art. For example, one embodiment of a solid surface is a bead, a column, a plastic or polymer dish, a plastic or polymer plate, a microscope slide, a nylon membrane, etc. (After blocking) the surface is incubated with a sample. (After removal of unbound sample) bound molecules comprising the cross-β structure are subsequently detected using a second cross-β structure binding compound, preferably an anti-cross-β structure antibody or a molecule containing a finger module. The second cross-β structure compound is bound to a label, preferably an enzyme, such as peroxidase. The detectable label may also be a fluorescent label, biotin, digoxigenin, a His-tag, a SEAP tag, a Myc tag, a VSV tag, an MPB tag, a GST tag, a radioactive atom, a paramagnetic ion, or a chemiluminescent label. It may also be labeled by covalent means such as chemical, enzymatic or other appropriate means with a moiety such as an enzyme or radioisotope. Portions of the above mentioned compounds of the invention may be labeled by association with a detectable marker substance, preferably radiolabeled with $^{125}$I or biotin to provide reagents useful in detection and quantification of compound or its receptor bearing cells or its derivatives in solid tissue and fluid samples such as blood, cerebral spinal fluid, urine or other. Such samples may also include serum used for tissue culture or medium used for tissue culture.

In another embodiment, the solid surface can be microspheres for, for example, agglutination tests.

In one embodiment, a cross-β structure binding compound or a cross-structure induced conformation binding compound is used to stain tissue samples. Preferably the compound is fused to a protein or peptide suitable for detection, such as GST. Alternatively, the compound is coupled directly to a convenient label. The detectable label may be a fluorescent label, a biotin, a digoxigenin, a radioactive atom, a paramagnetic ion, and a chemiluminescent label. It may also be labeled by covalent means such as chemical, enzymatic or other appropriate means with a moiety such as an enzyme or radioisotope. Portions of the above mentioned compounds of the invention may be labeled by association with a detectable marker substance (e.g., radiolabeled with $^{125}I$ $^{99m}TC$, $^{131}I$, chelated radiolabels, or biotin) to provide reagents useful in detection and quantification of compound or its receptor bearing cells or its derivatives in solid tissue and fluid samples such as blood or cerebral spinal fluid or urine. The cross-β structure binding compound or the cross-β structure induced conformation binding compound is incubated with the sample and after washing visualized with antibodies directed against the fused protein or polypeptide, preferably GST.

In one of the embodiments, the above sample is obtained from tissue from patients with or expected to suffer from a conformational disease. Alternatively, the tissue is derived from animals or from cells cultured in vitro.

A cross-β structure binding compound or a cross-β structure induced conformation binding compound obtainable according to a method of the invention is also useful as part of a new diagnostic tool. Such use is particular useful for diagnostic identification of conformational diseases or diseases associated with amyloid formation, like AD or diabetes. It is clear that this diagnostic use is also useful for other diseases and processes which involve cross-β structure formation, like all amyloidosis type diseases, atherosclerosis, diabetes, bleeding, thrombosis, renal failure with kidney dialysis regime, multiple myeloma, lymphoma or sepsis and complications thereof, such as disseminated intravascular coagulation (DIC). For example, one can use the obtained cross-β structure binding compound and provide it with a label, such as, but not limited to a radiolabel, such as $^{125}I$ or a fluorescent label. This labeled cross-β structure binding compound can then be used either in vitro or in vivo for the detection of cross-β structure comprising proteins, hence for determining the presence of apoptotic cells, a plaque, a protein deposition, an occlusion in the circulation, a thrombus or a lesion or a necrotic area involved in a conformational disease. One can, for example, use an ELISA assay to determine the amount of sepsis in a patient or one can localize a plaque involved in a conformational disease by administration into, preferably the circulation of, a mammal of the identified cross-β structure binding and labeled compound.

In another embodiment, this invention provides a method for inhibiting the formation of protein aggregation and the formation of amyloid fibrils or to modulate cross-β structure induced effects, including, cell toxicity, inflammatory responses, immunogenicity, fibrinolytic activity or thrombogenicity, including activation of platelets. The inhibition of protein aggregation and/or amyloid formation preferably has the consequence of decreasing the load of protein aggregates and/or fibrils. Inhibition is not restricted to amyloid fibrils, and besides protein aggregates includes any other appearance of the cross-β structure fold, for example, also in soluble oligomers.

The inhibition of cross-β structure comprising oligomers, protein aggregation, amyloid fibril formation or modulating cross-β structure mediated cell toxicity, inflammation, immunogenicity, fibrinolytic activity or thrombogenicity, including platelet activation may also have the consequence of modulating cell death. The cell can be any cell, but preferably is a neuronal cell, an endothelial cell, a platelet, a renal cell, a liver cell, a macrophage or a tumor cell. The cell can be a human cell or a cell from any other organism.

The cell may typically be present in a subject. The subject to which the cross-β structure binding compound is administered may be a mammal and preferably a human.

The subject may be suffering from amyloidoses, from another conformational disease, from prion disease, from chronic renal failure and/or dialysis related amyloidosis, from atherosclerosis, from cardiovascular disease, from autoimmune disease, from multi organ dysfunction syndrome (MODS) or the subject may be obese. The diseases which may be treated or prevented with the methods of the present invention include, but are not limited to, diabetes, Alzheimer's disease, senility, renal failure, hyperlipidemea atherosclerosis, neuronal cytotoxicity, Down's syndrome, dementia associated with head trauma, amyotrophic lateral sclerosis, multiple sclerosis, amyloidosis, male impotence, wound healing, periodontal disease, neuropathy, retinopathy, nephropathy or neuronal degeneration.

The administration of a cross-β structure binding compound or a cross-β structure induced conformation binding compound obtainable by a method according to the invention may be constant or for a certain period of time. The compound may be delivered hourly, daily, weekly, monthly (e.g., in a time release form) or as a one-time delivery (bolus delivery). The delivery may also be continuous, e.g., intravenous delivery. In a preferred embodiment, the invention provides a pharmaceutical composition comprising a compound capable of binding to a protein with cross-β structure obtainable by the method according to the invention. Even more preferably, the compound is selected for its specificity, i.e., it binds to a first protein comprising a cross-β structure but not (or hardly not) to another type (second or third (and so on)) of protein that also comprises a cross-β structure. In yet another preferred embodiment, the invention provides use of a cross-β structure binding compound in the preparation of a medicament for the treatment of a cross-β structure related disease.

A carrier may be used. The carrier may be a diluent, an aerosol, an aqueous solution, a nonaqueous solution or a solid carrier. This invention also provides pharmaceutical compositions including therapeutically effective amounts of a cross-β structure binding compound, together with suitable diluents, preservatives, solubilizers, emulsifiers, adjuvants and/or carriers. Such compositions may be liquids or lyophilized or otherwise dried formulations and include diluents of various buffer content (e.g., Tris-HCl., acetate, phosphate, carbonate, ammonium), pH and ionic strength, additives such as albumin or gelatin to prevent absorption to surfaces, detergents (e.g., TWEEN®20, TWEEN®80, Pluronic F68, bile acid salts), solubilizing agents (e.g., glycerol, polyethylene glycerol), antioxidants (e.g., ascorbic acid, sodium metabisulfite), preservatives (e.g., Thimerosal, benzyl alcohol, methylhydroxybenzoate, parabens, m-cresol), bulking substances or tonicity modifiers (e.g., lactose, mannitol), covalent attachment of polymers such as polyethylene glycol to the compound, in complex with metal ions, or incorporation of the compound into or onto particulate preparations of polymeric compounds such as polylactic acid, polglycolic acid, hydrogels, etc, or onto liposomes, micro emulsions, micelles, unilamellar or multi-lamellar vesicles, erythrocyte ghosts, or spheroplasts.

The administration of a cross-β structure binding compound obtainable by a method according to the invention may comprise intralesional, intraperitoneal, intramuscular, subcutaneous or intravenous injection; infusion; liposome-mediated delivery; topical, intrathecal, gingival pocket, per rectum, intrabronchial, nasal, oral, otic or ocular delivery. In a further embodiment, the administration includes intrabronchial administration, anal, intrathecal administration or transdermal delivery.

According to the invention, the cross-β structure binding compound may be administered hourly, daily, weekly, monthly or annually. In another embodiment, the effective amount of the cross-β structure binding compound comprises from about 0.000001 mg/kg body weight to about 1000 mg/kg body weight.

The cross-β structure binding compound obtainable with a method according to the invention may be delivered locally via a capsule which allows sustained release of the agent over a period of time. Controlled or sustained release compositions include formulation in lipophilic depots (e.g., fatty acids, waxes, oils). Also included in the invention are particulate compositions coated with polymers (e.g., poloxamers or poloxamines) and the cross-β structure binding compound coupled to antibodies directed against tissue-specific receptors, ligands or antigens or coupled to ligands of tissue-specific receptors. Other embodiments of the cross-β structure binding compound incorporate particulate forms of protective coatings, protease inhibitors or permeation enhancers for various routes of administration, including parenteral, pulmonary, nasal and oral.

The effective amount of the cross-β structure binding compound preferably comprise 1 ng/kg body weight to about 1 gr/kg body weight. The actual effective amount will be based upon the size of the cross-β structure binding compound and its properties.

The invention provides the use of a cross-β structure binding compound or a cross-β structure induced conformation binding compound for the detection and removal of compounds with cross-β structures. The compound is preferably a cross-β structure binding molecule, more preferably a protein and/or a functional equivalent and/or a functional fragment thereof. It is clear that the invention also comprises antibodies that bind proteins with cross-β structures. Examples of suitable antibodies are camel and lama antibodies. In another preferred embodiment, the protein is an antibody and/or a functional equivalent and/or a functional fragment thereof. With this use, the invention provides, for example, a therapeutic method to remove cross-β structure comprising proteins from, for example, the circulation, preferably via extracorporeal dialysis. For example, a patient with sepsis is subjected to such use by dialysis of blood of the patient through means which are provided with, for example, preferably immobilized, cross-β structure binding compounds of the invention. One could, for example, couple the cross-β structure binding compounds to a solid surface or to the inside of the tubes used for dialysis. In this way, all cross-β structure comprising proteins will be removed from the blood stream of the patient, thereby relieving the patients of the negative effects caused by the cross-β structure comprising proteins.

In another embodiment, the present invention discloses a composition comprising a compound capable of binding to a cross-β structure in a protein obtainable by a method of the invention or a compound capable of binding to a cross-β structure induced in a protein.

In yet another embodiment, the invention discloses a pharmaceutical composition comprising a compound capable of binding to a cross-β structure in a protein obtainable by a method of the invention or a compound capable of binding to a cross-β structure induced in a protein.

As described, the invention provides a method for at least partly removing from a solution a protein comprising a cross-β structure comprising contacting a compound capable of binding to a protein with cross-β structure obtainable by the method according to the invention with the solution and removing the resulting complex of the protein with cross-β structure and the compound from the solution.

In another embodiment, the invention provides the use of a compound capable of binding to a cross-β structure in a protein, the compound obtainable by a method of the invention or a compound capable of binding to a cross-β structure induced conformation in a protein, the compound obtainable by the method of any one of claims 2 to 8 for detection of a cross-β structure in a protein.

Upon selection of a cross-β structure binding compound, the invention further provides a method for selecting an inhibitor that is capable of at least partly blocking the binding of a selected cross-β structure binding compound and a protein comprising a cross-β structure, comprising contacting a selected cross-β structure binding compound with a first protein comprising a cross-β structure in the presence of the inhibitor and allowing the compound and the protein to interact determining whether the compound at least in part binds to the cross-β structure selecting the inhibitor that at least in part prevents the binding of the cross-β structure binding compound to the protein.

Upon selection of a cross-β structure binding compound the invention further provides a method for selecting a binding molecule capable of binding to a selected cross-β structure binding compound, comprising contacting the selected cross-β structure binding compound with a binding molecule suspected to be capable of binding to the cross-β structure binding compound and allowing the compound and binding molecule to interact determining whether the binding molecule at least in part binds to the compound selecting the binding molecule that at least in part binds to the compound.

The invention further provides use of a compound capable of binding to a cross-β structure in a protein or a compound capable of binding to a cross-β structure induced conformation in a protein obtainable by the method of the invention for diagnostics.

The invention will be explained in more detail in the following examples, which is not limiting the invention.

DESCRIPTION OF THE DRAWINGS

FIG. 1: Monoclonal antibodies elicited against amyloid Aβ, chicken serum amyloid A and glycated hemoglobin bind to various polypeptide aggregates with cross-β structure conformation, but without amino acid homology. Hybridoma cell culture supernatants are brought into wells of ELISA plates with coated buffer ($H_2O$, "no coat Greiner") or with immobilized antigens with cross-β structure conformation, used for immunization (Aβ(1-40) E22Q and Hb-AGE), and used as unrelated ligand for putative anti-cross-β structure-dependent antibodies (amyloid human γ-globulins and amyloid FP13 K157G). Freshly dissolved and centrifuged Aβ, FP13 K157G, control Hb and γ-globulins were immobilized as negative control, as well as PBS ("no coat Exiqon"), as shown for clone 7H1. Aggregates with cross-β structure conformation were air-dried onto Greiner microlon high-binding plates. Freshly prepared non-amyloid controls were coated on Exiqon Immobilizer plates. Fresh culture medium with 10% FCS was used as a negative control. Signals obtained with the indicated clones are given as multiples of the signals obtained with fresh culture medium (buffer). When antibody binding to buffer-coated wells exceeds background levels of 1.00 (i.e., more signal than with control culture medium), a dashed line marks the actual ratio. Clone 7H1 was tested in single wells on each antigen and on non-amyloid controls, whereas clones 2E2, 4F4, 7H2, 7H9 and 8F2 were tested in duplicate, in pre-blocked wells, on amyloid antigens only. A. Clone 2E2, B. Clone 4F4, C. Clone 7H1, D. 7H2, E. 7H9, and F. Clone 8F2. G-J. Monoclonal 7H2 shows selectivity for human γ-globulins with cross-β structure conformation. G. An ELISA with coated buffer and polypeptides with (Aβ, amyloid FP13 K157G, Hb-AGE, albumin-AGE, amyloid γ-globulins) and without (FP10 (SEQ ID NO:3), albumin, Hb, γ-globulins, freshly dissolved FP13 K157G, freshly dissolved Aβ) cross-β structure conformation, and undiluted control medium and cell culture medium with 7H2 IgM, showing that 7H2 preferentially binds to amyloid γ-globulins. H. ELISA with a dilution series of hybridoma clone 7H2H2 and immobilized amyloid γ-globulins, acid-denatured γ-globulins, base-denatured γ-globulins and freshly prepared native γ-globulins. Cell culture medium with 7H2H2 IgM was used undiluted and diluted 2/4/8/16/32/64/128/256/512/1024 times. I. Undiluted cell culture medium with 7H2 subclones was tested on immobilized antigens Aβ and Hb-AGE, as well as on unrelated amyloid-like structure conformations amyloid γ-globulins and FP13 K157G. All five subclones show similar preferential binding to amyloid γ-globulins. J. Binding of 100 times diluted cell culture medium with 7H2H2 IgM was tested with γ-globulins treated in various ways as indicated. In addition to amyloid γ-globulins, 7H2H2 binds to base-denatured γ-globulins. K. ELISA with immobilized amyloid γ-globulins showing that binding of 7H2H2 from 10 times diluted culture medium is inhibited by Congo red concentrations of higher than 5 µM. L-N. Detection of amyloid-like conformation in γ-globulins preparations. Like standard amyloid γ-globulins, acid- and base-natured γ-globulins test positive in Congo red (L.) and ThT (M.) fluorescence assays, and in the Plg-activation assay (N.). O. ELISA showing binding of monoclonal 7H2H2 to immobilized amyloid γ-globulins in the presence of concentration series of freshly dissolved-, base-denatured-, acid-denatured and the coated antigen amyloid γ-globulins.

FIG. 12: Binding of tPA to misfolded ovalbumin after pre-incubation of immobilized misfolded ovalbumin with an indicated selection of small compounds at 500 μg/ml.

DETAILED DESCRIPTION OF THE INVENTION

Tables

TABLE 1 cross-β structure binding compounds

Figure 2:
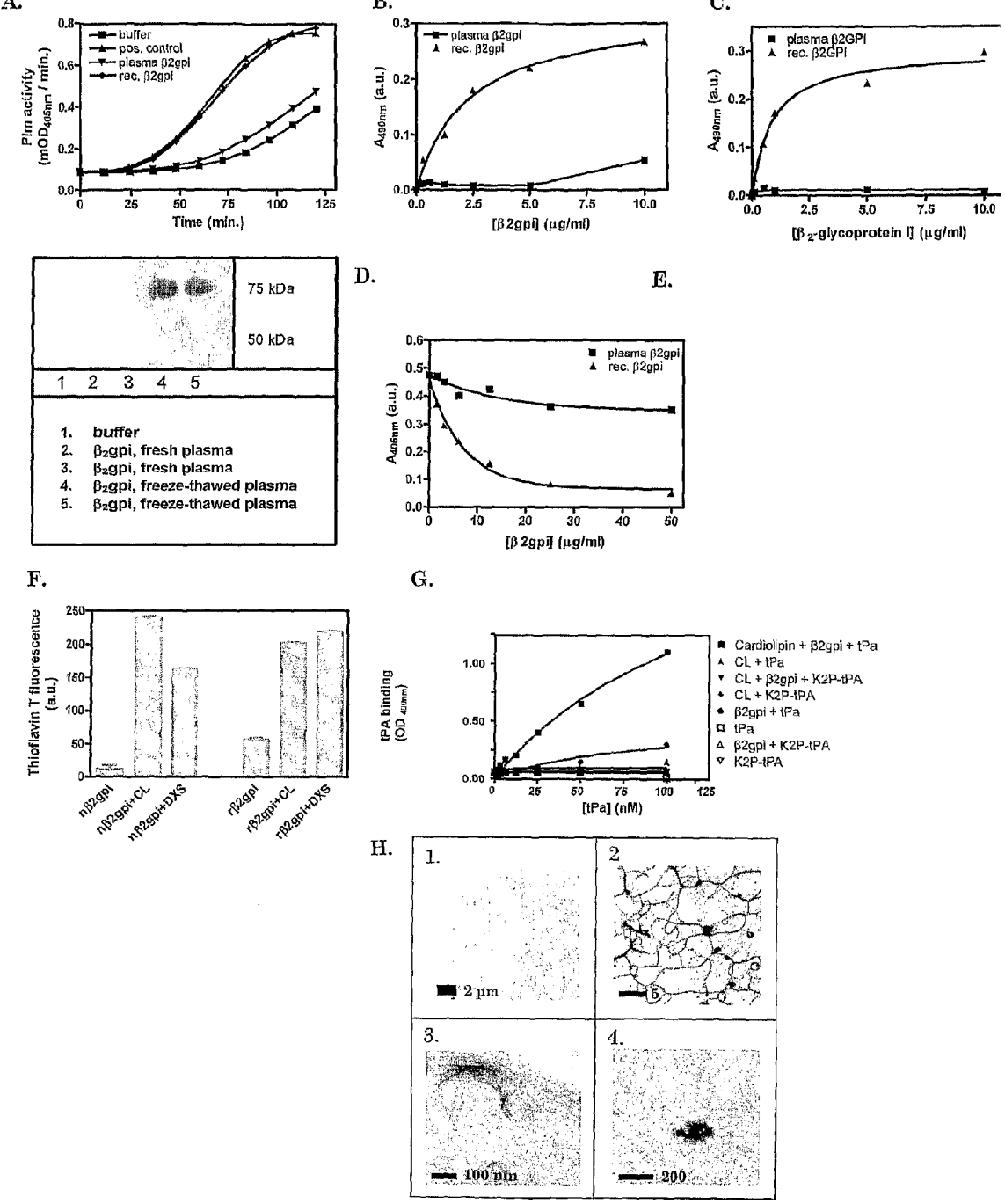
FIG. 2: Binding of factor XII and tPA to β₂-glycoprotein I and binding of anti-β₂GPI auto-antibodies to recombinant β₂GPI. A. Plg-activation assay showing the stimulatory activity of recombinant β₂GPI on the tPA-mediated conversion of Plg to plasmin. The positive control was amyloid fibrin peptide FP13. B. In an ELISA, recombinant β₂GPI binds to immobilized tPA, whereas β₂GPI purified from plasma does not bind. The $k_D$ is 2.3 µg ml$^{-1}$ (51 nM). C. In an ELISA, factor XII binds to purified recombinant human β₂GPI, and not to β₂GPI that is purified from human plasma, when purified factor XII is immobilized onto ELISA plate wells. Recombinant β₂GPI binds with a $k_D$ of 0.9 (20 nM) to immobilized factor XII. D. Western blot incubated with anti-human factor XII antibody. The β₂GPI was purified either from fresh human plasma or from plasma that was frozen at −20° C. and subsequently thawed before purification on a β₂GPI affinity column. Eluted fractions are analyzed on Western blot after SDS-PA electrophoresis. When comparing lanes 2-3 with 4-5, it is shown that freezing-thawing of plasma results in co-purification of factor XII together with the β₂GPI. The molecular mass of factor XII is 80 kDa. E. In an ELISA, recombinant β₂GPI efficiently inhibits binding of anti-β₂GPI auto-antibodies to immobilized β₂GPI, whereas plasma β₂GPI has a minor effect on antibody binding. Anti-β₂GPI auto-antibodies were purified from plasma of patients with the autoimmune disease Anti-phospholipid syndrome. F. Exposure of 25 µg ml$^{-1}$ β₂GPI, recombinantly produced (rβ₂GPI) or purified from plasma (nβ₂GPI), to 100 µM CL vesicles or to 250 µg ml$^{-1}$ DXS500k induces an increased fluorescence of ThT, suggestive for an increase in the amount of cross-β structure conformation in solution. Signals are corrected for background fluorescence of CL, DXS500K, ThT and buffer. G. Binding of tPA and K2P-tPA to β₂GPI immobilized on the wells of an ELISA plate, or to β₂GPI bound to immobilized CL is assessed. β₂GPI contacted to CL binds tPA to a higher extent than β₂GPI contacted to the ELISA plate directly. K2P-tPA does not bind to β₂GPI. TPA does not bind to immobilized CL. H. Transmission electron microscopy images of 400 µg ml$^{-1}$ purified plasma β2GPI alone (1) or contacted with 100 µM CL (2, 3) and of 400 µg ml$^{-1}$ purified recombinant β2GPI (4).

| | | |
|---|---|---|
| Congo red | Chrysamine G | Thioflavin T |
| 2-(4'-(methylamino)phenyl)-6-methylbenzothiaziole | Any other amyloid-binding dye/chemical | Glycosaminoglycans |
| Thioflavin S | Styryl dyes | BTA-1 |
| Poly(thiophene acetic acid) | conjugated polyeclectrolyte PTAA-Li | |

TABLE 2

Proteins that bind to and/or interact with misfolded proteins and/or with proteins comprising cross-β structure

| | | |
|---|---|---|
| Tissue-type plasminogen activator | Finger domain(s) of tPA, factor XII, fibronectin, HGFA | Apolipoprotein E |
| Factor XII | Plasmin(ogen) | Matrix metalloprotease-1 |
| Fibronectin | 75 kD-neurotrophin receptor (p75NTR) | Matrix metalloprotease-2 |
| Hepatocyte growth factor activator | α2-macroglobulin | Matrix metalloprotease-3 |
| Serum amyloid P component | High molecular weight kininogen | Monoclonal antibody 2C11(F8A6)[‡] |
| C1q | Cathepsin K | Monoclonal antibody 4A6(A7)[‡] |
| CD36 | Matrix metalloprotease 9 | Monoclonal antibody 2E2(B3)[‡] |
| Receptor for advanced glycation endproducts | Haem oxygenase-1 | Monoclonal antibody 7H1(C6)[‡] |
| Scavenger receptor-A | low-density lipoprotein receptor-related protein (LRP, CD91) | Monoclonal antibody 7H2(H2)[‡] |
| Scavenger receptor-B | DnaK | Monoclonal antibody 7H9(B9)[‡] |
| ER chaperone Erp57 | GroEL | Monoclonal antibody 8F2(G7)[‡] |
| Calreticulin | VEGF165 | Monoclonal antibody 4F4[‡] |
| Monoclonal conformational antibody WO1 (ref. (O'Nuallain and Wetzel, 2002)) | Monoclonal conformational antibody WO2 (ref. (O'Nuallain and Wetzel, 2002)) | Amyloid oligomer specific antibody (ref. (Kayed et al., 2003)) |
| formyl peptide receptor-like 1 | α(6)β(1)-integrin | CD47 |
| Rabbit anti-albumin-AGE antibody, Aβ-purified[a)] | CD40 | apo A-I belonging to small high-density lipoproteins |
| apoJ/clusterin | 10 times molar excess PPACK, 10 mM εACA, (100 pM-500 nM) tPA[2)] | CD40-ligand |
| macrophage scavenger receptor CD163 | broad spectrum (human) immunoglobulin G (IgG) antibodies (IgIV, IVIg) | BiP/grp78 |
| Erdj3 | haptoglobin | |

[‡]Monoclonal antibodies developed in collaboration with the ABC-Hybridoma Facility, Utrecht University, Utrecht, The Netherlands.
[a)]Antigen albumin-AGE and ligand Aβ were send in to Davids Biotechnologie (Regensburg, Germany); a rabbit was immunized with albumin-AGE, antibodies against a structural epitope were affinity purified using a column with immobilized Aβ.
[2)]PPACK is Phe-Pro-Arg-chloromethylketone (SEQ-ID 8), εACA is ε-amino caproic acid, tPA is tissue-type plasminogen activator

TABLE 3

| Proteins involved in the "crossbeta structure pathway" | | |
|---|---|---|
| Monoclonal antibody 4B5 | Heat shock protein 27 | Heat shock protein 40 |
| Monoclonal antibody 3H7‡ | Nod2 (=CARD15) | Heat shock protein 70 |
| FEEL-1 | Pentraxin-3 | HDT1 |
| LOX-1 | Serum amyloid A proteins | GroES |
| MD2 | Stabilin-1 | Heat shock protein 90 |
| FEEL-2 | Stabilin-2 | CD36 and LIMPII analogous-I (CLA-1) |
| Low Density Lipoprotein | LPS binding protein | CD14 |
| C reactive protein | CD45 | Orosomucoid |
| Integrins | alpha-1 antitrypsin | apo A-IV-Transthyretin complex |
| Albumin | Alpha-1 acid glycoprotein | β2-glycoprotein I |
| Lysozyme | Lactoferrin | Megalin |
| Tamm-Horsfall protein | Apolipoprotein E3 | Apolipoprotein E4 |
| Toll-like receptors | Complement receptor CD11b/CD18 (Mac-1, CR3) | CD11d/CD18 (subunit aD) |
| CD11b2 | CD11a/CD18 (LFA-1, subunit aL) | CD11c/CD18 (CR4, subunit aX) |
| Von Willebrand factor | Myosin | Agrin |
| Perlecan | Chaperone60 | b2 integrin subunit |
| proteins that act in the unfolded protein response (UPR) pathway of the endoplasmic reticulum (ER) of prokaryotic and eukaryotic cells | proteins that act in the endoplasmic reticulum stress response (ESR) pathway of prokaryotic and eukaryotic cells | Macrophage receptor with collagenous structure (MARCO) |
| 20S | CHAPERONE16 family members | HSC73 |
| HSC70 | translocation channel protein Sec61p | 26S proteasome |
| 19S cap of the proteasome (PA700) | UDP-glucose:glycoprotein glucosyl transferase (UGGT) | carboxy-terminus of CHAPERONE70-interacting protein (CHIP) |
| Pattern Recognition Receptors | Derlin-1 | Calnexin |
| Bcl-2 asociated athanogene (Bag-1) | GRP94 | Endoplasmic reticulum p72 |
| (broad spectrum) (human) immunoglobulin M (IgM) antibodies | proteins that act in the endoplasmic reticulum associated degradation system (ERAD) | The (very) low density lipoprotein receptor family |
| Fc receptor | | |

‡Monoclonal antibodies developed in collaboration with the ABC-Hybridoma Facility, Utrecht University, Utrecht, The Netherlands.

EXPERIMENTAL PART

Materials, Methods and Results

Example 1

Monoclonal Antibodies Bind Specifically to Peptide and Protein Aggregates with Amyloid-Like Cross-β Structure Conformation Methods: Preparation of Hybridomas that Produce Anti-Cross-β Structure Antibodies Before immunization of a mouse, preparations of amyloid-β peptide 1-40 Dutch type, with mutation E22Q (Aβ), fibrin peptide KRLEVDIDIGIRS (FP13 K157G) (SEQ ID NO:2), fibrin peptide IDIKIR (FP6) (SEQ ID NO:4) (all from the Peptide Synthesis Facility, Netherlands Cancer Institute NKI, Amsterdam, The Netherlands), glycated hemoglobin (Hb-AGE) and γ-globulins (G4386, Sigma, Zwijndrecht, The Netherlands) were tested for the presence of cross-β structure conformation. Lyophilized Aβ, FP13 K157G, FP6 and human γ-globulins were dissolved at 10 mg ml$^{-1}$ in 1,1,1,6,6,6-hexafluoro-2-propanol and trifluoroacetic acid in a 1:1 volume ratio. Solvent was evaporated under an air stream and the polypeptides were dissolved in H$_2$O. Aβ and FP6 at 10 mg ml$^{-1}$, FP13 K157G at 2 mg ml$^{-1}$ and γ-globulins at 1 mg ml$^{-1}$. Aβ and γ-globulins were incubated for 72 hours at 37° C. or at room temperature, and afterwards stored at room temperature or at −20° C., respectively. FP6 and FP13 K157G were kept at room temperature. Hb-AGE was prepared by incubating hemoglobin (Hb, 5 mg ml$^{-1}$, Sigma-Aldrich, H7379) for 32 weeks at 37° C. with PBS containing 1 M of glucose-6-phosphate (g6p, Sigma-Aldrich, G7250) and 0.05% m/v of NaN$_3$. In control solutions, g6p was omitted. After incubations, solutions were extensively dialyzed against distilled water and, subsequently, stored at 4° C. Protein concentrations were determined with Advanced protein-assay reagent ADV01 (Cytoskeleton, Denver, Colo., USA). Glycation and formation of advanced glycation end-products (AGE) was confirmed by measuring intrinsic fluorescent signals from advanced glycation end-products; excitation wavelength 380 nm, emission wavelength 435 nm. In addition, binding of AGE-specific antibodies was determined by ELISA, as described.[1] Presence of cross-β structure conformation in Hb-AGE was confirmed by tPA binding, circular dichroism spectropolarimetry analyses, transmission electron microscopy (TEM) imaging of fibrillar structure conformations and by Congo red fluorescence measurements (not shown). Presence of cross-β structure conformation in FP13 K157G was confirmed by Congo red fluorescence, ThT fluorescence, TEM imaging, X-ray diffraction analysis, tPA binding, and tPA- and factor XII activation assays. FP6, γ-globulins and Aβ were analyzed with Congo red fluorescence assay, ThT fluorescence assay, tPA binding ELISA, tPA activation assay and TEM imaging (not shown). In addition, presence of multimers with cross-β structure conformation in FP6 was confirmed by X-ray diffraction analysis.

The immunizations were performed by the ABC-Hybridoma facility (Utrecht University, The Netherlands). A mouse (Balb/c) was immunized with 100 µg Aβ in 100 µl H$_2$O and 100 µl complete Freund's adjuvant. After three weeks, a first boost of 50 µg Aβ in H$_2$O-Specol (ID-DLO, Lelystad, The Netherlands) was given, followed by a second boost 30 days after the first boost. Thirty-six and 37 days after the second boost, the mouse was given two additional boosts with 50 µg Aβ in PBS (intravenously). Forty-nine weeks later, the mouse was immunized with 50 µg chicken serum amyloid A in H$_2$O-Specol. Four weeks later, the mouse was immunized with 50 µg Hb-AGE. Finally, 31 and 32 days later the mouse was boosted twice intravenously with 50 µg FP6 in PBS. Three days after the final boost, the mouse was sacrificed and the spleen was used to prepare hybridomas.

Hybridomas were screened for production of anti-cross-β structure antibodies. First, 768 clones in 96-well plates were screened for the presence of antibodies that bind to immobilized FP13 K157G amyloid and amyloid γ-globulins. For this purpose, FP13 K157G and amyloid γ-globulins were diluted together in H$_2$O to 5 µg ml$^{-1}$ of each polypeptide. Microlon high-binding ELISA plates (Greiner, Bio-One GmbH, Frickenhausen, Germany) were filled with 50 µl of this solution and air-dried overnight at 37° C. Plates were blocked with Blocking reagent (catalogue #11112589001, Roche Applied Science, Basel, Switzerland) and washed with tap water. One hundred µl of hybridoma cell culture supernatants containing 10% v/v fetal calf serum was transferred to the coated plates and incubated for 1 hour at room temperature (RT) while shaking. Plates were washed with Tris-buffered saline pH 7.3 (TBS) with 0.1% TWEEN®20 (wash buffer), and subsequently overlayed with 2000× diluted peroxidase-coupled rabbit anti-mouse immunoglobulins (RAMPO, #P0260, DAKO, Denmark) in PBS/0.1% TWEEN®20 for 30 minutes at RT while shaking. After extensive washing, bound RAMPO was visualized with tetramethylbenzidine (TMB, #45.01.20/#45.014.01, Biosource, Nivelles, Belgium). The reaction was stopped after 5 minutes with 1% H$_2$SO$_4$ in H$_2$O. Plates were read at 450 nm. Clones were included in further screening trials when signals reached at least 1.5× background levels. Again, presence of putative anti-cross-β structure antibodies was analyzed with immobilized FP13 K157G and amyloid γ-globulins. Then, 35 clones remained positive. Those clones were transferred to cell culture flasks and subjected to further analyses. For this purpose, again FP13 K157G and amyloid γ-globulins, now separately, as well as Aβ and Hb-AGE were immobilized on ELISA plates. In addition, freshly dissolved Aβ, FP13 K157G, Hb and γ-globulins were coated onto Immobilizer plates (Exiqon, Vedbæk, Denmark). These freshly dissolved controls were coated at 20, 12.5, 50 and 50 µg ml$^{-1}$, respectively, in PBS, for 1 hour at RT while shaking. Aβ, FP13 K157G, Hb and γ-globulins stock solutions of 20, 12.5, 50 and 50 µg ml$^{-1}$, respectively, were first centrifuged for 30 minutes at 238*10$^3$×g to remove insoluble aggregates that might be present. Buffer was coated on Greiner (H$_2$O) and on Exiqon (PBS) plates as additional negative control. Greiner plates were not blocked during initial screens with 768 clones. Ten % FCS in the cell culture medium is an efficient blocker during the incubation of cell supernatant in the ELISA plates. Ten µl of PBS/1% TWEEN®20 was added to the wells of the Exiqon plates, before cell supernatants were added. TWEEN®20 at a concentration of 0.1% is an effective instant blocker for Immobilizer plates. Hundred µl of the hybridoma supernatants was transferred to the plates. Culture medium was used as negative control. Signals were calculated as multiples of the signals obtained when fresh culture medium with 10% FCS was incubated on the various immobilized antigens and controls. Signals were considered positive when exceeding 2.0× the background values obtained with fresh culture medium. Subsequent screening of 21 out of 35 clones was performed on Greiner plates, prepared as described above. The plates were now first blocked with Blocking reagent and washed. Fifty µl of each hybridoma clone supernatant was tested in duplicate for the presence of sequence independent, but structure specific antibodies, fresh culture medium was tested in four-fold as control. From the original 21 clones, six were selected for further single cell sub-cloning to obtain monoclonal hybridomas. The six clones were seeded at one cell per well of a 96-well culture plate and cultured in medium enriched with 10% v/v FCS. The clones were all tested for binding to two coated amyloids. For each of the six clones five sub-clones were identified that bound to the two amyloids, for subsequent culturing in 25 cm$^2$ culture flasks. Isotyping of the thirty subclones using fluorescently labeled isotype-specific antibodies has been performed by the ABC-Hybridoma facility (M. Smits) according to the recommendations of the manufacturer (Luminex, Austin, Tex., USA).

γ-globulins with altered conformation was prepared as follows. To prepare heat-denatured γ-globulins, lyophilized γ-globulins were heated to 85° C. One mg ml$^{-1}$ γ-globulins in 67 mM NaP$_i$ buffer pH 7.0, 100 mM NaCl, was heated for five cycles in PCR cups in a PTC-200 thermal cycler (MJ Research, Inc., Waltham, Mass., USA). In each cycle, γ-globulins was heated from 30 to 85° C. at a rate of 5° C./minute. Acid- and base denatured γ-globulins was prepared by adding either 60 µl 5 M HCl or 60 µl 5 M NaOH to 26 ml of 10 mg ml$^{-1}$ γ-globulins in HBS (10 mM HEPES, 4 mM KCl, 137 mM NaCl, pH 7.3), followed by a 40-minute incubation at 37° C. Then, either 60 µl 5 M NaOH or 60 µl 5 M HCl was added respectively to neutralize the previously added acid or base. In a control solution, 60 µl 5 M HCl and 60 µl 5 M NaOH was pre-mixed and added to the γ-globulins solution, before the 40-minute incubation at 37° C. As a final step before storage at −80° C., all three solutions were diluted 1:1 in HBS; final concentration 5 mg ml$^{-1}$. Oxidized forms of freshly dissolved γ-globulins were obtained as follows: I. 3.1 mg ml$^{-1}$ γ-globulins in PBS with 20 µM CuSO$_4$, II. 1 mg ml$^{-1}$ γ-globulins in PBS with 480 µM CuCl$_2$, III. 367 µg ml$^{-1}$ γ-globulins in PBS with 480 µM CuCl$_2$, and IV. 367 µg ml$^{-1}$ γ-globulins in PBS with 200 µM CuCl$_2$. All four samples were oxidized overnight at 37° C. Oxidation was stopped by adding 1 mM EDTA. The samples were tested for tPA activating properties and influence on ThT fluorescence. The solutions were then dialyzed against PBS for 48 hours and coated onto an Immobilizer Amino plate (Nunc, Denmark) to check for the binding of hybridoma antibodies.

When binding of a monoclonal antibody to an aggregate with amyloid-like properties was confirmed, the influence of Congo red on this interaction was tested as follows. Amyloid γ-globulins were coated onto a high-binding plate (Greiner Microlon, Bio-One GmbH, Frickenhausen, Germany), blocked with Roche blocking reagent, and overlayed with 10 times diluted hybridoma cell culture medium with a concentration series of Congo red. In addition, the inhibitory effect of compounds with cross-β structure conformation on binding of a monoclonal antibody to immobilized cross-β structure conformation comprising antigens was tested with an ELISA set-up. For this purpose, a limiting amount of antigen, i.e., 0.5 µg ml$^{-1}$ amyloid γ-globulins, was immobilized onto a Greiner high-binding plate. It was determined that 80 times diluted hybridoma cell culture supernatant contains an amount of antibody that results in less than maximal signal when used in ELISAs with immobilized proteins with cross-β structure conformation (not shown). Now, concentration series of freshly dissolved-, amyloid-, acid-denatured- and base-denatured γ-globulins at 0.1, 1, 10 and 100 μg ml$^{-1}$ was added to the 80 times diluted hybridoma cell culture supernatant, and used to overlay the immobilized amyloid γ-globulins. The amount of bound antibody was determined with RAMPO. The signals obtained with 0.1 μg ml$^{-1}$ γ-globulins added to the hybridoma cell culture supernatant solution was arbitrarily set to 100 for all four types of γ-globulins.

Results: Monoclonals Bind Cross-γ Structure Conformation
The Cross-β Structure Conformation Activates Components of the "Cross-β Structure Pathway"

Many proteins and peptides are known to be able to adopt the amyloid-like cross-β structure conformation. This has led to the idea that refolding of polypeptides from a native fold to an amyloid-like structure is an inherent property, independent of the amino-acid sequence of the polypeptides. We found that tPA and factor XII are specifically activated by many polypeptides, once they have adopted the cross-β structure conformation. This led us to propose that a "cross-β structure pathyway" exists that regulates the recognition and clearance of obsolete proteins.[1] Polypeptides can refold spontaneously at the end of their life cycle. Refolding can also be induced by environmental factors such as pH, glycation, oxidative stress, heat, irradiation, mechanical stress, (proteolytic) breakdown. At least part of the polypeptide refolds and adopts the amyloid-like cross-β structure conformation. This structural motif is then the signal that triggers a cascade of events that induces clearance and breakdown of the obsolete particle. When clearing is inadequate, unwanted polypeptides can aggregate and form toxic structures ranging from soluble oligomers up to precipitating fibrils and amorphous plaques. Various disease are associated with protein aggregation and amyloid formation, such as Alzheimer's disease, Huntington's disease, diabetes mellitus type 2, systemic amyloidoses or Creutzfeldt-Jakob's disease, depending on the underlying polypeptide that accumulates and on the part of the body where accumulation occurs.

In addition to the contact system and the fibrinolytic system, which are activated by factor XII and tPA respectively, we have disclosed that the immune system is also part of the proposed cross-β structure pathway (see patent P71713EP00). Cells, including those of the innate immune system, such as macrophages and dendritic cells express scavenger receptors that bind proteins containing cross-β structure conformation. Together with extracellular proteases, such as tPA and factor XII, these cells act as a first defense mechanism to adequately regulate the turnover of unwanted proteins. A second line of defense within the cross-β structure pathway is the clearance of any particle exposing cross-β structure conformation by triggering the adaptive immune system to elicit specific antibodies to the "foreign" structure and/or a T-cell response. Those antibodies may be raised against any sequential or structural detail of the obsolete particle, or against a combination thereof. We now show that the cross-β structure conformation plays a central role in immunogenicity. The set of proteins with cross-β structure conformation that may trigger an immune response is broader than unfolded-/refolded- and aggregated self-polypeptides, and comprises, but is not restricted to, pathogens exposing coat proteins with amyloid-like structure.[5] Following the ideas of the "danger signal" model,[9] it is appreciated that regular unfolding of self-proteins at the end of their life cycle does not elicit an (auto-)immune response, but that excessive formation of cross-β structure conformation or a second stimulus is required to trigger immunogenicity. For example, such a second stimulus can be provided by ligands that activate Toll-like receptors. These ligands include CpG-ODN or lipopolysaccharide (LPS). We established that such ligands, including LPS and CpG-ODN can themselves induce amyloid properties in proteins which may contribute to the immune response. Intracellular processing of CpG-ODN mediated by Toll-like receptor 9 after uptake via yet undefined receptors[10] is putatively tightly associated with the amyloid co-stimulus.

Monoclonal Antibodies with Specificity for Proteins that Comprise the Cross-β Structure Conformation Substantial proof for the aforementioned role of the cross-β structure conformation in eliciting an immune response can come from immunization experiments with amyloid-like structures, which may result in cross-β structure conformation specific antibodies. For this purpose, a mouse was sequentially immunized with human amyloid Aβ(1-40) E22Q, chicken serum amyloid A and glycated human hemoglobin with amyloid-like properties, followed by a final boost with amyloid human fibrin peptide FP6. Hybridomas were formed and their cell culture supernatants were screened for the presence of antibodies that specifically recognize an epitope that is only recognized when cross-β structure conformation is present in any polypeptide with an amino-acid composition that is unrelated to antigens used for immunization. Out of 768 clones six clones, 2E2, 4F4, 7H1, 7H2, 7H9 and 8F2, were selected that show affinity for a broader range of amyloid-like aggregates other than the antigens used for immunization (FIG. 1). Binding to amyloid γ-globulins, amyloid FP13 K157G, freshly dissolved hemoglobin, glycated hemoglobin, Aβ and freshly dissolved γ-globulins was tested. The clones of 2E2 are all of the IgG1 isotype whereas all other clones are of the IgM isotype. In 7H9, also antibodies with the IgG2b subtype are identified, a phenomenon that is putatively due to the fusion of two B-cells within one hybridoma. Native control proteins or peptides without cross-β structure conformation do not bind the selected monoclonal antibodies (see, for example, clone 7H1, FIG. 1, Panel C). This is a further indication for the role of cross-β structure conformation in recognition by these antibodies. Thus, by these selective screenings, antibodies that specifically recognize an epitope within the cross-β structure conformation or that is only present upon refolding into cross-β structure conformation in any polypeptide sequence are found. These results illustrate that antibodies can be obtained that specifically recognize refolded proteins comprising cross-β structure conformation. Such antibodies can thus recognize a common epitope in proteins comprising cross-β structure conformation. However, antibodies can thus also be obtained that specifically bind to a cross-β structure conformation in the context of a unique antigen or to a unique epitope, whose exposure requires the presence of cross-β structure conformation. We anticipated that in our set-up, such cross-β structure conformation dependent antibodies would bind epitopes that require the presence of cross-β structure conformation in one of the used antigens, thus in either Aβ (1-40) E22Q, or serum amyloid A, or glycated Hb. Interestingly, 7H2 binds specifically to amyloid γ-globulins and base-denatured γ-globulins, but not to native γ-globulins, nor to the amyloid antigens used for the immunizations, i.e., Aβ (1-40) E22Q, Hb-AGE:32 (FIG. 1, Panels G-J).

The Cross-β Structure Conformation is Part of the Epitope for Monoclonal Antibody 7H2

Now that we established that monoclonal 7H2H2 binds specifically to human γ-globulins preparations which comprise the cross-β structure conformation, we tested whether the amyloid specific dye Congo red can compete for this interaction. Indeed, when a concentration series of Congo red is added to the 10 times diluted cell culture medium of 7H2H2, binding of the antibody is inhibited for up to approximately 66% with 500 μM Congo red (FIG. 1, Panel K). This observation further indicates that 7H2H2 binds to an epitope that is at least in part composed of a cross-β structure conformation.

Figure 10:
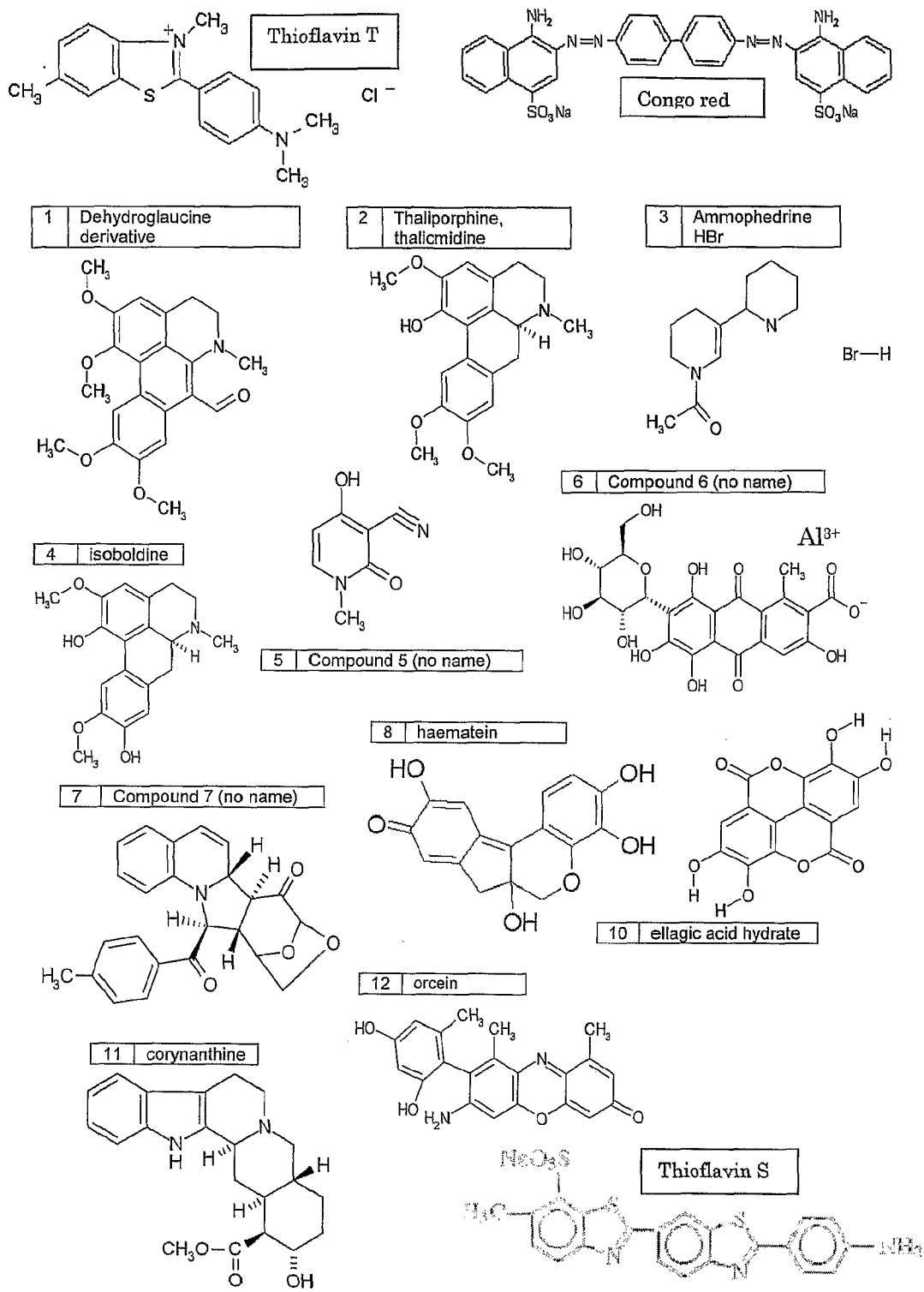
FIG. 10: Compounds that influence interaction of tPA with misfolded proteins Hb-AGE, heat-denatured misfolded ovalbumin and amyloid-β. Compounds selected from the set of small compounds are depicted that induce increased or inhibited binding of tPA to immobilized misfolded proteins glycated hemoglobin, heat-denatured ovalbumin and amyloid-β, in the presence of ε-amino caproic acid, which directs binding of tPA to amyloid-like ligands to its finger domain. Known amyloid binding compounds Congo red, that inhibits binding of tPA and IgIV, Thioflavin T, that promotes binding of tPA and IgIV, and Thioflavin S are shown for comparison. A graphical representation of polymer dextran sulphate 500,000 Da is not shown. Numbering is according to Table 9 and based on our screening assays. Compounds 5, 6 and 7 have no name.

Monoclonal Antibody 7H2 Preferentially Binds to a Subset of Amyloid-Like Aggregates of γ-Globulins As mentioned earlier, varying environmental factors can induce protein refolding into cross-β structure conformation. However, different environmental factors may induce cross-β structure conformation in a different part of a protein. Hence, depending on the nature of the cross-β structure conformation inducing compound the context of the cross-β structure conformation in a given obsolete protein may differ and this may provide different epitopes. By using different denaturing conditions we made several preparation of γ-globulins with cross-β structure conformation. In the Congo red- and ThT fluorescence enhancement assays acid-denatured γ-globulins gave higher signals than base-denatured γ-globulins; in the tPA activation assay the opposite pattern is seen (FIG. 1, Panels L-N). Noteworthy, after oxidation and after acid- or base treatments γ-globulins appeared as white precipitates. To circumvent potential differences caused by differences in coating efficiency in an ELISA, an inhibition assay was performed. Amyloid γ-globulins were immobilized and overlayed with 7H2H2 to which concentration series of either freshly dissolved-, or base-denatured, or acid-denatured, or the same amyloid γ-globulins that was coated, was added. When 7H2H2 binds to any of the γ-globulins preparations added, decreased binding of 7H2H2 to the immobilized amyloid γ-globulins is monitored. The negative control freshly dissolved γ-globulins did indeed not interfere with 7H2H2 binding to immobilized amyloid γ-globulins, whereas positive control amyloid γ-globulins in solution was an effective inhibitor (FIG. 10). Base-denatured γ-globulins inhibited 7H2H2 binding as effectively as amyloid γ-globulins, whereas acid-denatured γ-globulins had no influence on 7H2H2 binding. This may point to differences in type, size, and/or location within the denatured γ-globulins molecules, of the cross-β structure conformation. In summary, 7H2 is a monoclonal antibody that specifically binds to a unique epitope in γ-globulins that requires the presence of cross-β structure conformation, but only when induced by treatment at high pH, but not when induced by treatment at low pH. Similar inhibition studies are conducted with all six monoclonals and concentration series of tPA, K2P tPA, finger domains thereof, soluble fragment of receptor for advanced glycation endproducts, ThT, ThS, and mutual exchanged monoclonal antibodies.

Predicted Explanation for an Autoimmune Response of the Immunized Mouse

The observation that the mouse elicited an antibody against denatured human γ-globulins may point to an autoimmune response of the immunized mouse against putatively refolded and/or aggregated endogenous immunoglobulins with cross-β structure conformation. Based on literature data showing that C1q binds to fibrillar prion protein and to Aβ,[11, 12] and to IgM and IgG antibodies solely when the antibodies are bound to an antigen, we suppose that upon binding of an antibody to an antigen refolding is induced in the antibody resulting in locally adopting the cross-β structure conformation. This induced cross-β structure conformation in the antibody may then be the binding site for C1q. During the immunization, protein aggregates bind immunoglobulins that will then also adopt cross-β structure conformation upon binding. Since the aggregates are insoluble and resistant to clearance this results in continuous exposure of the cross-β structure conformation in the immunoglobulins. Such prolonged exposure of the cross-β structure conformation in the bound and refolded immunoglobulins comprising cross-β structure conformation may have triggered a new (auto-)immune response resulting in auto-antibody 7H2.

There is further precedent for our hypothesis that cross-β structure conformation can be present in immunoglobulins and result in the generation of anti-immunoglobulin antibodies. Aggregated immunoglobulins with amyloid cross-β structure conformation are seen during light chain amyloidosis[13, 14] in multiple myeloma patients, whom overexpress Ig light chains.

Antibodies with Specificity for a Subset of Cross-β Structure Conformations: Relevance to the Clinic Our observations that antibodies can be elicited against polypeptide assemblies with cross-β structure conformation that also bind to polypeptides with similar amyloid-like conformation but with unrelated amino-acid sequence, points to a role for this conformation in the induction of an immune response. The identification of antibodies of the IgG subtype and the IgM subtype indicate that both the innate immune system and the adaptive immune system can be triggered by the cross-β structure conformation. With the specificity of 7H2 for human γ-globulins with cross-β structure conformation and not for aggregated γ-globulins lacking the cross-β structure conformation we demonstrate that biomolecules can be developed with specificity for only those aggregates that comprise the cross-β structure conformation. That this structural element is part of the epitope is suggested by the inhibition study with Congo red.

Each type of specific or broad range anti-cross-β structure antibody can be tested for potential neutralizing properties in any kind of assay that serves as a model to test immunogenicity and/or toxicity and/or thrombogenicity of compounds that comprise the cross-β structure conformation, or in any other assay conducted to study the in vitro, in vivo or ex vivo pathophysiological or physiological role of amyloid. For example, the role of cross-β structure conformation in fibrin (ogen) biology can be examined with the use of the antibodies, as well as the a role in blood platelet biology. Moreover, anti-cross-β structure antibodies may have therapeutic value. For example, monoclonal 7H2 may have beneficial effects when administered to patients suffering from (systemic) amyloidosis related to aggregation of immunoglobulins or fragments thereof.

Example 2

Anti-β2GPI Autoantibodies Derived from Patients with Antiphospholipid Syndrome Recognize β2GPI Comprising Cross-β Structure, but not Native β2GPI Materials & Methods
Plasminogen Activation Assay.

Plasmin (Plm) activity was assayed as described.[4] Peptides and proteins that were tested for their stimulatory ability were used at 100 μg ml$^{-1}$, unless stated otherwise. Tissue-type plasminogen activator (tPA, Actilyse, Boehringer-Ingelheim) and plasminogen (Plg, purified form human plasma by lysine-affinity chromatography) were used at concentrations of 400 pM and 1.1 or 0.22 μM, respectively. Chromogenic substrate S-2251 (Chromogenix, Instrumentation Laboratory SpA, Milano, Italy) was used to measure Pls activity.

Thioflavin T Fluorescence

Fluorescence of ThT—amyloid-like protein/peptide adducts was measured as follows. Solutions of 25 μg ml$^{-1}$ of protein or peptide preparations were prepared in 50 mM glycine buffer pH 9.0 with 25 µM ThT. Fluorescence was measured at 485 nm upon excitation at 435 nm. Background signals from buffer, buffer with ThT and protein/peptide solution without ThT were subtracted from corresponding measurements with protein solution incubated with ThT. Regularly, fluorescence of Aβ was used as a positive control, and fluorescence of FP10 (SEQ ID NO:3), a non-amyloid fibrin fragment,[4] and buffer was used as a negative control. Fluorescence was measured in triplicate on a Hitachi F-4500 fluorescence spectrophotometer (Hitachi, Ltd., Tokyo, Japan).

Transmission Electron Microscopy Imaging

For TEM analysis of protein and peptide solutions grids were prepared according to established procedures. Samples were applied to 100-mesh copper grids with carbon coated Formvar (Merck, Germany), and subsequently washed with PBS and $H_2O$. Grids were applied to droplets of 2% (m/v) methylcellulose with 0.4% (m/v) uranylacetate pH 4. After a 2-minute incubation, grids were dried on a filter. Micrographs were recorded at 80 kV, at suitable magnifications on a JEM-1200EX electron microscope (JEOL, Japan).

Activation of tPA by $\beta_2$-Glycoprotein I, Binding of Factor XII and tPA to $\beta_2$-Glycoprotein I and ThT and TEM Analysis of $\beta_2$-Glycoprotein I Purification of $\beta_2$-glycoprotein I ($\beta_2$GPI) was performed according to established methods.[15, 16] Recombinant human $\beta_2$GPI was made using insect cells and purified as described.[15] Plasma derived $\beta_2$GPI as used in a factor XII ELISA, the Plg-activation assay and in the anti-phospholipid syndrome antibody ELISA (see below), was purified from fresh human plasma as described.[16] Alternatively, $\beta_2$GPI was purified from, either fresh human plasma, or frozen plasma using an anti-$\beta_2$GPI antibody affinity column.[17]

Activation of tPA (Actilyse, Boehringer-Ingelheim) by $\beta_2$GPI preparations was tested in a Plg-activation assay (see above). Hundred µg ml$^{-1}$ plasma $\beta_2$GPI or recombinant $\beta_2$GPI were tested for their stimulatory activity in the Plg-activation assay and were compared to the stimulatory activity of peptide FP13.[4]

Binding of human factor XII from plasma (Calbiochem) or of recombinant human tPA to $\beta_2$GPI purified from human plasma, or to recombinant human $\beta_2$GPI was tested in an ELISA. Ten µg of factor XII or tPA in PBS was coated onto wells of a Costar 2595 ELISA plate and overlayed with concentration series of $\beta_2$GPI. Binding of $\beta_2$GPI was assessed with monoclonal antibody 2B2.[17]

Binding of factor XII to β2GPI was also tested using immunoblotting. $\beta_2$GPI (33 µg) purified either from fresh plasma or from frozen plasma loaded onto a 7.5% polyacrylamide gel. After blotting to a nitrocellulose membrane (Schleicher & Schuell), the blot was incubated with 1000× diluted rabbit polyclonal anti-human factor XII antibody (#233504, Calbiochem) and after washing with 3000× diluted peroxidase-coupled swine anti-rabbit immunoglobulins (SWARPO, #P0217, DAKO, Denmark).

ThT fluorescence of $\beta_2$GPI was measured as follows. Purified $\beta_2$GPI from human plasma (400 µg ml$^{-1}$ final concentration) was incubated with or without 100 µM CL vesicles or 250 µg ml$^{-1}$ of the adjuvant dextran sulphate MW 500 kDa (DXS500k), in 25 mM Tris-HCl, 150 mM NaCl, pH 7.3. In the ThT fluorescence assay, fluorescence of $\beta_2$GPI in buffer, of CL or DXS500k in buffer, of buffer and ThT alone, and of $\beta_2$GPI-CL adducts and $\beta_2$GPI-DXS500k adducts, with or without ThT, was recorded as described above (section ThT fluorescence). In addition, transmission electron microscopy (TEM) images were recorded with CL, β2GPI from human plasma, with or without CL, and with recombinant β2GPI, as described.[1]

Interference with Binding of Anti-$\beta_2$GPI Autoantibodies from Antiphospholipid Syndrome Autoimmune Patients to Immobilized $\beta_2$GPI by Recombinant $\beta_2$GPI and not by Plasma Derived $\beta_2$GPI When plasma derived $\beta_2$GPI is coated onto hydrophilic ELISA plates, anti-$\beta_2$GPI auto-antibodies isolated from plasma of antiphospholipid syndrome autoimmune patients can bind.[18] To study the influence of coincubations of the coated $\beta_2$GPI with the antibodies together with plasma $\beta_2$GPI or recombinant $\beta_2$GPI, concentration series of $\beta_2$GPI were added to the patient antibodies. Subsequently, binding of the antibodies to coated $\beta_2$GPI was determined.

Results

The Anti-Phospholipid Syndrome and Conformationally Altered $\beta_2$-Glycoprotein I The anti-phospholipid syndrome (APS) is an autoimmune disease characterized by the presence of anti-$\beta_2$-glycoprotein I auto-antibodies.[15, 18] Two of the major clinical concerns of the APS are the propensity of auto-antibodies to induce thrombosis and the risk for fetal resorption.[19, 20] Little is known about the onset of the autoimmune disease. Recent work has demonstrated the need for conformational alterations in the main antigen in APS, $\beta_2$-glycoprotein I ($\beta_2$GPI), before the initially hidden epitope for auto-antibodies is exposed.[15, 18, 21] Binding of native $\beta_2$GPI to certain types of ELISA plates mimics the exposure of the cryptic epitopes that are apparently present in APS patients.[15, 18, 21] It has been demonstrated that anti-$\beta_2$GPI autoantibodies do not bind to globular $\beta_2$GPI in solution, but only when $\beta_2$GPI has been immobilized to certain types of ELISA plates.[15, 18, 21] The globular (native) form of the protein is not immunogenic, but requires the addition of CL, apoptotic cells or modification by oxidation.[3, 22-24] Thus the generation of autoantibodies seems to be triggered by and elicited against a conformationally altered form of $\beta_2$GPI. It has previously been proposed that the induction of an adaptive immune response requires a so-called "danger" signal, which among other effects stimulates antigen presentation and cytokine release by dendritic cells.[25] The following results imply that CL induces cross-β structure conformation in β2GPI which than serves as a danger signal. In analogy other negatively charged phospholipids, or structures that contain negatively charged lipids, such as liposomes or apoptotic cells, or other inducers of cross-β structure conformation, including LPS, CpG-ODN that possess cross-β structure conformation inducing properties, may be immunogenic due to the fact, at least in part, that they induce cross-β structure conformation.

Figure 4:
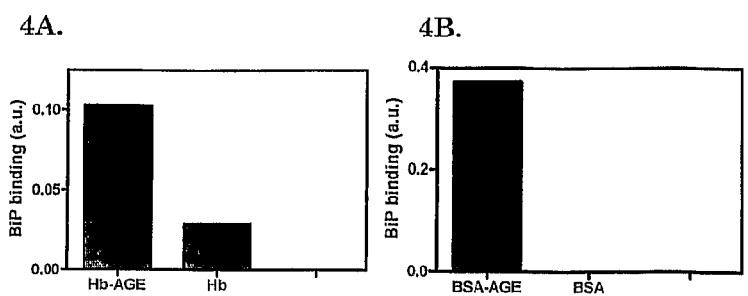
FIG. 4: Binding of recombinant human BiP to cross-beta structure comprising proteins. A. In an ELISA set-up BiP binds to glycated hemoglobin (Hb-AGE) and to a lesser extent to freshly dissolved lyophilized hemoglobin. B. BiP binds to glycated albumin (BSA-AGE) and not to native BSA.

Factor XII and tPA Bind to Recombinant $\beta_2$GPI and to $\beta_2$GPI Purified from Frozen Plasma, but not to $\beta_2$GPI Purified from Fresh Plasma Recombinant $\beta_2$GPI, but not $\beta_2$GPI purified from fresh plasma stimulate tPA-mediated conversion of Plg to plasmin, as measured as the conversion of the plasmin specific chromogenic substrate S-2251 (FIG. 2, Panel A). Using an ELISA it is shown that tPA and factor XII bind recombinant $\beta_2$GPI, but not bind to $\beta_2$GPI purified from fresh human plasma (FIG. 2, Panels B, C). Recombinant $\beta_2$GPI binds to factor XII with a $k_D$ of 20 nM (FIG. 2, Panel C) and to tPA with a $k_D$ of 51 nM (FIG. 2, Panel B). In addition, $\beta_2$GPI purified from plasma that was frozen at −20° C. and subsequently thawed, factor XII co-elutes from the anti-$\beta_2$GPI antibody affinity column, as shown on Western blot after incubation of the blot with anti-factor XII antibody (FIG. 2, Panel D). This suggest that $\beta_2$GPI refolds into a conformation containing cross-β structure upon freezing. In FIG. 2, Panel E, the inhibitory effect of recombinant $\beta_2$GPI on binding of anti-$\beta_2$GPI autoantibodies isolated from patients with APS to immobilized $\beta_2$GPI is shown. It is seen that plasma derived $\beta_2$GPI in solution has hardly an effect on the antibody binding to immobilized $\beta_2$GPI. FIG. 2, Panel F, shows that exposure of $\beta_2$GPI to CL or DXS500k introduces an increased ThT fluorescence signal, illustrating a conformational change in $\beta_2$GPI accompanied with the formation of cross-$\beta$ structure conformation. Again, recombinant $\beta_2$GPI initially already gave a higher ThT fluorescence signal than native $\beta_2$GPI purified from plasma. In addition, exposure of plasma β2GPI and rec. β2GPI to adjuvants/denaturants LPS or CpG-ODN also induces an increase in ThT fluorescence, which is larger with rec. β2GPI than with plasma β2GPI for both adjuvants (FIG. 2, Panel M, and FIG. 4, Panel C). These data not only indicate that recombinant β2GPI already comprises more cross-$\beta$ structure conformation than plasma β2GPI, but that recombinant β2GPI also adopts more readily this conformation when contacted to various adjuvants and surfaces, i.e., CL, DXS500k, LPS and CpG-ODN. In FIG. 2, Panel G, it is shown that exposure of $\beta_2$GPI to CL, immobilized on the wells of an ELISA plate, renders $\beta_2$GPI with tPA binding capacity. Binding of $\beta_2$GPI directly to the ELISA plate results in less tPA binding. These observations also show that CL has a denaturing effect, thereby inducing amyloid-like conformation in $\beta_2$GPI, necessary for tPA binding. These observations, together with the observation that exposure of $\beta_2$GPI to CL vesicles induced ThT binding capacity (FIG. 2, Panel F), show that exposure of $\beta_2$GPI to a denaturing surface induces formation of amyloid-like cross-$\beta$ structure conformation.

Epitopes for Autoantibodies are Specifically Exposed on Non-Native Conformations of β2GPI Comprising Cross-$\beta$ Structure Conformation FIG. 2 shows that preparations of $\beta_2$GPI react with amyloid cross-$\beta$ structure markers ThT, tPA and factor XII. In addition, exposure of $\beta_2$GPI to cardiolipin (CL) introduces tPA binding capacity (FIG. 2, Panel G). Furthermore, large fibrillar structures are seen on TEM images of plasma $\beta_2$GPI in contact with CL (FIG. 2, Panel H, image 2 and 3). Small CL vesicles seem to be attached to the fibrillar β2GPI. Images of plasma $\beta_2$GPI alone (FIG. 2, Panel H, image I) or CL alone (not shown) revealed that no visible ultrastructures are present. In contrast, non-fibrillar aggregates and relatively thin curly fibrils can be seen on images of recombinant $\beta_2$GPI (FIG. 2, Panel H, image 4). These observation show that exposure of $\beta_2$GPI to CL and expression and purification of recombinant $\beta_2$GPI result in an altered multimeric structure of $\beta_2$GPI, when compared to the monomeric structure observed with X-ray crystallography.[26] The $\beta_2$GPI preparations with cross-$\beta$ structure conformation express epitopes that are recognized by anti-$\beta_2$GPI auto-antibodies isolated from APS patient plasma. Furthermore, exposure of $\beta_2$GPI to CL or DXS500k induces an increased fluorescence when ThT is added, indicative for the formation of cross-$\beta$ structure conformation when $\beta_2$GPI contacts a negatively charged surface. Interestingly, it has previously been observed that exposure of $\beta_2$GPI to CL is a prerequisite for the detection of anti-$\beta_2$GPI antibodies in sera of immunized mice.[3] These combined observations point to a role for conformational changes in native $\beta_2$GPI, necessary to expose new immunogenic sites. Our results indicate that the cross-$\beta$ structure element is part of this epitope. We predict that the cross-$\beta$ structure conformation can be relatively easily formed by one or more of the five domains of the extended $\beta_2$GPI molecule.[26] Each domain comprises at least one $\beta$-sheet that may function as a seed for local refolding into cross-$\beta$ structure conformation.

A person skilled in the art is now able to test the hypothesis that the cross-$\beta$ structure conformation is the essential to elicit anti-$\beta_2$GPI antibodies. Immunization studies with native $\beta_2$GPI and conformationally altered $\beta_2$GPI, with or without cross-$\beta$ structure conformation, can be performed in the presence or absence of a compound, including ThT, tPA, RAGE, CD36, anti-cross-$\beta$ structure antibodies or a functional equivalent thereof, that inhibits the activity of cross-$\beta$ structure conformation. Alternatively, in vitro studies with antigen presenting cells (APC), including dendritic cells (DC) can be performed. Sources of conformationally altered $\beta_2$GPI are recombinant $\beta_2$GPI, or $\beta_2$GPI exposed to any denaturing surface, e.g., plastics, CL, DXS500k and potentially other adjuvants. In addition, structurally altered $\beta_2$GPI may be obtained by any other chemical or physical treatment, e.g., heating, pH changes, reduction-alkylation. A person skilled in the art is able to design and perform in vitro cellular assays and in vivo mouse models to obtain further evidence for the role of the cross-$\beta$ structure conformation in autoimmunity (see below). To establish whether the cross-$\beta$ structure element is essential for eliciting an immune response or for antibody binding, inhibition studies can be conducted with any cross-$\beta$ structure binding compound that may compete with antibody binding or that may prevent an immune response.

Our observations indicate that cross-$\beta$ structure conformation is necessary for the induction of an adaptive immune response. The cross-$\beta$ structure conformation could also be part of an epitope recognized by autoimmune antibodies. Based on our studies it is predicted that other diseases and complications in which autoantibodies are implicated are mediated by a protein comprising cross-$\beta$ structure conformation. In addition to the antiphospholipid syndrome such conditions include, but are not limited to systemic lupus erythematosus (SLE), type I diabetes, red cell aplasia and the formation of inhibitory antibodies in hemophilia patients treated with factor VIII. A person skilled in the art is now able to address whether the cross-$\beta$ structure is present in proteins causing autoimmune disease. For example, provided that the underlying protein is known, a skilled person can perform analysis to detect the presence of cross-$\beta$ structure. Methods to determine whether a protein comprises a cross-$\beta$ structure conformation are available to the skilled person. Examples of such methods include, but are not limited to staining with Congo red, Thioflavin S (ThS) or Thioflavin T (ThT), an ELISA binding assay using tPA or a functional fragment thereof, an ELISA using one of the compounds or proteins listed in Tables 1-3, a tPA activation assay or a X-ray fiber diffraction analysis. A person skilled in the art is now, for example, also able to screen hemophilia patients with anti-factor VIII autoantibodies for the presence of antibodies in their plasma that recognize the cross-$\beta$ structure conformation. A more detailed analysis reveals whether putative cross-$\beta$ structure binding antibodies specifically bind (in part) to cross-$\beta$ structure conformation in the antigen, or whether the antibodies bind to cross-$\beta$ structure conformation present in any unrelated protein.

Example 3

Two Distinct Amyloid-Like Conformations of a Peptide

Materials & Methods: Fibrin Peptide FP6 Adopts Two Distinct Amyloid-Like Conformations Solutions of fibrin peptide FP6, $NH_2$-IDIKIR-COOH (SEQ ID NO:4) (Peptide facility, Dutch Cancer Institute, Amsterdam, The Netherlands) were prepared in various ways. FP6 was dissolved in hexafluoro-2-propanol and trifluoroacetic acid in a 1:1 volume ratio, at approximately 10 mg ml⁻¹. Solvents were subsequently evaporated and FP6 was dissolved in H$_2$O at 1 mg ml⁻¹ or at 10 mg ml⁻¹. Batches were incubated at 37° C. or at 65° C., for 72 hours, and subsequently stored at room temperature. Before preparation of X-ray diffraction samples with the 37° C.-incubated sample at 1 mg ml⁻¹, the solution was concentrated by air-drying to approximately 5 mg ml⁻¹. Another amount of FP6 was dissolved directly in H$_2$O, at 10 mg ml⁻¹, and used immediately for preparing X-ray diffraction samples. Separate samples were prepared similarly and analyzed by electron spray ionization mass spectrometry (ESI-MS) to obtain information on the distribution of the peptide over putatively present oligomers (Dr C. Versluis, Department of Biomolecular Mass Spectrometry, Bijvoet Center for Biomolecular Research, Utrecht University, Utrecht, The Netherlands). With FP6 dissolved directly at 10 mg ml⁻¹, influence of 25 µg ml⁻¹ dilutions on Congo red and ThT fluorescence was tested following the given standard procedures, directly after preparation of the peptide solution or after three days incubation at room temperature. Positive control and negative control were amyloid-β (1-40) E22Q (Aβ(1-40) E22Q) and non-amyloid fibrin peptide FP10 (SEQ ID NO:3) (see ref.[4]). With these preparations, also the ability to induce tPA activation was tested. In a Costar 2595 ELISA plate (Corning, N.Y., USA), 0.5 µl of each sample (100 µg ml⁻¹ final concentration) was mixed with final concentrations of 100 µg ml⁻¹ plasminogen, 400 pM tPA, 0.5 mM chromogenic plasmin substrate S2251 (Chromogenix, Instrumentation Laboratories, Breda, The Netherlands) in HBS (10 mM HEPES, 4 mM KCl, 137 mM NaCl, pH 7.3), and incubated at 37° C. Formation of plasmin upon tPA activation was followed kinetically.

For transmission electron micrograph (TEM) imaging with FP6 at 10 mg ml⁻¹, incubated at 37° C. and 65° C., samples were applied to 100-mesh copper grids with carbon coated Formvar (Merck, Germany), and subsequently washed with PBS and H$_2$O. Grids were applied to droplets of 2% (m/v) methylcellulose with 0.4% (m/v) uranylacetate pH 4. After a two-minute incubation, grids were dried on a filter. Micrographs were recorded at 80 kV, at suitable magnifications on a JEM-1200EX electron microscope (JEOL, Japan).

For X-ray diffraction analyzes, approximately 50 µl of stock solutions were drawn in boro glass X-ray capillaries by capillary forces, and air-dried. For collection of X-ray diffraction patterns capillaries containing the dried samples were placed on a Mar BTD diffractometer (MarResearch, Germany). Scattering was measured using sealed tube CuKα radiation with a graphite monochromator on the Mar345 Image Plate (MarResearch, Germany) during 5 hours. Scattering from air and the glass capillary wall were subtracted using in-house software (VIEW/EVAL, Dept. of Crystal- and Structural Chemistry, Utrecht University, The Netherlands). Data reduction and structure analysis were performed by Dr. Loes Kroon-Batenburg (Department of Crystal- & Structural Chemistry, Bijvoet Center for Biomolecular Research, Utrecht University, Utrecht, The Netherlands).

Size exclusion chromatography is performed on a Superdex peptide PC 3.2/30 column using a SmartSystem (Pharmacia Amersham Biosciences Europe, Roosendaal, The Netherlands) with FP6 that is freshly dissolved in H$_2$O at 10 mg ml⁻¹ and directly applied to the column. Running buffer was H$_2$O and elution was monitored by absorbance measurements at 214 nm. Peak fractions were collected separately and after approximately three days of storage at 4° C. applied to an electron spray ionization mass spectrometer (ESI-MS, Biomolecular MassSpectrometry Facility, Utrecht University, The Netherlands).

Figure 3:
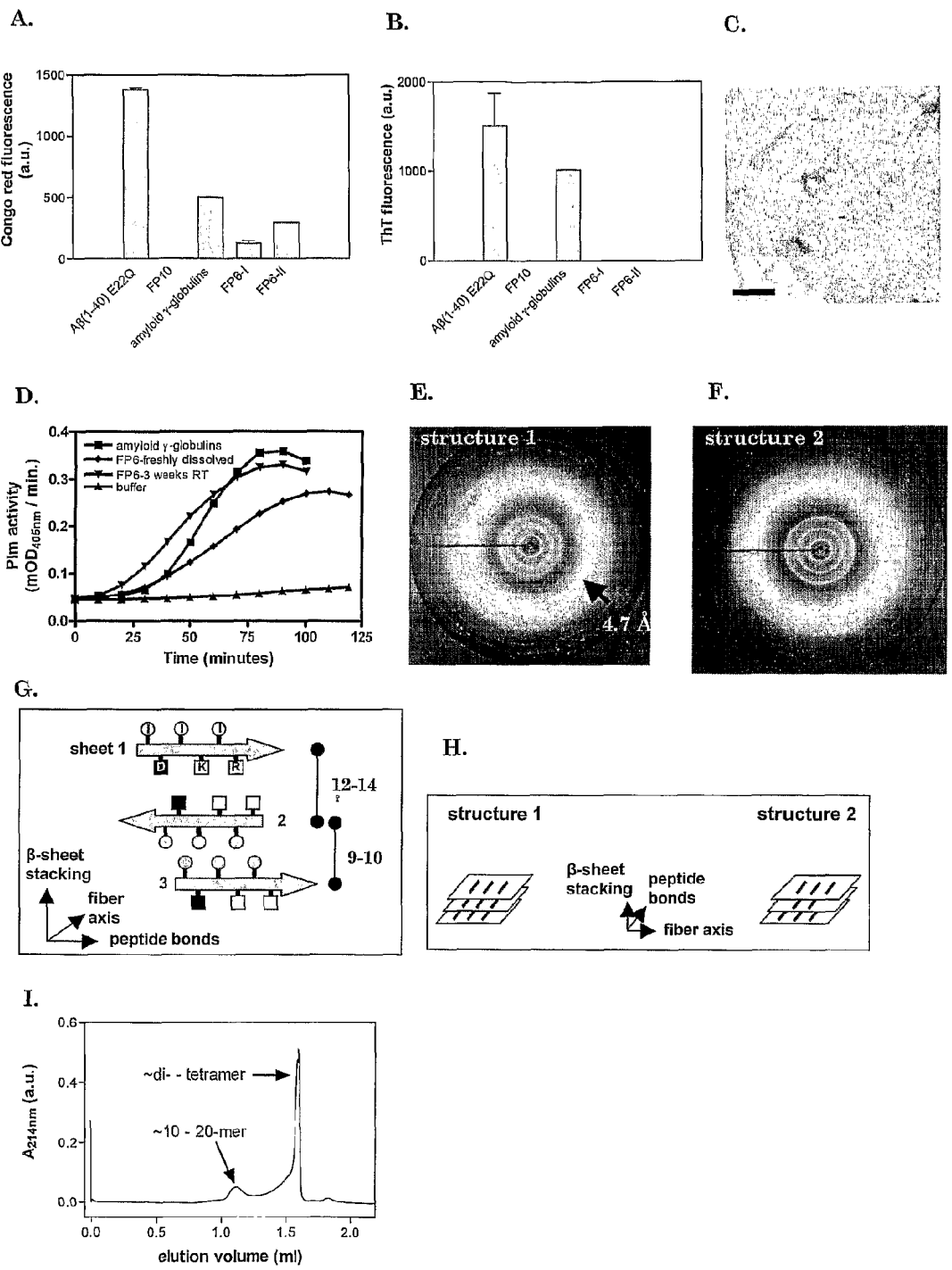
FIG. 3: Structural analysis of fibrin peptide FP6. A. Influence of freshly dissolved FP6 or FP6 incubated for three weeks at room temperature on enhancement of Congo red fluorescence was compared with Aβ (positive control) and FP10 (negative control) (SEQ ID NO:3). B. ThT fluorescence of positive control Aβ, negative control FP10 (SEQ ID NO:3) and freshly dissolved FP6 or three-weeks incubated FP6. C. TEM image showing fibrillar structures in FP6 that was incubated at 65° C. Scale bar: 200 nm. D. TPA activation assay showing the tPA activating properties of freshly dissolved FP6 and three-weeks incubated FP6. Positive control is 100 µg ml$^{-1}$ amyloid γ-globulins. Negative control is buffer (H₂O). E. X-ray diffraction image showing the typical 4.7 Å reflection seen in amyloid-like structures of varying origin. The diffraction pattern belongs to FP6 with amyloid structure type 1. F. X-ray diffraction pattern of FP6 that adopted a fibrillar conformation with amyloid-like properties. Adjacent β-sheets are shifted 2.35 Å and as a result, the 4.7 Å peak, typical in many amyloid structures, is quenched completely. G. Structural model based on the X-ray fiber diffraction analyzes of 37° C.-incubated FP6 and freshly dissolved FP6, showing the β-sheet stacking within the cross-β structure. Alternating layers are supposed, harboring either the hydrophobic isoleucine side-chains (I), or the charged lysine (K), arginine (R) and aspartate (D) residues. H. In the crystal structure of the 37° C. incubated FP6 (structure I), β-sheets in consecutive layers are shifted over half the unit cell length in the direction of the 4.7 Å hydrogen bonds perpendicular to the peptide bonds (fiber axis). In contrast, in the crystal structure of the freshly dissolved FP6 (structure 2), β-strands in consecutive β-sheet layers are oriented on top of each other. I. Size exclusion chromatography run with freshly dissolved FP6.

Results: Fibrin Peptide FP6 can Arrange Itself in Two Distinct Amyloid-Like Conformations The fibrin peptide FP6, NH$_2$-IDIKIR-COOH (SEQ ID NO:4), has been described as the smallest fibrin fragment with tPA activating properties.[27] We were wondering whether this hexapeptide has similar structural properties as seen in non-fibrin polypeptides that activate tPA, i.e., the cross-β structure conformation.[1, 4] Indeed, we found that FP6 has properties illustrating the presence of amyloid-like cross-β structure conformation. The dissolved peptide activates tPA in the chromogenic plasmin activity assay, can form fibrils and enhances Congo red fluorescence (FIG. 3, Panels A-D). An FP6 solution that was dissolved directly in H$_2$O and kept at 65° C. appeared as fibrillar structure on TEM images (FIG. 3, Panel C), whereas FP6 first dissolved in organic solvents and kept in H$_2$O at 37° C. did not reveal any visible oligomer or aggregate at all. X-ray diffraction analyzes revealed that the cross-β structure conformation is present in the preparations tested (not shown). ThT fluorescence is not enhanced with the peptide incubated at room temperature. This implies that ThT interacts differently with the amyloid-like conformation than tPA and Congo red. In line with this observation, in an ELISA, binding of tPA to immobilized amyloid polypeptides amyloid-β and glycated albumin can be effectively inhibited by Congo red, but not by ThT.

The peptide solution that was incubated for three weeks at room temperature shows stronger Congo red fluorescence enhancement and activates tPA to a higher extent than FP6 analyzed directly after it was dissolved, indicating that differing cross-β structure conformations or a different amount of active form of cross-β structure is present (FIG. 3, Panels A, B, D).

X-ray diffraction analyzes not only showed that FP6 comprises amyloid-like structure, but in addition revealed that at one site FP6 first dissolved in organic solvents, then in H$_2$O and incubated at 37° C. or at 65° C., or directly dissolved in H$_2$O, and at the other site FP6 dissolved directly in H$_2$O and kept at room temperature or dissolved directly in H$_2$O pH 2 (HCl) and incubated at 65° C., have adopted two distinct conformations with properties that resemble the cross-β structure. The two distinguishable structures display similar structural features within the plane of the β-sheets that builds up a cross-β structure conformation, with respect to inter β-strand distance (4.7 Å) and dimension of the repeating unit in the direction of the peptide bonds. The X-ray diffraction experiments indicate that β-strands are oriented in an anti-parallel manner (FIG. 3, Panels E, F). However, from the available information it can be deduced that FP6-1 and FP6-2 have two different amyloid-like conformation that both have features of the cross-β structure, that is to say, both structures are composed of layered β-sheets. In the third dimension, in the direction perpendicular to the β-sheets, these β-sheet layers are positioned in an alternating fashion at 9-10 Å or at 12-14 Å distance in both structures (FIG. 3, Panel G). The two structures of FP6-1 and FP6-2 are however distinct with respect to the translational shift of two adjacent β-sheets. In the structure of FP6-1, subsequent layers of β-sheets are positioned right on top of each other (FIG. 3, Panel H). In contrast, in FP6-2 adjacent layers are shifted over 2.35 Å in the direction of the inter β-strand hydrogen bond direction (typically 4.7 Å) in a way that a staggered configuration is adopted (FIG. 3, Panel I). This shift results in the absence of the 4.7 Å reflection, which is a reflection that is seen in many X-ray diffraction analyses of amyloid-like structures. Still, we think that structure 2 can also be designated as an amyloid-like cross-β structure. This is based on the fact that also fibrils with structure 2 are built up by layered β-sheets, like structure 1, and based on recent information that a seven-residue peptide segment from yeast prion-like protein Sup35 adopts an amyloid-like structure similar to structure 2 (ref.[28]). Similar to the infectious nature of mammalian prions, conversion of Sup35 to amyloid-like fibrils is associated with transmissible infection. Interestingly and additive to our observations, other fibrin peptides with cross-β structure conformation, i.e., FP13 with sequence NH$_2$-KRLEVDIDIxIRS-COOH (SEQ ID NO:1), with x=K, G, D, all activate tPA and adopt a structure similar to FP6-1 (ref.[4] and B. Bouma and L. Kroon-Batenburg, data not shown) and FP6 solutions prepared in a way used for the X-ray diffraction analyses that resulted in structure 2, also activate tPA. A careful analysis of the correlation between interaction of markers for cross-β structure conformation with various FP6 preparations and obtained fiber crystal structures reveals whether structural differences seen between FP6 structure 1 and 2 are reflected in, for example, differences in tPA activation, enhancement of Congo red- and ThT fluorescence and appearance on TEM images.

The ESI-MS analyses revealed that preparations of FP6 that were incubated at room temperature or at 37° C., or that were analyzed immediately after dissolving the peptide, all display a similar distribution over monomers up to 15-mers (data not shown). Furthermore, FP6 di/tri/tetramers in the second peak obtained after size-exclusion chromatography (FIG. 3, Panel G), redistributed over the similar range of oligomers ranging from monomers up to 15-mers, as found with samples that were applied directly to the mass spectrometer. This shows that FP6 oligomerization likely reaches a steady state distribution at a certain concentration, and that a specific FP6 oligomer redistributes over the original range of oligomers when isolated. We conclude, therefore, that the cross-β structure conformation of FP6 is not a rigid and inert entity as is suggested for many fibrillar aggregates.

Our ESI-MS- and X-ray diffraction results show that the hexapeptide FP6 can form oligomers consisting of up to 15 peptide molecules, with amyloid-like cross-β structure conformation. Various preparations exhibit different tPA activating properties, appear differently on TEM images, enhance Congo red fluorescence differently and have formed distinct cross-β structure conformations, as depicted from X-ray diffraction data sets. These data provide insight in the diverse nature of the cross-β structure conformation. In fact, the term cross-β structure fold, also referred to as cross-β sheets or cross-β spine, is covering an ensemble of structures. Polypeptides differing in amino-acid sequence or length, or a polypeptide treated in different ways, may appear with cross-β structures that differ from each other to some extent. This was already noticed for a long time when the varying inter β-sheets spacings are concerned.

The intriguing likelihood that every polypeptide can arrange itself in a unique cross-β structure conformation with respect to inter β-sheet spacing and/or with respect to a translational shift between adjacent β-strands, with yet common aspects seen in every amyloid-like fold opens the way to the design of therapeutics, either small molecule drugs or protein-based pharmaceuticals, that are polypeptide- and disease specific. For example, a drug that specifically abolishes the pathological effects of aggregation-prone serum amyloid A (SAA) by binding to aspects of SAA that are unique to the amyloid form of the protein, does not disturb tPA-mediated fibrinolysis upon binding to the cross-β structure conformation in fibrin polymers.

Example 4

Screening of Compound Libraries, Recombinant Proteins and/or Antibodies for the Identification of Lead Compounds that Interact with Misfolded Proteins Introduction:

The following series of experiments is designed to provide proof for beneficial use of the disclosed technology that allows amongst other things, for identification of lead compounds for the development of diagnostics for misfolded protein-related diseases, devices for depletion applications of misfolded protein or therapeutics for disorders associated with protein misfolding, such as Alzheimer's Disease (AD), type II diabetes or other types of amyloidoses. Amyloid-β (Aβ(1-40)E22Q), related to the pathology of AD, heat-denatured misfolded amyloid-like ovalbumin (DOVA) and glycated amyloid-like hemoglobin (Hb-AGE), related to diabetes pathology, were used as model misfolded proteins. As shown before, tissue-type plasminogen activator (tPA) is able to bind to, and can be activated by misfolded proteins.[4, 1, 29] Therefore, inhibition of interaction of this natural misfolded protein binding serine protease tPA with misfolded protein is beneficial for patients in certain circumstances, whereas in other cases increased and/or accelerated interaction of tPA with obsolete misfolded protein is beneficial within the proposed "Cross-beta Pathway" for clearance of obsolete proteins.[1] Apart from the prototype of a protein with affinity for amyloid-like misfolded protein, i.e., tPA, the screening technology is applicable for any protein that interacts with misfolded protein(s), such as those listed in Table 2 and Table 3. In the described experiments below the disclosed technology was used to isolate and characterize compounds acting on the interaction of tPA with the three model misfolded proteins. Thus, the influence of potential lead compounds on the interaction of tPA with amyloid-like misfolded proteins is used as a first measure for the binding of the compounds to the misfolded proteins. In addition to the identification of potential lead drug candidates, our technology also reveals new target compounds that can be implemented in diagnostic tools for detection of misfolded protein, and in compounds that can be implemented in misfolded protein depletion technology. Furthermore, competition binding studies in which mixtures of tPA and the potential lead compounds are subjected to binding to misfolded protein together reveals also drug candidates that act on the binding site of tPA for misfolded protein.

Materials & Methods

Cloning and Expression of Recombinant Human BiP

The human BiP gene except the signal peptide encoding region was obtained from Geneart (Germany). The gene was extended in a way that the transcribed protein contains a carboxy-terminal extension with amino-acid sequence KSKSKSMMAA (SEQ ID NO:5), for purposes related to couplings to matrices. A BamHI restriction site was added to the 5' region, a NotI restriction site to the 3' region. The gene was supplied in a vector and digested with BamHI and NotI for ligation in the PABC674 expression vector of the local Expression Facility Utrecht (The Netherlands). Expression of BiP in this vector results in addition of a carboxy-terminal His-tag and a carboxy-terminal FLAG-tag. For expression, 2 µg of vector with BiP was transiently transfected in HEK 293E cells. Cells were allowed to grow for 4 days. Cell culture supernatant comprising BiP was used for binding studies.

Materials for Analysis of IgIV

Human broad spectrum immunoglobulin G (IgG) antibodies, referred to as "intravenous Ig" ("IVIg" or "IgIV"), "gammaglobulin," "intravenous immune globulin," "intravenous immunoglobulin," or otherwise, were obtained from the local University Medical Center Utrecht Pharmacy. Octagam from Octapharma (Octapharma International Services N.V., Brussels, Belgium; dosage 2.5 gr. in 50 ml, was used. Octagam is supplied as a ready-to-use solution comprising 50 mg/ml IgIV. Other components are 100 mg/ml maltose and less than 5 µg/ml Triton X-100 and less than 1 µg/ml tri-n-butyl phosphate. IVIg is stored at 4° C. According to the manufacturer, Octagam mainly consists of IgGs ($\geq$95%), with a minor IgA fraction ($\leq$5%). The distribution over the four IgG isotypes is: IgG1, 62.6%; IgG2, 30.1%; IgG3, 6.1%; IgG4, 1.2%. Octagam is used at room temperature. Solutions were kept at room temperature for at least 30 minutes before use.

For ELISAs, Microlon high-binding plates (Greiner Bio-One GmbH, Frickenhausen, Germany; catalogue number 655092) were used. Antibodies used were goat anti-human IgG-alkaline phosphatase (Biosource Int., Camarillo, Calif., USA; catalogue number AHI0305), peroxidase-conjugated rabbit anti-mouse immunoglobulins (RAMPO, catalogue number P0260, DAKOCytomation, Glostrup, Denmark), peroxidase-coupled swine anti-rabbit immunoglobulins (SWARPO, catalogue number P0217, DAKOCytomation), rabbit polyclonal anti-human albumin antibody A-0001 (DAKOCytomation), rabbit polyclonal anti-human hemoglobin antibody A-0118 (DAKOCytomation)) and murine monoclonal hybridoma anti-glucose-6-phosphate glycated human fibronectin antibody 4B5 ($^2$). In ELISAs, binding of alkaline phosphatase conjugated antibodies was assessed using p-nitrophenyl phosphate disodium 6*$H_2O$ (Sigma-Aldrich, St. Louis, Mo., USA; Phosphatase substrate catalogue number 104), and binding of peroxidase-conjugated antibodies was assessed using 1,2-phenylenediamine ("OPD," Merck, Darmstadt, Germany; catalogue number 1.07243.0050).

Inhibition studies using an ELISA set-up were performed using concentration series of Congo red (Aldrich, Milwaukee, Wis., USA; catalogue number 86, 095-6), Thioflavin T (Sigma, St. Louis, Mo., USA; catalogue number T3516), Thioflavin S (Sigma; catalogue number T1892), tissue-type plasminogen activator (tPA, Actilyse, Boehringer-Ingelheim, Alkmaar, The Netherlands), or a truncated form of tPA (K2P tPA, Rapilysin, Boehringer-Ingelheim, Alkmaar, The Netherlands) lacking three amino-terminal domains including the fibronectin type I domain, or alternatively designated as finger (F) domain.

Antigens used in IgIV binding ELISAs were bovine serum albumin (BSA, fraction V, catalogue number A-7906, initial fractionation by heat shock, purity $\geq$98% (electrophoresis), remainder mostly globulins, Sigma-Aldrich, St. Louis, Mo., USA), human hemoglobin (Hb, Sigma-Aldrich; catalogue number H7379), and their advanced glycated end products-modified counterparts BSA-AGE and Hb-AGE (see below).

Glycation of Proteins

Glycation of albumin and Hb was performed as follows. For preparation of BSA-AGE, 100 mg ml$^{-1}$ of albumin was incubated with phosphate-buffered saline (PBS, 140 mM sodium chloride, 2.7 mM potassium chloride, 10 mM disodium hydrogen phosphate, 1.8 mM potassium di-hydrogen phosphate, pH 7.3) containing 1 M of D-glucose-6-phosphate disodium salt hydrate (anhydrous) (g6p, ICN, Aurora, Ohio, USA) and 0.05% m/v $NaN_3$, at 37° C. in the dark. The solution was glycated for 70 weeks. Human Hb at 10 mg/ml was incubated for 58 weeks at 37° C. with PBS containing 1 M of g6p and 0.05% m/v of $NaN_3$. After incubations, albumin and Hb solutions were extensively dialyzed against distilled water (BSA-AGE) or against 50 mM Tris, 150 mM NaCl, pH 7.3, and, subsequently, aliquoted and stored at −20° C. Protein concentrations were determined with Advanced protein-assay reagent ADV01 (Cytoskeleton, Denver, Colo., USA).

(Heat-)Denaturation

Purified chicken ovalbumin (OVA, Sigma; catalogue number A5503) in PBS was heated for five cycles in PCR cups in a PTC-200 thermal cycler (MJ Research, Inc., Waltham, Mass., USA). In each cycle, protein was heated from 30 to 85° C. at a rate of 5° C./minute. Heat-denatured OVA (DOVA) solutions were stored at −80° C. Lyophilized human amyloid-β(1-40) with E22Q mutation "Dutch type" (Peptide facility, Dutch Cancer Institute, Amsterdam, The Netherlands) was first dissolved in 1,1,1,6,6,6-hexafluoro-2-propanol and trifluoroacetic acid in a 1:1 volume ratio. Solvent was evaporated under an air stream and Aβ was dissolved in $H_2O$ to a final concentration of 1 mg/ml, and stored at room temperature.

Determination of Cross-Beta Structure in Denatured Proteins

To establish that cross-beta structure was induced during the above-mentioned protein treatments, enhancement of Thioflavin T fluorescence or Congo red fluorescence was assessed as well as tPA binding in an ELISA and tPA activation in a chromogenic tPA activation assay. Presence of large protein assemblies in Aβ was visualized using transmission electron microscopy imaging.

Binding of BiP to Misfolded Proteins with Cross-Beta Structure

Proteins at 5 µg/ml were coated for 1 hour at room temperature with agitation, in Microlon high-binding ELISA plates (Greiner) in 50 mM $NaHCO_3$ pH 9.6. Buffer was coated as negative control. A two-fold dilutions series of cell culture supernatant of HEK 293E cells over-expressing BiP was also coated to the plate for anti-FLAG-tag antibody control purposes. Plates were washed and blocked with ½*Blocking reagent (Roche). Undiluted cell culture supernatant enriched with 0.1% TWEEN®20 was added to the wells with immobilized protein ligands and incubated for 1 hour at room temperature with agitation. Medium was discarded and the plate was washed with PBS with 0.1% v/v TWEEN®20. Mouse monoclonal anti-FLAG-tag antibody (Sigma, A8592, anti-FLAG M2PO conjugate) was diluted 1000× in PBS/0.1% TWEEN®20 and added to all wells, including those that are coated with cell culture supernatant. After a one-hour incubation at room temperature with agitation and after washing, wells were overlaid with 3000× diluted RAMPO (DAKOCytomation) in PBS/0.1% TWEEN®20. After 30 minutes, the plate was washed and bound peroxidase was visualized with tetramethylbenzidine (TMB, #45.103.20/#45.014.01, Biosource, Nivelles, Belgium). The reaction was stopped after 5 minutes with 10% $H_2SO_4$ in $H_2O$. Absorbance was read at 450 nm.

Inhibition of BiP Binding to Cross-Beta Structure with tPA

In a similar set-up as described above, the influence of 1 µM tPA (Actilyse, Boehringer-Ingelheim) or 1 µM K2P-tPA, a tPA deletion mutant lacking the N-terminal cross-beta structure binding finger domain, EGF-like domain and first kringle domain (Reteplase, Boehringer-Ingelheim), on binding of BiP to misfolded proteins with cross-beta structure was determined in an ELISA set-up. For this purpose, cell culture supernatant with expressed and secreted BiP was diluted threefold in PBS/0.1% TWEEN®20/10 mM ε-amino caproic acid, and either tPA or K2P-tPA was added whereas PBS was added to a control sample. Hb-AGE, Hb, BSA-AGE, BSA and buffer were coated. The threefold diluted cell supernatants were applied to the ELISA plate in duplicates and BiP binding was subsequently measured as described above. Coat efficiency was checked with specific anti-AGE antibody, anti-albumin antibody and anti-Hb antibody.

Enzyme Linked Immunosorbent Assay for Testing of IgIV Binding to Misfolded Proteins Binding of IgIV was determined using an enzyme linked immunosorbent assay (ELISA) set-up. For this purpose 50 µl/well of potential ligands at indicated concentrations or coat buffer only for control and background measurement purposes, were coated overnight at 4° C., with motion, in 50 mM NaHCO$_3$ pH 9.6. Glycated albumin and Hb (BSA-AGE and Hb-AGE), control BSA and control Hb were coated at 5 µg/ml. The BSA and Hb controls were prepared freshly by dissolving lyophilized proteins at 1 mg/ml in PBS upon resuspending by pipetting, followed by a 30-minute period at the roller bank, at room temperature. The protein solutions were centrifuged for 10 minutes at 16,000*g and diluted in coat buffer. Coat controls were performed with anti-glycated protein antibody, anti-albumin antibody, anti-Hb antibody. The alkaline phosphatase-conjugated anti-human Ig antibodies were controlled by coating the IgIVs and overlaying them the secondary antibodies. After coating the plates were washed twice with 50 mM Tris-HCl pH 7.3, 150 mM NaCl, 0.1% v/v TWEEN®20, and blocked with 175 µl/well Blocking reagent (Roche Diagnostics, Almere, The Netherlands; catalogue number 11112589001), for 1 hour at room temperature, with motion. Plates were washed twice and incubated in triplicate with indicated antibodies dilution series, plasma dilution series or controls, including binding buffer only, in the absence or presence of putative inhibitors, in binding buffer; PBS/0.1% v/v TWEEN®20, at 50 µl/well, for 1 hour at room temperature, with constant motion. After four wash cycles, secondary antibodies were added to the wells, 50 µl/well, for 45 minutes at room temperature, with motion. RAMPO and SWARPO were used at 2000 times dilution, goat anti-human IgG antibodies were diluted 3000 times, goat anti-human IgM antibodies were diluted 1000 times. After five washes with wash buffer followed by two washes with PBS, binding of antibodies was assessed. For alkaline phosphatase conjugated secondary antibodies p-nitrophenyl phosphate (600 µg/ml) in DEA buffer pH 9.8 (10% v/v diethanolamine in H$_2$O, with 240 µM MgCl$_2$.6H$_2$O, pH adjusted with HCl) was used at 100 µl/well, for about 5 minutes. The reaction was stopped by adding 50 µl/well of 2.4 M NaOH in H$_2$O. After 5 minutes absorbance was read at 405 nm. For peroxidase-conjugated RAMPO and SWARPO, OPD (1.3 mg/ml) in 50 mM citric acid/100 mM Na$_2$HPO$_4$/0.06% v/v H$_2$O$_2$ pH 5 was used at 100 µl/well, for about 5 minutes. The reaction was stopped by adding 50 µl/well of 2 M H$_2$SO$_4$ in H$_2$O. After 5 minutes absorbance was read at 490 nm. Each experiment has been performed at least twice. To test whether amyloid-like cross-beta structure binding compounds and controls (see ref.[1] and patent application WO2004/004698) interfere with IgIV binding to cross-beta structure ligands, concentration series of the potential inhibitors were tested in the presence of a suboptimal IgIV concentration. For this purpose stock solutions used of tPA, K2P tPA, Congo red, Thioflavin S (ThS) and Thioflavin T (ThT) were 3.7 mg/ml, 1.1 mg/ml, 10 mM, 10 mM and 10 mM, respectively. The influence of tPA and K2P tPA was tested in the presence of 10 mM ε-amino caproic acid, to avoid binding of the kringle2 domain of tPA and K2P tPA to lysine- and arginine residues (tPA binding to amyloid-like structures is mediated by its finger domain, that is lacking in truncated K2P tPA; the kringle2 domain binds to exposed side chains of lysines and arginines). Binding buffer and K2P tPA serve as negative controls in these inhibition studies. Separately, similar inhibition studies were performed with immobilized Aβ or BSA-AGE, a suboptimal concentration of tPA (see ref.[4, 1]) and concentration series of Congo red or ThT. Data reduction was performed as follows. Triplicates were averaged and standard deviations calculated. Background signals obtained with buffer-coated wells were subtracted (binding of primary antibody to empty wells), as well as background signals obtained with wells in which the primary antibodies were omitted (binding of secondary antibody to coated ligands).

Materials for Screening of Small Compounds for their Ability to Interact with Misfolded Proteins Microlon high binding plates, (Greiner) NR 655092
Blocking Reagent, (Roche)
tPA Actilyse, (Boehringer Ingelheim)
Anti-tPA 374B, (American Diagnostica) Prod. No. 374B
Anti-tPA 385R, (American Diagnostica) Prod. No. 385R
RAMPO, 1,3 g/L (DakoCytomation) product number P0260
SWARPO, 1,3 g/L (DakoCytomation) product number P 0217
TMB (TebuBio)
Congo red (Aldrich Chemicals, Germany), cat. Number 86,095-6
Thioflavin T (Sigma-Aldrich, Germany), cat number T-3516
229 small compounds, 250 µg each at 5 mg/ml in DMSO (TimTec, Newark, Del., USA, www.timtec.net; see Table 4)
5 mg of each of the following lyophilized compounds:
 1. Dehydroglaucine derivative (TimTec, Newark, Del., USA, www.timtec.net)
 2. Thaliporphine (TimTec)
 3. Ammophedrine HBr (TimTec)
 4. Isoboldine (TimTec)
 5. compound 5 (no name) (TimTec)
 6. compound 6 (no name) (TimTec)
 7. compound 7 (no name) (TimTec)
 8. haematein, MW=300.27 g/mol (Fluka, Sigma-Aldrich, Steinheim, Germany), catalogue number 51230 (10 gr.)
 9. DXS500k, dextran sulphate sodium salt, MW ~500,000 g/mol, free SO$_4$ less than 0.5% (Amersham Pharmacia Biotech AB, Uppsala, Sweden), catalogue number 17-0340-01 (100 gr.)
 10. ellagic acid hydrate (Sigma-Aldrich Chemie GmbH, Steinheim, Germany), catalogue number 37,274-9 (10 gr.)
 11. corynanthine (Sigma Chemical Co., St. Louis, Mo., USA), catalogue number C-3255 (5 gr.)
 12. orcein, (Sigma-Aldrich, St. Louis, Mo., USA), catalogue number O7380 (5 gr.)

ELISA: Binding of tPA to Glycated Hemoglobin, Misfolded Ovalbumin and Amyloid-β

Aim:

Determination of suitable ELISA conditions for testing the influence of small compounds on the interaction between tPA and misfolded protein Hb-AGE. Parameters:
1) coat concentration of Hb-AGE (glucose-6-phosphate modified human hemoglobin);
2) concentration of tPA.

Experimental Procedure in Brief

1. Hb-AGE coat at 0/0.1/0.2/0.4/0.8/1.6/3.2/6.4/12.8/25.6 µg/ml in Coat buffer (100 mM NaHCO$_3$, pH 9.6) on a Greiner Microlon high-binding plate, for 30 minutes at room temperature, with agitation. Coat buffer in control wells.

2. wash three times with 50 mM Tris, 150 mM NaCl, pH 7.3 (TBS)/0.1% TWEEN®20 (wash buffer)

3. Block all wells with 300 µl 0.5*recommended concentration Roche blocking reagent for 30 minutes at room temperature, with agitation 4. wash twice 5. Stock tPA: 50 µM Actilyse (Boehringer Ingelheim). tPA incubation at 0/0.2/0.6/1.8 nM in PBS-T buffer with 0.1% TWEEN®20, 10 mM ε-amino caproic acid and 10% (v/v) dimethylsulfoxide (DMSO).

6. Incubate for 30 minutes at room temperature, with agitation 7. wash five times with TBS/0.1% TWEEN®20

8. Fill wells with mouse monoclonal anti-tPA antibody 374B (American Diagnostica) used 1000× diluted in PBST 9. Incubate for 30 minutes at room temperature, with agitation 10. wash five times with TBS/0.1% TWEEN®20

11. Fill wells with 3000× diluted horse radish peroxidase-labeled polyclonal rabbit anti-mouse antibody (RAMPO, DAKOCytomation)

12. Incubate for 20 minutes at room temperature, with agitation

13. Wash five times with TBS/0.1% TWEEN®20

14. Wash twice with PBS

15. Stain with 100 µl TMB, stop with 50 µl $H_2SO_4$

16. Read absorbance at 450 nm

For similar ELISAs with heat-denatured ovalbumin (DOVA) and amyloid-β(1-40) E22Q, 1, 3 and 9 µg/ml DOVA or Aβ was coated and overlaid with 0/1/3/9/27/81 nM tPA.

ELISA: Binding of tPA to Glycated Hemoglobin; Influence of Congo Red and Thioflavin T Determination of the influence of amyloid-binding dyes Congo red (CR) and Thioflavin T (ThT) on the binding of a suboptimal concentration of tPA to immobilized glycated hemoglobin (glucose-6-phosphate advanced glycation end-product modified hemoglobin, Hb-AGE). Parameters in these assays: concentration series of CR or ThT with a fixed concentration of tPA, in PBS-0.1% (v/v) TWEEN®20-10 mM ε-amino caproic acid (εACA)-10% v/v dimethylsulfoxide (DMSO). The εACA is used to avoid binding of tPA to ligands via the tPA Kringle2 domain. The DMSO is added in order to obtain the suitable reference for tPA binding, because in subsequent experiments the small compounds tested are all dissolved in DMSO and applied in the analyses in a tenfold diluted manner.

Experimental Procedure in Brief

1. Hb-AGE coat at 1.25 µg/ml in Coat buffer (100 mM $NaHCO_3$, pH 9.6) on a Greiner Microlon high-binding plate (catalogue number 655092), for 30 minutes at room temperature, with agitation. Coat buffer in control wells.

2. wash three times with 50 mM Tris, 150 mM NaCl, pH 7.3 (TBS)/0.1% TWEEN®20 (wash buffer)

3. Block all wells with 300 µl 0.5*recommended concentration Roche blocking reagent for 30 minutes at room temperature, with agitation 4. wash twice 5. Stock tPA: 50 µM Actilyse (Boehringer Ingelheim). tPA incubation at 1 nM in PBS-T buffer with 0.1% TWEEN®20, 10 mM ε-amino caproic acid and 10% (v/v) dimethylsulfoxide (DMSO) with ThT and CR concentrations of 1000/333/111/37/12.3/4.1/1.4/0 µM, respectively.

6. Incubate for 30 minutes at room temperature, with agitation 7. wash five times with TBS/0.1% TWEEN®20

8. Fill wells with mouse monoclonal anti-tPA antibody 374B (American Diagnostica) used 1000× diluted in PBST 9. Incubate for 30 minutes at room temperature, with agitation 10. wash five times with TBS/0.1% TWEEN®20

11. Fill wells with 3000× diluted horse radish peroxidase-labeled polyclonal rabbit anti-mouse antibody (RAMPO, DAKOCytomation)

12. Incubate for 20 minutes at room temperature, with agitation

13. Wash five times with TBS/0.1% TWEEN®20

14. Wash twice with PBS

15. Stain with 100 µl TMB, stop with 50 µl 10% $H_2SO_4$

16. Read absorbance at 450 nm 17. analyze optimal conditions for maximum inhibition of tPA binding to misfolded proteins by Congo red and maximum stimulation of tPA binding to misfolded proteins by Thioflavin T.

ELISA: Binding of tPA to Glycated Hemoglobin, Heat-Denatured Misfolded Ovalbumin and Amyloid-β; Influence of Small Compounds Determination of the influence of small compounds on the binding of a suboptimal concentration of tPA to a refined concentration of immobilized Hb-AGE. Parameter: a fixed concentration of tPA, in PBS with 0.1% (v/v) TWEEN®20, 10 mM εACA and 10% DMSO, mixed separately with the individual small compounds. The small compound library is depicted in Table 4. As a positive control, tPA in binding buffer with 10% DMSO was used. This binding was set to 100% and all values obtained after co-incubations of Hb-AGE with tPA with the small compounds, were scaled accordingly. Binding experiments were performed in single wells per compound, in a duplicate experiment. Binding data obtained with this duplicate experiment was averaged. Enhancement of tPA binding was arbitrarily set to values >100%. Inhibition of tPA binding to misfolded Hb-AGE was arbitrarily set to values smaller than 50%. With the chosen experimental lay-out, it cannot be distinguished whether small compounds influence the interaction between tPA and Hb-AGE by binding to Hb-AGE only or by binding to tPA only or by binding to both tPA and Hb-AGE.

In a next series of experiments, the ability of the selected compounds that interact with tPA and/or Hb-AGE, to bind to immobilized Hb-AGE, heat-denatured misfolded ovalbumin and amyloid-β was analyzed. In a first experiment, the coated misfolded Hb-AGE was first incubated with the selected small compounds listed in Table 6 (potentiators and inhibitors of tPA binding when compounds and tPA are mixed before contacted to Hb-AGE). Compounds were now diluted 10× in PBS/0.1% TWEEN®20 (500 µg/ml compound). After washing, tPA binding was assessed. Compounds that stimulate or that inhibit tPA binding were determined. With this approach a further selection of the compounds was achieved. Now, compounds that at least interact with Hb-AGE are selected. With the selection, similar binding assays are performed with misfolded OVA and Aβ. Finally, concentration series of the selected compounds are used in the binding studies.

Experimental Procedure in Brief

1. Hb-AGE coat at 1.25 µg/ml in Coat buffer on a Greiner Microlon high-binding plate, for 30 minutes at room temperature, with agitation. Coat buffer in control wells.

2. wash three times with wash buffer

3. Block all wells with 300 µl 0.5*recommended concentration Roche blocking reagent for 30 minutes at room temperature, with agitation 4. wash twice 5. Stock tPA: 50 µM Actilyse 1) tPA incubation at 0.5 nM (with tenfold compound stocks of 5 mg/ml in DMSO)

2) tPA incubation at 0.5 nM tPA with 1 mM ThT (control) with 10% DMSO 3) tPA incubation at 0.5 nM tPA with 0.5 mM CR (control) with 10% DMSO
6. Incubate for 30 minutes at room temperature, with agitation
7. wash five times with TBS/0.1% TWEEN®20
8. Fill wells with mouse monoclonal anti-tPA antibody 374B, 1000× diluted in PBS/0.1% TWEEN®20
9. Incubate for 30 minutes at room temperature, with agitation
10. wash five times with TBS/0.1% TWEEN®20
11. Fill wells with 3000× diluted horse radish peroxidase-labeled polyclonal rabbit anti-mouse antibody (RAMPO, DAKOCytomation)
12. Incubate for 20 minutes at room temperature, with agitation
13. Wash five times with TBS/0.1% TWEEN®20
14. Wash twice with PBS
15. Stain with 100 µl TMB, stop with 50 µl 10% $H_2SO_4$
16. Read absorbance at 450 nm Compounds were co-incubated with 0.5 nM tPA. Controls: 1 mM ThT with 0.5 nM tPA, 0.5 mM CR with 0.5 nM tPA, 0.5 nM tPA without compound and buffer without tPA. After the first selection round with Hb-AGE and co-incubated tPA and small compounds, next ELISA plates were first pre-incubated with compounds (for 30 minutes) followed by tPA incubation (for 30 minutes). Potent stimulators and inhibitors of tPA binding to Hb-AGE were selected. Selection criteria were: a compound is assigned as an inhibitor of tPA binding when 50% or less of the signal of the control tPA binding to the ligand is observed; a compound is assigned as a stimulator of tPA binding when signals after tPA binding are increased in the presence of compounds, compared with the control tPA binding.

For similar ELISAs with DOVA and Aβ(1-40) E22Q, 1 µg/ml DOVA or Aβ was coated and overlaid with 80 nM tPA. Subsequently, DOVA or Aβ coated wells and buffer-coated control wells were first incubated with 500 µg/ml of the compounds, followed by an overlay with tPA.

The results of the different experiments were analyzed and the most potent stimulators and inhibitors of tPA binding to Aβ, DOVA and Hb-AGE were selected, based on the criteria >100% is stimulated binding of tPA, <50% is inhibited binding of tPA.

Factor XII Activation Assay

Analysis of the influence of human serum albumin (I), ellagic acid and the combination thereof, on activation of factor XII was performed using a chromogenic assay with purified components. For this purpose, in a reaction volume of 60 µl the following components were mixed: 10 µl of 300 µg/ml ellagic acid solution or control buffer, 10 µl of 750 µg/ml I or control buffer, 20 µl of a solution comprising [HEPES-buffered saline, 1.96 µg/ml prekallikrein (Calbiochem), 10 mM $ZnCl_2$, 2.13 µg/ml high molecular weight kininogen (Calbiochem); "PK mix"], 10 µl Chromozyme-PK (Roche, 1 mg/ml aliquot) and 10 µl of a solution comprising 1 mM $ZnCl_2$, HEPES-buffered saline and 4.76 µg/ml factor XII (Calbiochem); "FXII mix." Nunc Immobilizer plates were blocked with PBS with 1% TWEEN®20 for 1 hour at room temperature under constant motion. All reagents were kept on ice throughout preparation of the experiment. The factor XII activating capacity of ellagic acid (Sigma, E-2250, St. Louis, Mo., USA) or I (Cealb, Sanquin, Amsterdam, The Netherlands) alone, and combination thereof, was determined in duplicate. After adding 10 µL of I solution or buffer and 10 µl of ellagic acid solution or buffer to the wells, 20 µL of PK mix was added to each well. Ten µL of kallikrein substrate Chromozyme PK was added to each well, followed by 10 µL of freshly prepared FXII mix. Final I and ellagic acid concentrations are 125 µg/ml and 50 µg/ml. Absorbance was measured at 405 nm at 37° C. for 3 hours with brief shaking every minute.

Thioflavin T Fluorescence of Ovalbumin and Small Compounds Interacting with Misfolded Proteins To establish the enhancement of Thioflavin T fluorescence by ovalbumin preparations, 90 µl of 25 µM ThT-solution in 50 mM Glycine buffer (pH 9.0) was added to 10 µl sample in duplicate wells of black 96-well plates. Heat-denatured ovalbumin at 1 mg/ml in PBS with no addition, DMSO at a final concentration of 1% v/v, or 1 mg/ml of the compounds listed in Table 7, was used. Compound stocks are 100 mg/ml in DMSO. In addition, ovalbumin at 1 mg/ml with the same additions was first heat denatured and subsequently used in the fluorescence assay. Heat denaturation was according to the protocol given above. Fluorescence of duplicates was measured on a Thermo Fluoroskan Ascent 2.5, at 435 nm excitation and 485 nm emission wavelengths.

Aggregation of Platelets Induced by Amyloid-β is Inhibited by Haematein

The influence of amyloid-β(1-40) E22Q Dutch type (Aβ) peptide aggregates with cross-β structure conformation on blood platelet aggregation was tested with washed platelets in an aggregometric assay. Freshly drawn human aspirin free blood was mixed gently with citrate buffer to avoid coagulation. Blood was spun for 15 minutes at 150*g at 20° C. and supernatant was collected; platelet rich plasma (PRP). Buffer with 2.5% trisodium citrate, 1.5% citric acid and 2% glucose, pH 6.5 was added to a final volume ration of 1:10 (buffer-PRP). After spinning down the platelets upon centrifugation for 15 minutes at 330*g at 20° C., the pellet was resuspended in HEPES-Tyrode buffer pH 6.5. Prostacyclin was added to a final concentration of 10 ng/ml, and the solution was centrifuged for 15 minutes at 330*g at 20° C., with a soft brake. The pellet was resuspended in HEPES-Tyrode buffer pH 7.2 in a way that the final platelet number was adjusted to 200,000/µl. Platelets were kept at 37° C. for at least 30 minutes, before use in the assays, to ensure that they were in the resting state.

Aggregation of platelets was monitored in an aggregometer (Chrono-Log Corporation, Havertown, Pa., USA) for 15 minutes at 37° C. with a magnet stirring speed of 900 rpm. First, 270 µl of platelet solution was pipetted in the cuvettes and after 1 minute of stirring, 30 µl of preincubated (5 minutes, RT) Aβ and Hematein solution or control was added. The hematein stock was 10 mg/ml in HEPES-Tyrode buffer. The Aβ stock was 1 mg/ml. For blank readings unstirred HEPES-Tyrode buffer was used. The aggregation is expressed as the percentage of the light transmission (0-100%). As a positive control, synthetic thrombin receptor activating peptide (TRAP) induced platelet aggregation was used. A control experiment was performed to study the influence of the red color of hematein on the light transmission. For this, 4 µM TRAP was added at time 1 minute to the platelets, then hematein was added after 6 minutes of aggregation. The platelets were used for not more than 4 hours after isolation to reduce variations in sensitivity amongst subsequent measurements.

In a second series of experiments, the influence of ellagic acid, another stimulator of the interaction between tPA and misfolded proteins, on Aβ induced platelet aggregation was assessed. Ellagic acid was first dissolved to 100 mg/ml in DMSO, and then further diluted to 1 mg/ml in HBS buffer. Final concentrations of Aβ and ellagic acid in the aggregation assay were 50 µg/ml and 25/50 µg/ml, respectively. In addition, the influence of ellagic acid alone on platelet aggregation was tested. As a control, the influence of 0.08% DMSO on 50 µg/ml Aβ-induced platelet aggregation was analyzed. The 100% DMSO of the ellagic acid stock was diluted 2000 and 4000×, resulting in 0.005% and 0.0025% final DMSO concentrations in the aggregation assay.

Binding of Misfolded Proteins from Solution to Immobilized Small Compounds

To test the ability of the twelve selected compounds (see Table 7) to bind to misfolded proteins, the compounds were immobilized at 10/100/1000 µg/ml in the wells of 96-well Greiner Microlon high binding plates, Nunc amino Immobilizer plates and Nunc Maxisorp plates. Compounds were coated in 100 mM $NaHCO_3$ pH 9.6, 50 µl/well, 1 hour at room temperature with agitation. As a control, wells were coated with buffer only. After blocking of the plates, wells were overlaid with solutions of 0.1/1/10 µg/ml Hb-AGE or 10/100 µg/ml Aβ, in binding buffer (PBS/0.1% TWEEN®20). After washing, binding of Hb-AGE was assessed by overlaying wells with 1 µg/ml hybridoma antibody 4B5, which binds to glycations ([2]), followed by RAMPO. Binding of Aβ was visualized using 500× diluted anti-Aβ antibodies (mouse antibody beta-amyloid Clone 6F/3D #M0872, lot 00003503, DAKOCytomation; β-amyloid (H-43) SC-9129, 200 µg/ml rabbit polyclonal IgG, Santa Cruz Biotechnology) and RAMPO/SWARPO in a 1:1 ratio. Finally, wells were overlaid with $OPD/H_2O_2$ solution, and $H_2SO_4$, before absorbance readings at 490 nm.

Assessment of tPA/Plasmin Activity in the Presence of Small Compounds that Interact with Misfolded Proteins From the ELISA approaches described above it was concluded that eleven of the 290 Natural Small Compounds interact with the binding of tPA in solution to immobilized misfolded protein. In a next analysis it was assessed whether the compounds influence the misfolded OVA mediated activation of tPA/plasminogen. For this purpose, the influence of the compounds on heat-denaturation of OVA was analyzed (see above: Thioflavin T fluorescence measurements). Heated OVA at 1 mg/ml in PBS in the presence or absence of 1 mg/ml of the twelve compounds listed in Table 7 in PBS/DMSO (final DMSO concentration 1%) was used 80-fold or 160-fold or 320-fold diluted (final heated OVA concentration and compound concentration was 12.5 or 6.3 or 3.1 µg/ml; final DMSO concentration was 0.013% and 0.006% and 0.003%). In Costar 2595 ELISA plates, final concentrations tPA and tPA chromogenic substrate S-2765 (Chromogenix, Milano, Italy) were 100 nM and 250 µM, respectively. Protease activity of tPA was followed in time by absorbance readings each minute for 2 hours, at 37° C.

Next, the influence of the twelve compounds on the tPA/plasminogen activating properties of misfolded OVA was analyzed. For this purpose, tPA/plasminogen activation was measured in a kinetic assay with chromogenic plasmin substrate PNAPEP1751 (BIOPEP, Mauguio, France). Concentrations of tPA and plasminogen are 400 pM and 20 µg/ml, respectively. Heated OVA, either in PBS/1% DMSO (positive control), or in the same buffer in the presence of 1 mg/ml of the compounds, was used 40-fold diluted in the assay. Negative control was buffer without OVA. Moreover, influence of 80-fold or 160-fold diluted compounds (stock 1 mg/ml in PBS/1% DMSO) on tPA/plasminogen activation by 80-fold or 160-fold diluted pre-formed heated misfolded ovalbumin (stock 1 mg/ml in PBS) was assessed in the same experimental set-up. In addition, it was assessed whether the compounds interfere with absorbance readings at 405 nm, with converted chromogenic substrate. For this purpose, tPA, plasminogen, DXS500k and substrate PNAPEP1751 were mixed in an Eppendorf cup and warmed at 37° C. until a yellow solution indicated converted substrate by plasmin. The yellow solution is divided over wells of an ELISA plate. Either control buffer (diluted PBS/1% DMSO) or diluted compound stocks was added 1:80 for compounds 2, 3, 4, 7, 11 and 12, and 1:160 for compounds 1, 5, 6, 8, 9 and 10, and absorbance at 405 nm is read. Signals are compared and related to the control.

Transmission Electron Microscopy with Ovalbumin Heated in the Presence of Small Compounds With ovalbumin solutions that were obtained after heating in the presence of PBS or 1 mg/ml of either of the twelve compounds, transmission electron microscopy (TEM) imaging has been performed. For TEM analyses grids were prepared according to standard procedures. Ovalbumin samples at 1 mg/ml were applied to 100-mesh copper grids with carbon coated Formvar (Merck, Germany), and subsequently washed with PBS and $H_2O$. Grids were applied to droplets of 2% (m/v) methylcellulose with 0.4% (m/v) uranylacetate pH 4. After a two-minute incubation, grids were dried on a filter. Images were recorded at 80 kV, at suitable magnifications on a JEM-1200EX electron microscope (JEOL, Japan).

Results

Cloning and Expression of Recombinant Human BiP, and Analysis of BiP Binding to Cross-Beta Structure Cloning and Expression of BiP The human BiP gene was extended with several tags at the carboxy-terminus. The synthetic gene was designed in a way that at the carboxy-terminus sequences were incorporated that may aid in efficient and oriented coupling of the BiP protein molecule to (chromatography) matrices, like, for example, CNBr-Sepharose, NHS-Sepharose, Carboxy-link, any $Ni^{2+}$-based affinity matrix. In addition, the linker sequence may be used to couple labels to the protein molecule, like, for example, NHS-fluorescent probe, or Universal Linkage System-biotin, which can be used for detection purposes and/or for coupling purposes using, for example, Streptavidin-Sepharose. By using the PABC674 vector a FLAG-tag and a His-tag is added to this carboxy-terminus. In total, the original 71 kDa BiP was extended with a linker meant for matrix coupling purposes, KSKSKSMMAA (SEQ ID NO:5), a peptide with sequence DYKDDDDK (SEQ ID NO:6) (FLAG-tag) and HHHHHH (SEQ ID NO:7) (His-tag), with a total molecular mass of 2.9 kDa. Indeed, recombinant BiP has an apparent molecular mass of approximately 75 kDa as seen on a Western blot (not shown). BiP is purified using, for example, $Ni^{2+}$-based affinity chromatography, anion exchange chromatography and/or gel filtration chromatography.

Cross-Beta Structure Binding ELISA with BiP

To assess the binding capacity of BiP towards misfolded proteins comprising a cross-beta structure, misfolded proteins and native controls were immobilized on ELISA plates and overlaid with cell culture supernatant of 293E cells overexpressing recombinant human BiP. BiP binds to glycated hemoglobin (Hb-AGE) and to a lesser extent to coated native hemoglobin (FIG. 4, Panel A). BiP binds to glycated albumin (BSA-AGE) and not to native BSA (FIG. 4, Panel B). From these observations it is concluded that the over-expressed BiP has the ability to bind to misfolded proteins comprising cross-beta structure.

Figure 5:
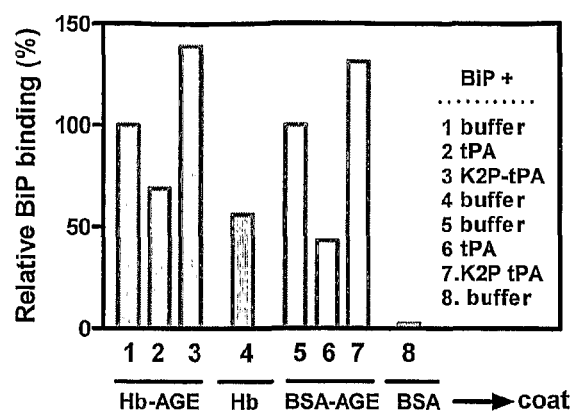
FIG. 5: Binding of BiP to protein-AGE adducts with cross-beta structure is inhibited by tPA. Binding of over-expressed recombinant human BiP in cell culture medium to immobilized Hb-AGE and BSA-AGE is inhibited by tPA and not by K2P-tPA that lacks the cross-beta structure binding finger domain, as determined in an ELISA set-up. Binding of BiP in three-fold diluted cell culture medium is set to 100%.

In a second experiment the influence of multiligand cross-beta structure binding tPA and of K2P-tPA, which lacks the amino-terminal amyloid cross-beta structure binding finger domain, on binding of recombinant BiP to immobilized Hb-AGE, Hb, BSA-AGE and BSA was assessed in an ELISA set-up with coated ligands for BiP (FIG. 5). Binding of BiP occurred in the presence of 10 mM ε-amino caproic acid that prevents the interaction of the kringle2 domain (K2) of tPA and K2P-tPA with free amino groups at the exterior of the ligands. With Hb-AGE, tPA at 1 µM reduces BiP binding from 100% to 69%, whereas K2P-tPA seems to promote BiP binding to some extent. Also some binding of BiP is seen with freshly dissolved Hb, which may comprise a fraction misfolded protein due to, for example, lyophilization. Similar to Hb, BiP binds to BSA-AGE and hardly to BSA. When tPA is introduced in the BiP solution, BiP binding is inhibited for 57%, whereas again K2P-tPA seems to facilitate to some extent BiP binding.

From these experiments it is concluded that recombinant human BiP with a C-terminal extension is expressed and secreted by HEK 293E cells. The BiP is biologically active, based on the observation that BiP binds to misfolded proteins comprising cross-beta structure. The tPA inhibition studies revealed that tPA and BiP compete for the same or similar binding sites on the ligands. That tPA inhibits binding of BiP to proteins comprising cross-beta structure shows the role of cross-beta structure in the interaction of BiP with its misfolded protein ligands.

Figure 6:
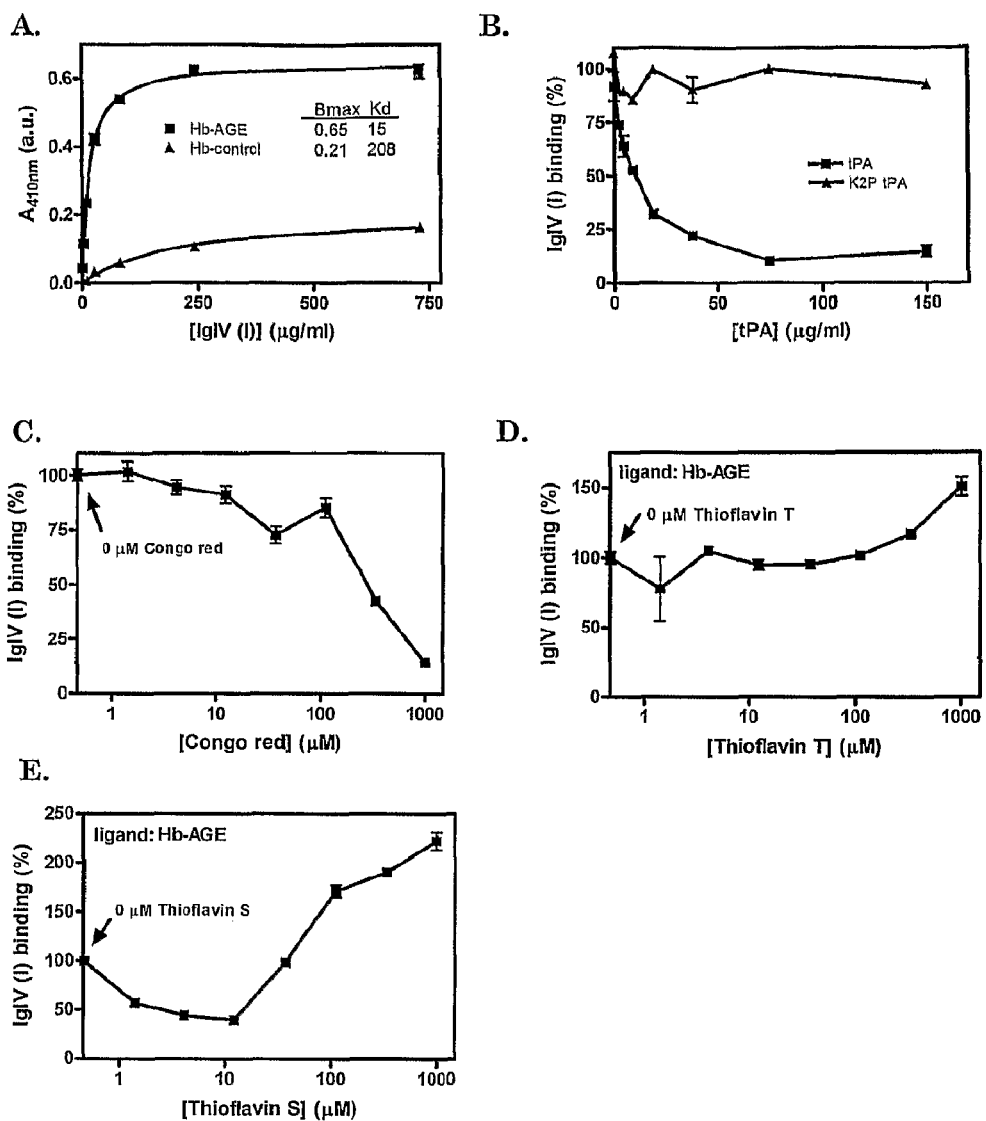
FIG. 6: Binding of IgIV to immobilized protein is inhibited by Congo red and tPA, and stimulated by Thioflavin S or Thioflavin T. In ELISA set-ups, the binding of human IgIV for therapeutical usage was assessed with immobilized glycated proteins. A. Binding of IgIV to coated glycated human hemoglobin (Hb-AGE), and freshly dissolved Hb. B. The influence of tPA and K2P tPA on the binding of 15 μg/ml IgIV to coated Hb-AGE was addressed by adding concentration series of tPA or K2P tPA to the IgIV incubation mixture. Ten mM of εACA was added to the mixture to avoid binding of tPA to exposed lysine or arginine side chains. In a subsequent series of ELISA set-ups binding of IgIV or tPA, a multiligand binding protein with affinity for misfolded proteins that comprise the cross-beta structure fold, was analyzed under influence of concentration series of amyloid-specific dyes Congo red, Thioflavin T and Thioflavin S. C-E. The influence of amyloid-specific dyes Congo red (C.), Thioflavin T (D.) and Thioflavin S (E.) on binding of 15 μg/ml IgIV to immobilized Hb-AGE was addressed by pre-incubating the IgIV with concentration series of the three dyes before adding the solutions to ELISA plates.

Analysis of Binding of IgIV to Misfolded Protein: Inhibition Studies with tPA, Congo Red and Thioflavin IgIV has affinity for misfolded proteins. As a prototype misfolded protein, glycated hemoglobin (Hb-AGE) was used in an ELISA set-up to analyze the parameters that determine the interaction between IgIV and misfolded protein. In FIG. 6, Panel A, binding of IgIV to Hb-AGE is shown. Also some binding is seen to Hb that was freshly dissolved from lyophilized stock, which may result in a misfolded protein fraction, a phenomenon that is observed with lyophilized OVA (not shown). At sub-optimal conditions, tPA fully inhibits the interaction of IgIV with misfolded protein (FIG. 6, Panel B), whereas K2P-tPA that lacks the finger domain that interacts with misfolded protein, does not influence the interaction. Amyloid-binding dye Congo red fully blocks IgIV binding, similar to tPA. In contrast, both Thioflavin T and Thioflavin S enhance the binding of IgIV (FIG. 6, Panels D, E). This activity is also seen with tPA binding to immobilized misfolded protein (not shown). These data altogether show that a screening method for the identification of molecules that interact with misfolded proteins, that uses competitor molecules known for their ability to interact with misfolded protein, can result in newly identified misfolded protein binding molecules, as is shown here for (a fraction of) IgIV.

ELISA: Binding of tPA to Glycated Hemoglobin, Misfolded Ovalbumin and Amyloid-β

Figure 7:
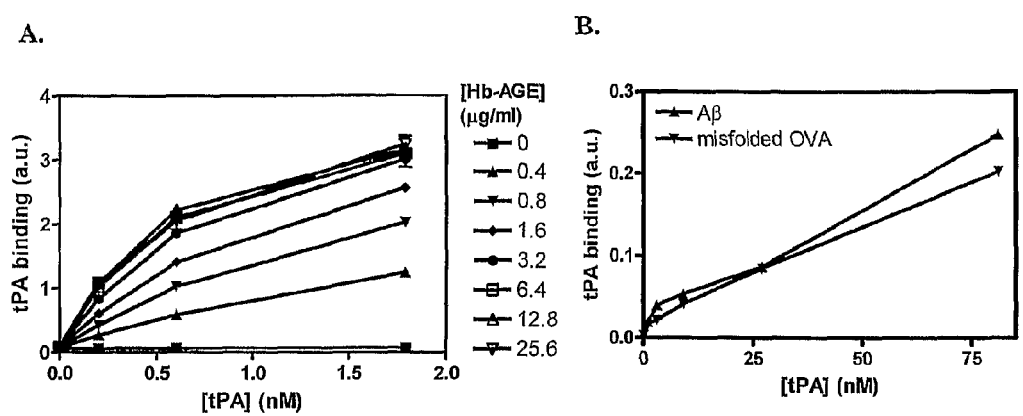
FIG. 7: Determination of sub-optimal parameters for binding of tPA to immobilized misfolded proteins. A. A concentration series of coated Hb-AGE is overlayed with a concentration series of tPA in PBS/0.1% TWEEN®20/10 mM εACA/10% DMSO. B. Heat-denatured misfolded ovalbumin (OVA) and amyloid-β (Aβ) are overlaid with concentration series of tPA.

To be able to analyze the influence of small compounds on the interaction between tPA in solution and immobilized misfolded proteins, first sub-optimal ELISA conditions were determined for the binding of tPA to coated Hb-AGE, amyloid-β and misfolded ovalbumin (FIG. 7). From these binding experiments we deduced that 2.5, 1 and 1 µg/ml Hb-AGE, Aβ and DOVA, respectively, are preferably coated for subsequent competition ELISAs with 1, 80 and 80 nM tPA, respectively, and small compounds (see FIG. 7).

Figure 8:
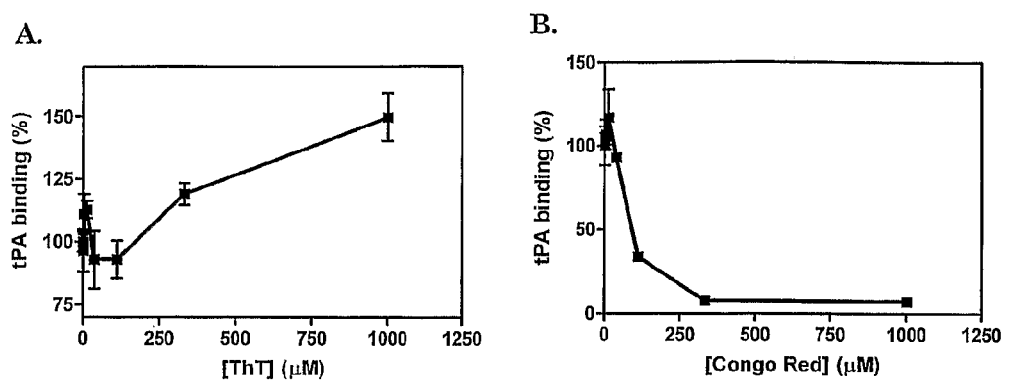
FIG. 8: Influence of amyloid-binding dyes Thioflavin T and Congo red on tPA binding to misfolded protein. A. Influence of Congo red on tPA binding to immobilized Hb-AGE was assessed by including a concentration series of Congo red in the tPA solution. B. Similar to the Congo red experiment, a concentration series of Thioflavin T was included in the tPA solutions.

ELISA: Binding of tPA to Glycated Hemoglobin; Influence of Congo Red and Thioflavin T Before the influence of small compounds on the interaction of tPA with misfolded proteins is analyzed, first optimal conditions are established with two well-known amyloid-binding molecules, Congo red and Thioflavin T (ThT). For this purpose, immobilized Hb-AGE was overlaid with co-incubated tPA and concentration series ThT or Congo red (FIG. 8). From these binding experiments we deduced that Thioflavin T and Congo Red are suitable to be used as controls in subsequent experiments, with concentrations of 1 mM and 0.5 mM respectively. Furthermore, 1.25 µg/ml Hb-AGE preferably are coated for subsequent competition ELISAs with 0.5 nM tPA.

Binding of tPA to Misfolded Proteins; Influence of 229 Natural Compounds

Figure 9:
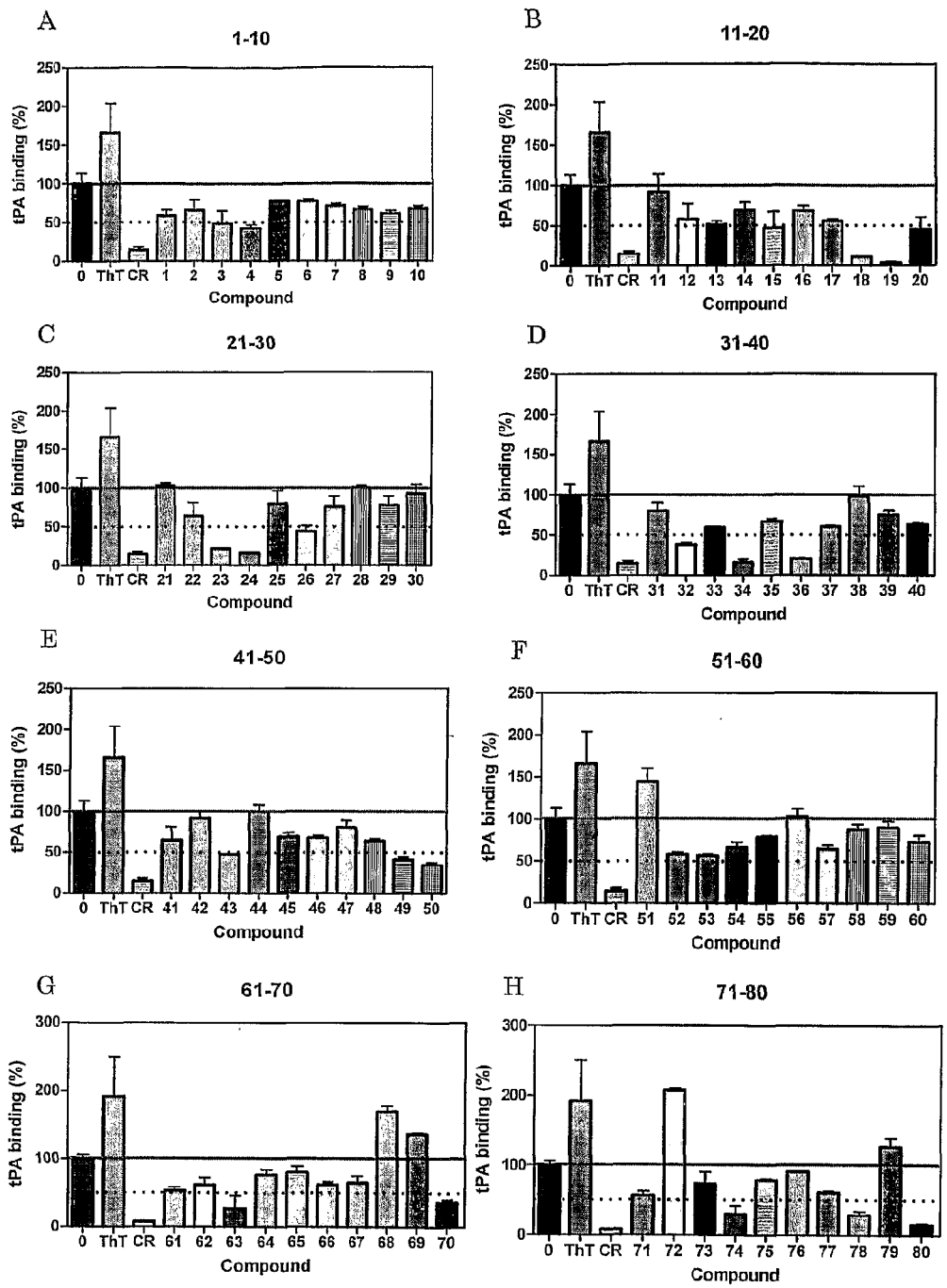
FIG. 9: Influence of small compounds on tPA binding to Hb-AGE. Small compounds were co-incubated with 0.5 nM tPA. Inhibition or stimulation of tPA binding (in %) was determined relative to binding of tPA. [Hb-AGE] is 1.25 μg/nl. [ThT] is 1 mM (positive control for stimulated tPA binding). [Congo red] is 0.5 mM (positive control for inhibited tPA binding). Criteria for stimulated binding by a compound: net absorbance value >100% compared to tPA binding without compound (at least 1.5-fold stimulation). Criteria for inhibited tPA binding by a compound: absorbance value <50% compared to tPA (at least 50% inhibition).
Figure 9:
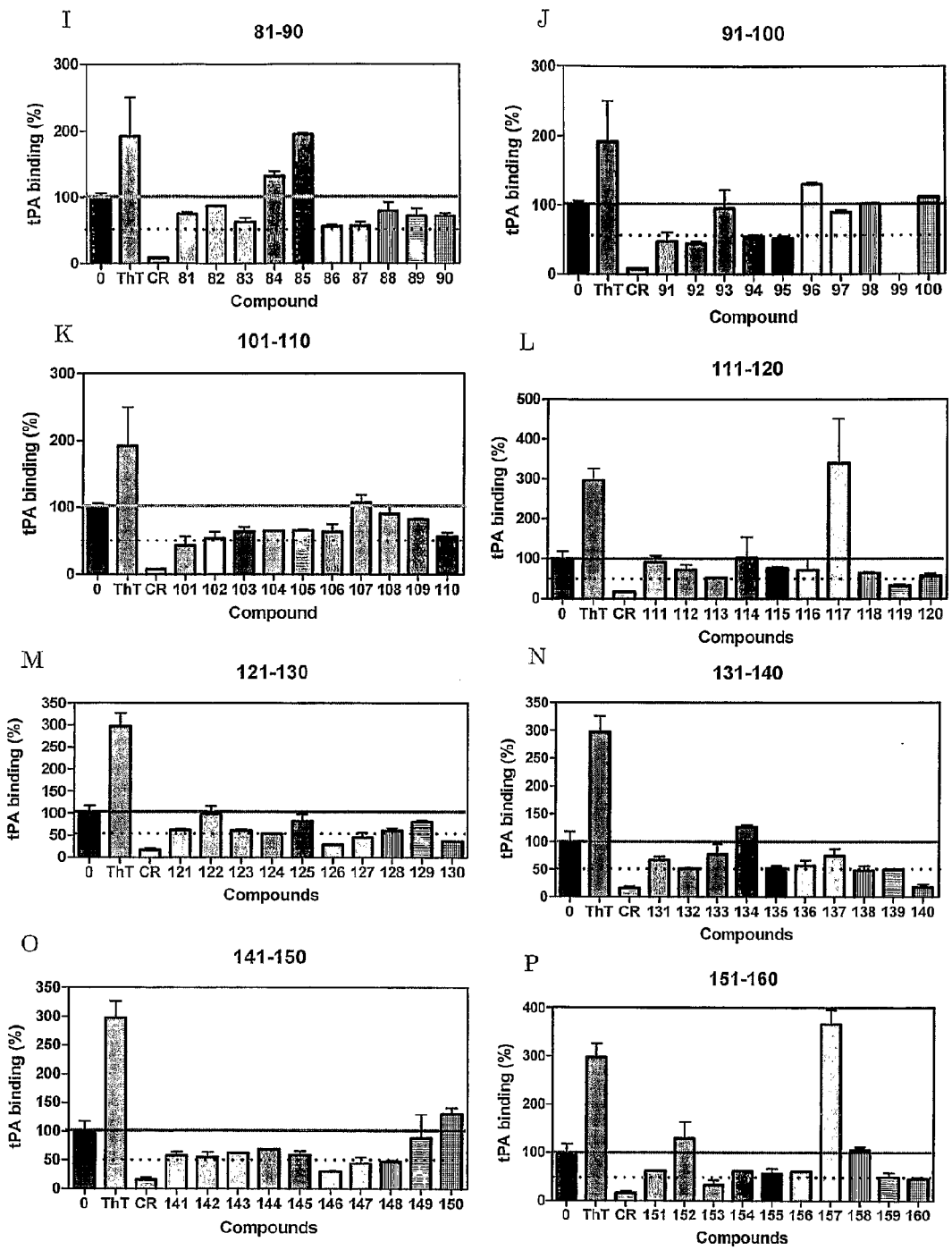
Figure 9:
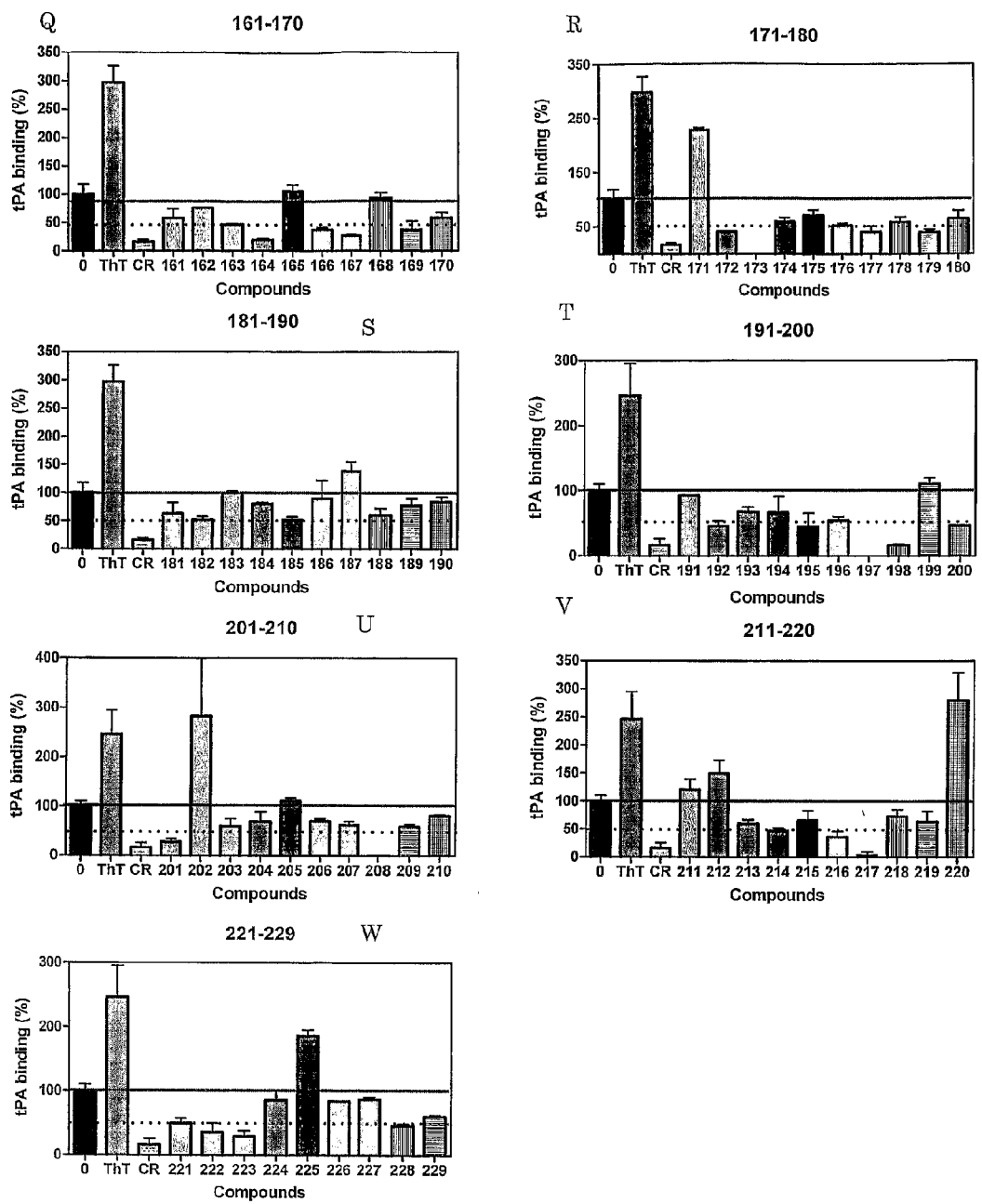
Figure 11:
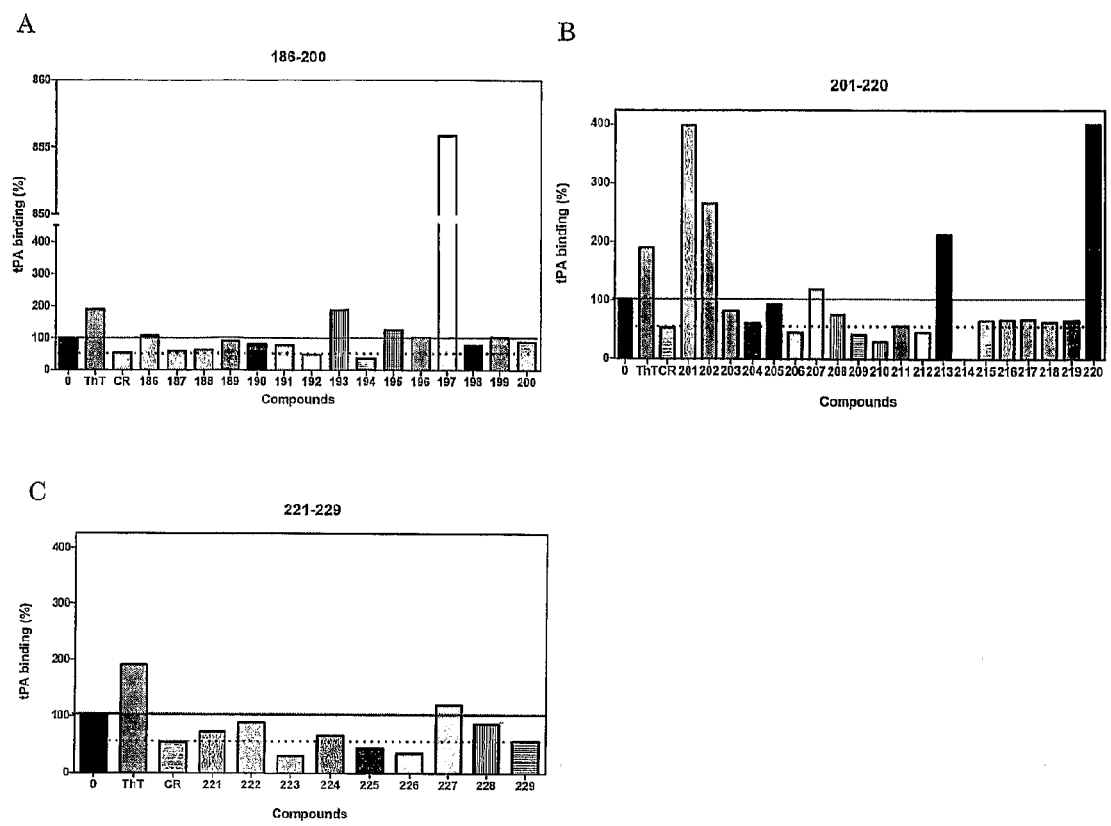
FIG. 11: Binding of 80 nM tPA to 1 μg/ml coated Aβ after pre-incubation of immobilized Aβ with an indicated selection of small compounds at 500 μg/ml.
Figure 13:
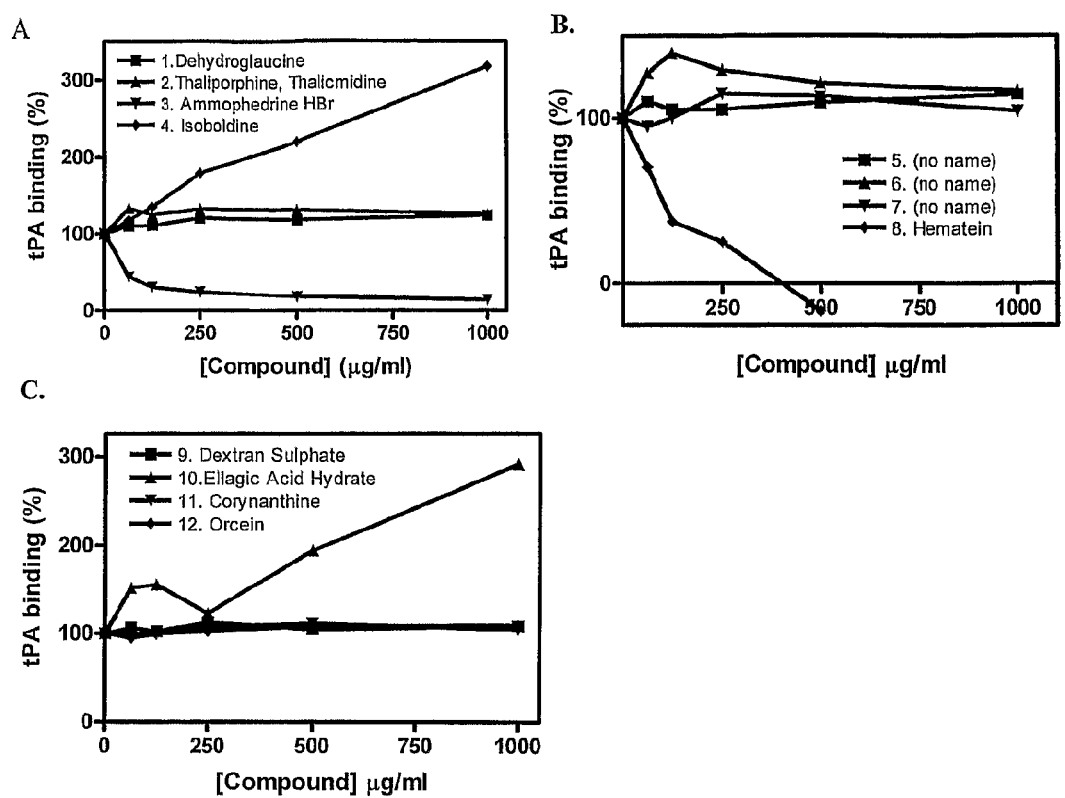
FIG. 13: Binding of tPA to immobilized Hb-AGE that was first overlaid with concentration series of small compounds 1-12, as listed in Table 9.
Figure 14:
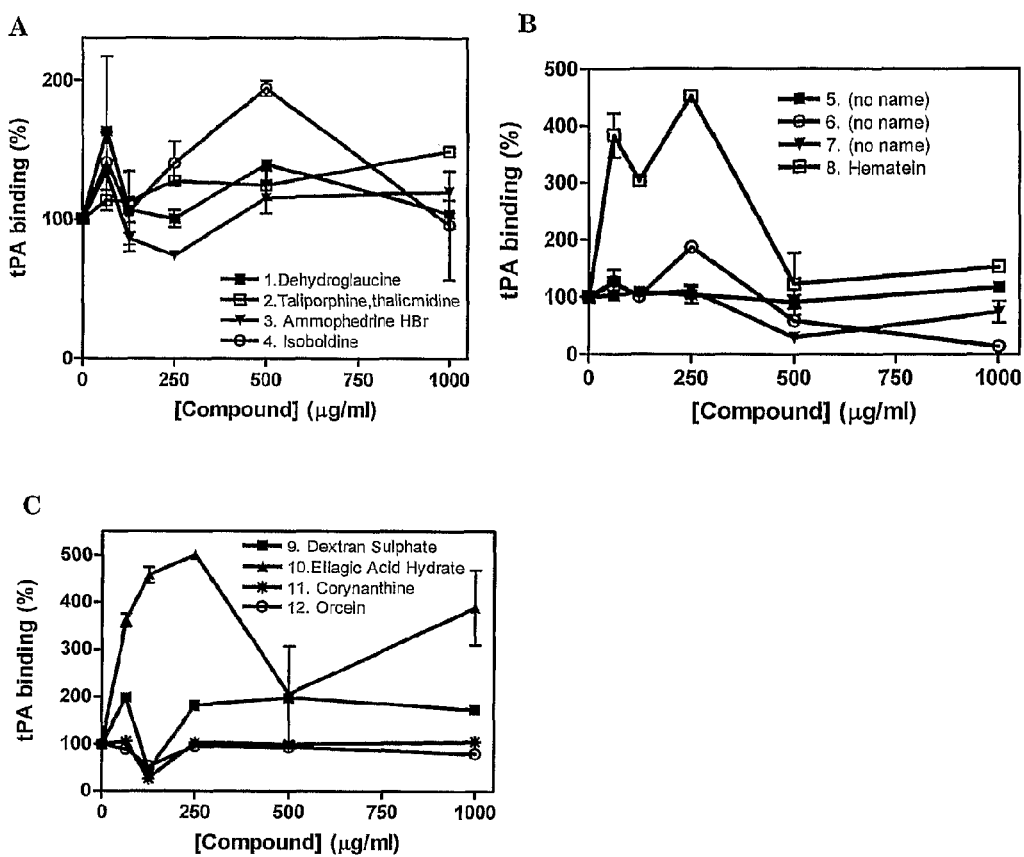
FIG. 14: Binding of tPA to immobilized Aβ that was first overlaid with concentration series of small compounds 1-12, as listed in Table 9.
Figure 15:
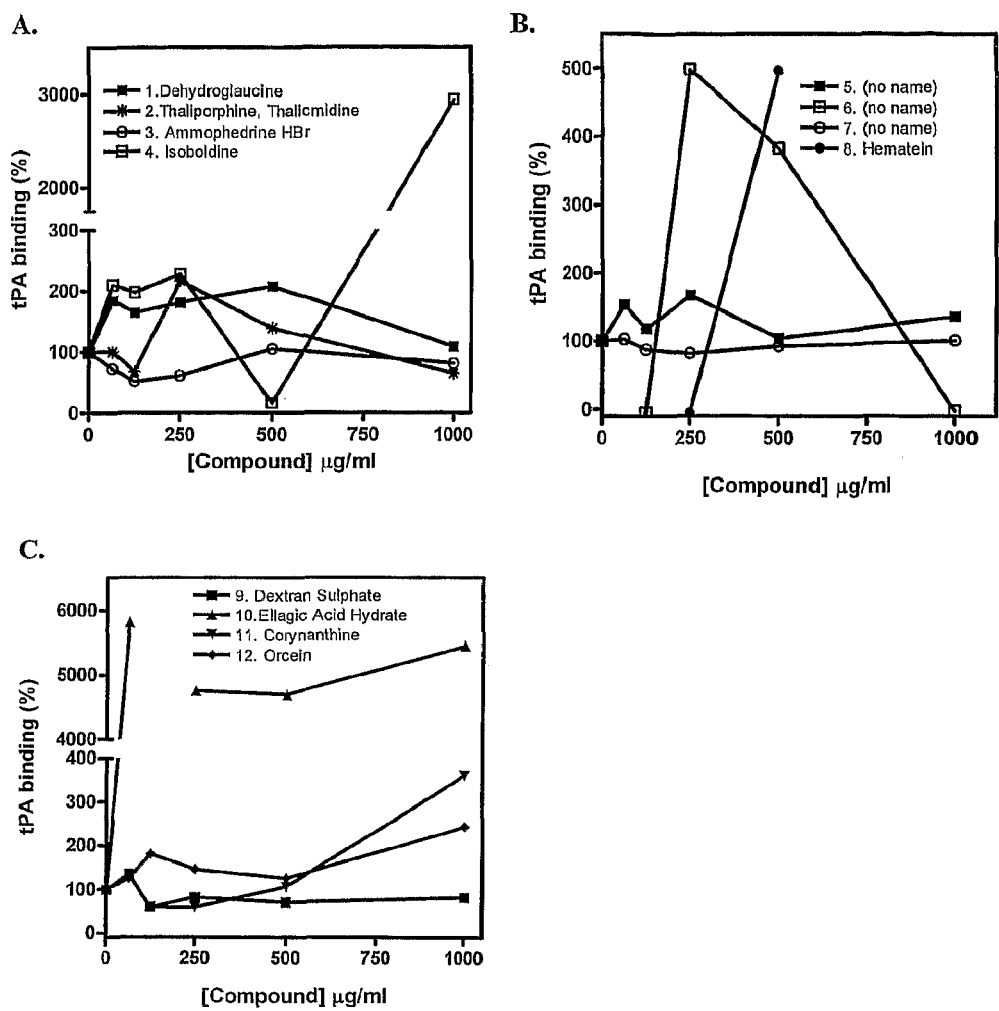
FIG. 15: Binding of tPA to immobilized misfolded ovalbumin that was first overlaid with concentration series of small compounds, as listed in Table 9.

To provide insight into the strength of our methodology for the identification of lead compounds that influence the interaction of natural misfolded protein binding tPA and amyloid-like misfolded proteins, first the influence of small compounds was analyzed twice on the binding of tPA to immobilized Hb-AGE. The compounds were dissolved at 5 mg/ml in DMSO. To be sure that the interaction of tPA with the misfolded protein is not driven by the tPA Kringle domains, 10 mM εACA, a compound that abolishes interaction of Kringle domains with lysine and arginine residues, was always included in the binding buffer. The tPA and the compounds were mixed before applied to an ELISA plate well. The binding of tPA from solution without compound to immobilized Hb-AGE was set to 100%. Compounds that induced scaled binding values >100% were depicted as potentiators of tPA binding; compounds that induced scaled binding values of less than 50% were depicted as inhibitors of the interaction between tPA and misfolded Hb-AGE. See FIG. 9 for all binding data in duplicate. In Table 6, compounds that fulfill the criteria for being a potentiator (23) or inhibitor (48) are summarized. With the used method, compounds that interact with tPA and not necessarily with immobilized misfolded protein, have also been identified from the set of small compounds. Next, selected compounds were first exposed to immobilized Hb-AGE, followed by a tPA incubation. In this way, compounds that directly interact with the immobilized misfolded Hb-AGE are selected. In a similar way, compounds as listed in FIGS. 11 and 12 were first added to wells with coated Aβ or misfolded OVA, followed by tPA overlays (FIGS. 11 and 12). These combined binding studies resulted in a short-list of eleven small compounds that either stimulate binding of tPA to one or more misfolded proteins, or inhibit binding of tPA to one or more of the three misfolded proteins tested. Polymer dextran sulphate 500,000 Da (DXS500k) was added to this group of compounds as a positive control. DXS500k is known for its ability to interact with amyloid-like moieties, its ability to denature protein and for its ability to stimulate factor XII activation in the presence of protein. See Table 7 for the sub-set of twelve compounds, used for further analyses. In a next series of more detailed experiments using triplicate overlays of wells instead of single-well overlays, and using buffer-coated wells for background compound/tPA signal subtraction, concentration series of the twelve compounds were applied to immobilized Aβ, Hb-AGE or misfolded OVA, followed by an overlay with a sub-optimal concentration of tPA (FIGS. 13, 14, 15). These refined analyses revealed to what extent the compounds stimulated or inhibited binding of tPA to at least one of the three misfolded proteins (summarized in Table 9). Based on the results of the above described selections (FIGS. 9, 11-15), the twelve compounds were applied in a series of experiments that reveals more insight into the interaction of the compounds with misfolded proteins. An overview of the compound structures is given in FIG. 10, together with Congo red, Thioflavin S and Thioflavin T, three known dyes for their interaction with amyloid-like proteins.

Factor XII Activation by Albumin and Ellagic Acid

Figure 16:
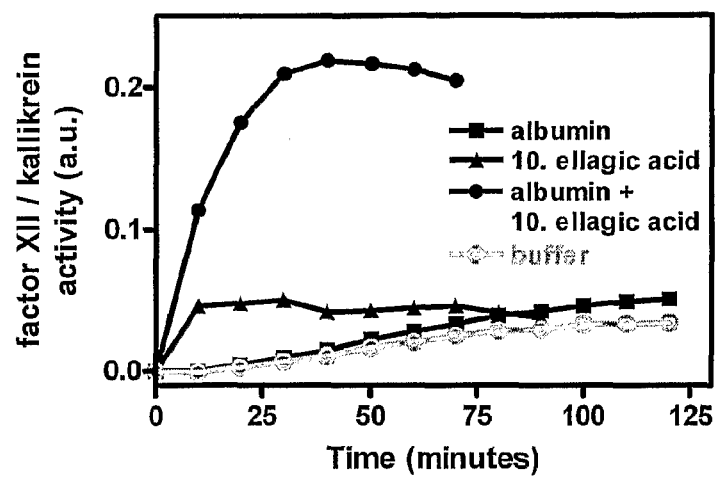
FIG. 16: Activation of factor XII and prekallikrein by ellagic acid is dependent on the presence of protein. When factor XII and prekallikrein are mixed with 50 μg/ml ellagic acid, kallikrein substrate Chromozyme-PK conversion is only observed when in addition 125 μg/ml HSA is included in the assay. Ellagic acid alone at 50 μg/ml or albumin alone at 125 μg/ml result in factor XII/kallikrein activity comparable to control buffer.

Activation of blood coagulation factor XII requires a cofactor in order to let activated factor XII-mediated prekallikrein activation to kallikrein occur. In FIG. 16 it is depicted that human serum albumin or ellagic acid alone are poor activators of factor XII. In contrast, when combined, serum albumin and ellagic acid turn into a potent activator of kallikrein generation. Similar cofactor activity is observed when classical factor XII activators kaolin and dextran sulphate 500,000 Da are used in combination with bovine serum albumin or collagen XVIII fragment endostatin, whereas all four compounds alone hardly activate the enzyme system (not shown). Combined with previous findings that factor XII is activated by misfolded proteins like, for example, amyloid-β, glycated proteins and peptides with amyloid-like conformation, these data point to a role for protein misfolding at the surface of the established factor XII activating molecules. So, native albumin is a poor activator, as is ellagic acid when applied at low enough concentration that does not allow factor XII, prekallikrein or HMWK to denature by exposure to the ellagic acid molecules. When non-activating concentrations of albumin and ellagic acid are mixed and applied in the factor XII activation assay, albumin and ellagic acid turn into potent activators. This shows protein denaturing capacity of ellagic acid, an ability that most likely also occurs when ellagic acid is subjected to an individual.

Figure 17:
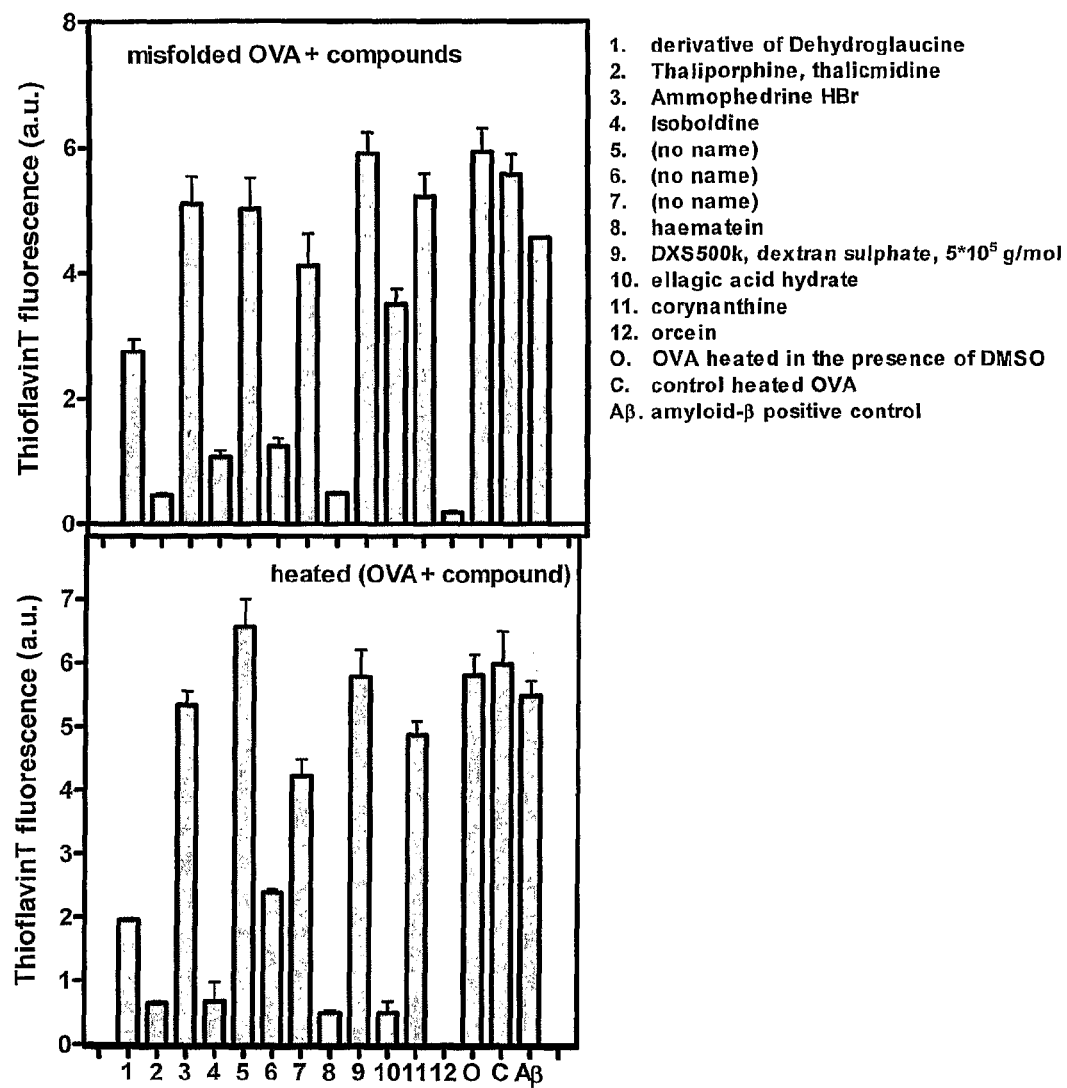
FIG. 17: Influence of small compounds on heat-denaturation of ovalbumin, as assessed by Thioflavin T fluorescence enhancement. The upper figure depicts the enhancement of Thioflavin T fluorescence when pre-formed misfolded ovalbumin is mixed with separately heated small compounds (see legend to the figure). The lower figure depicts the enhancement of Thioflavin T fluorescence when ovalbumin and small compounds are first mixed and then heated.

Thioflavin T Fluorescence of Ovalbumin and Small Compounds Interacting with Misfolded Proteins With the twelve small compounds as given in Table 7, their influence on the interaction of heat-treated ovalbumin (OVA) with Thioflavin T (ThT) was established. For this purpose, OVA was heat denatured at 1 mg/ml and then mixed with the separately heated compounds at 1 mg/ml in DMSO or $H_2O$, as indicated, before applying in the assay (FIG. 17). Alternatively, OVA and the individual compounds were heated together, as well as OVA with or without 1% DMSO, as controls, before applying in the assay (FIG. 17).

Figure 18:
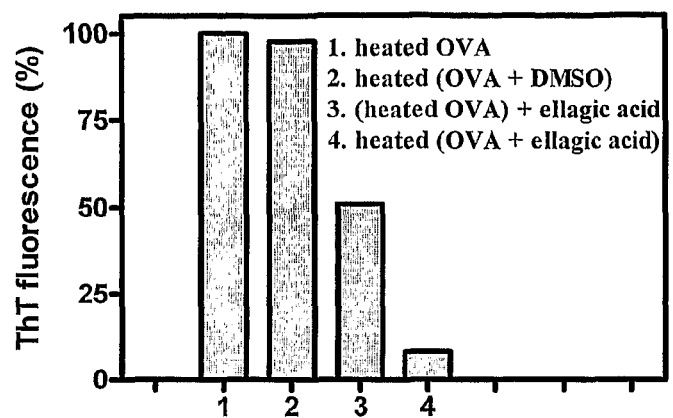
FIG. 18: Ellagic acid hydrate prevents formation of Thioflavin T binding sites in ovalbumin. The influence of ellagic acid hydrate (compound 10) on formation of misfolded ovalbumin [4] and on the interaction of pre-formed misfolded ovalbumin [3] and amyloid-binding dye Thioflavin T is depicted. Controls: [2] is control misfolded OVA in the presence of DMSO and [1] is control misfolded OVA in PBS.

Further detailed information on the activity of ellagic acid hydrate on misfolding of OVA was revealed by heating OVA in PBS/1% DMSO, with or without 1 mg/ml ellagic acid. Ellagic acid alone at 1 mg/ml in PBS/1% DMSO was also heated and either or not added to heated OVA. In FIG. 18 it is depicted that when ellagic acid hydrate is mixed with preformed misfolded OVA, Thioflavin T fluorescence is inhibited for approximately 50%. When ellagic acid hydrate and OVA are heated together, the reduction in Thioflavin T fluorescence enhancement is 90%. These data show the ability of ellagic acid hydrate to prevent formation of amyloid-like protein conformation, that is a binding site for Thioflavin T. Ellagic acid may potently compete for the binding sites with Thioflavin T, as shown when ellagic acid is added to preformed misfolded OVA, and/or ellagic acid can prevent formation of amyloid-like protein conformation, as shown with OVA and ellagic acid that were subjected to heat-denaturation together.

Role of Amyloid-β, Haematein and Ellagic Acid in Platelet Activation

Figure 19:
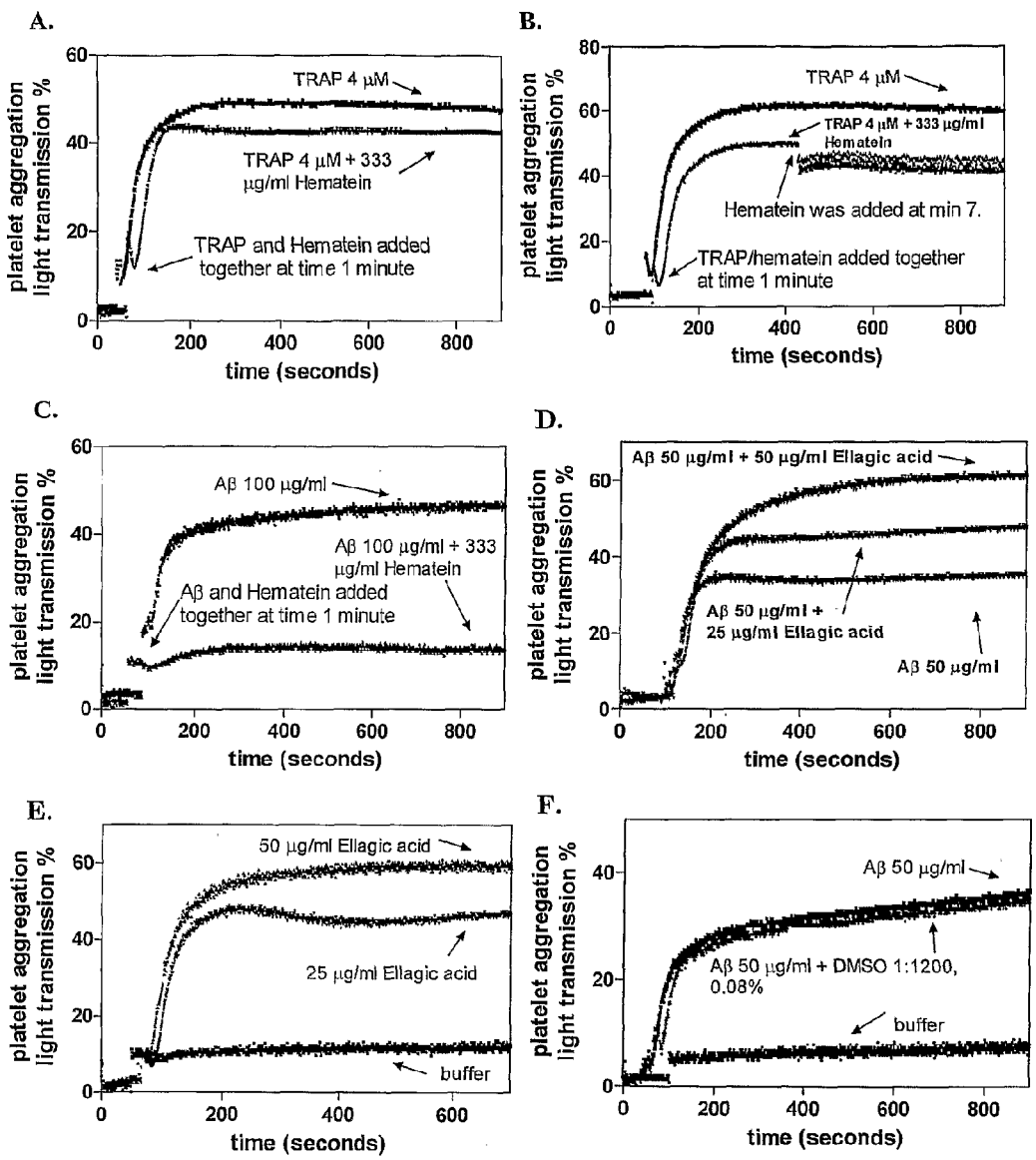
FIG. 19: Blood platelet aggregation under influence of amyloid-β, haematein and ellagic acid. A. Influence of haematein on TRAP-triggered platelet aggregation. TRAP and haematein are pre-mixed and introduced to the platelet suspension together at t=1 minute. B. As A., with also haematein added at t=7 minutes, to assess the influence of haematein on light transmission. C. Influence of haematein on amyloid-β induced platelet aggregation, when Aβ and haematein are pre-mixed before addition to the pre-warmed platelet suspension. D. Influence of ellagic acid hydrate on amyloid-β induced platelet aggregation, when Aβ and ellagic acid are pre-mixed before addition to the pre-warmed platelet suspension. E. Influence of ellagic acid hydrate on platelet activation. F. Control experiment. Ellagic acid hydrate stock of 100 mg/ml is in 100% DMSO. The influence of diluted DMSO on amyloid-β induced platelet aggregation is assessed.

Misfolded proteins induce human blood platelet activation, resulting in aggregation. The influence of compounds 8 (haematein; numbering referring to Table 7) and 10 (ellagic acid hydrate) on Aβ induced platelet aggregation was studied FIG. 19). As a control, first the influence of haematein on TRAP-induced platelet aggregation was studied (FIG. 19, Panels A, B). Haematein at the concentration used reduces platelet aggregation with approximately 10%. When haematein is added to activated and aggregated platelets, its color reduces light transmission with approximately 5%. Activation of platelets by 100 μg/ml Aβ is almost completely blocked by 333 μg/ml haematein, when Aβ and haematein are added together to the platelet suspension (FIG. 19, Panel C). These results show the anti-thrombogenic nature of haematein with respect to amyloid-induced platelet activation.

Ellagic acid hydrate at 25 and 50 μg/ml influences 100 μg/ml Aβ-induced platelet aggregation in an opposite manner. Ellagic acid further enhances amyloid-β triggered aggregation (FIG. 19, Panel D). When 25 or 50 μg/ml ellagic acid is added to the platelets alone (2000 times and 4000 times diluted 100 mg/ml stock), it is a strong inducer of aggregation (FIG. 19, Panel E). In a control experiment, 1200-fold diluted DMSO had no influence on 100 μg/ml Aβ-induced platelet aggregation (FIG. 19, Panel F). Ellagic acid hydrate stock of 100 mg/ml in DMSO was used 2000 or 4000× diluted, so no influence of DMSO on the observed effects is expected. In conclusion, the experiments show that haematein is a potent inhibitor of misfolded Aβ-induced platelet aggregation, whereas ellagic acid hydrate is a potent activator of platelets resulting in their aggregation.

Binding of Misfolded Hb-AGE and Aβ from Solution to Immobilized Small Compounds

To test the ability of the small compounds that influence binding of tPA to immobilized misfolded proteins, to extract misfolded protein from solution when the compounds are fixed to the wells of an ELISA plate, the twelve compounds were coated to Greiner Microlon high-binding 96-well plates, Nunc Maxisorp plates and Nunc amino Immobilizer plates, and overlaid with concentration series of amyloid-β or glycated hemoglobin. Hb-AGE binding is observed with immobilized small compounds 2, 4, 6, 9, 10 (Table 8), as has been observed consistently in duplicate experiments. Aβ binding is observed with immobilized compounds 1, 4, 6, 10 (for compound numbering see FIG. 10 and Table 7). It has been established that: compound 1 (dehydroglaucine derivative) inhibits binding of tPA to Aβ, 2 (thaliporphine, thalicmidine) stimulates binding of tPA to immobilized Aβ and misfolded OVA, 4 (isoboldine) is a stimulator of tPA binding to Aβ, Hb-AGE and DOVA, compound 6 (no name) is a inhibitor of tPA binding to Hb-AGE and 10 (ellagic acid hydrate) is a stimulator of tPA binding to Hb-AGE and DOVA. Therefore, it is concluded that the listed small compounds interact with misfolded proteins that are immobilized in the wells of an ELISA plate, as well as vice versa with the misfolded protein in solution/suspension and the compounds immobilized on ELISA plates. From Table 8 it is clear that different compounds bind differently to ligands, which is dependent on coat concentration, misfolded protein ligand concentration and the type of ELISA plate. The ability of the compounds to extract misfolded protein from solution makes them lead candidates for development of affinity matrices for misfolded proteins, which can be applied for purification methods aimed at depletion of solutions from harmful misfolded proteins.

Figure 20:
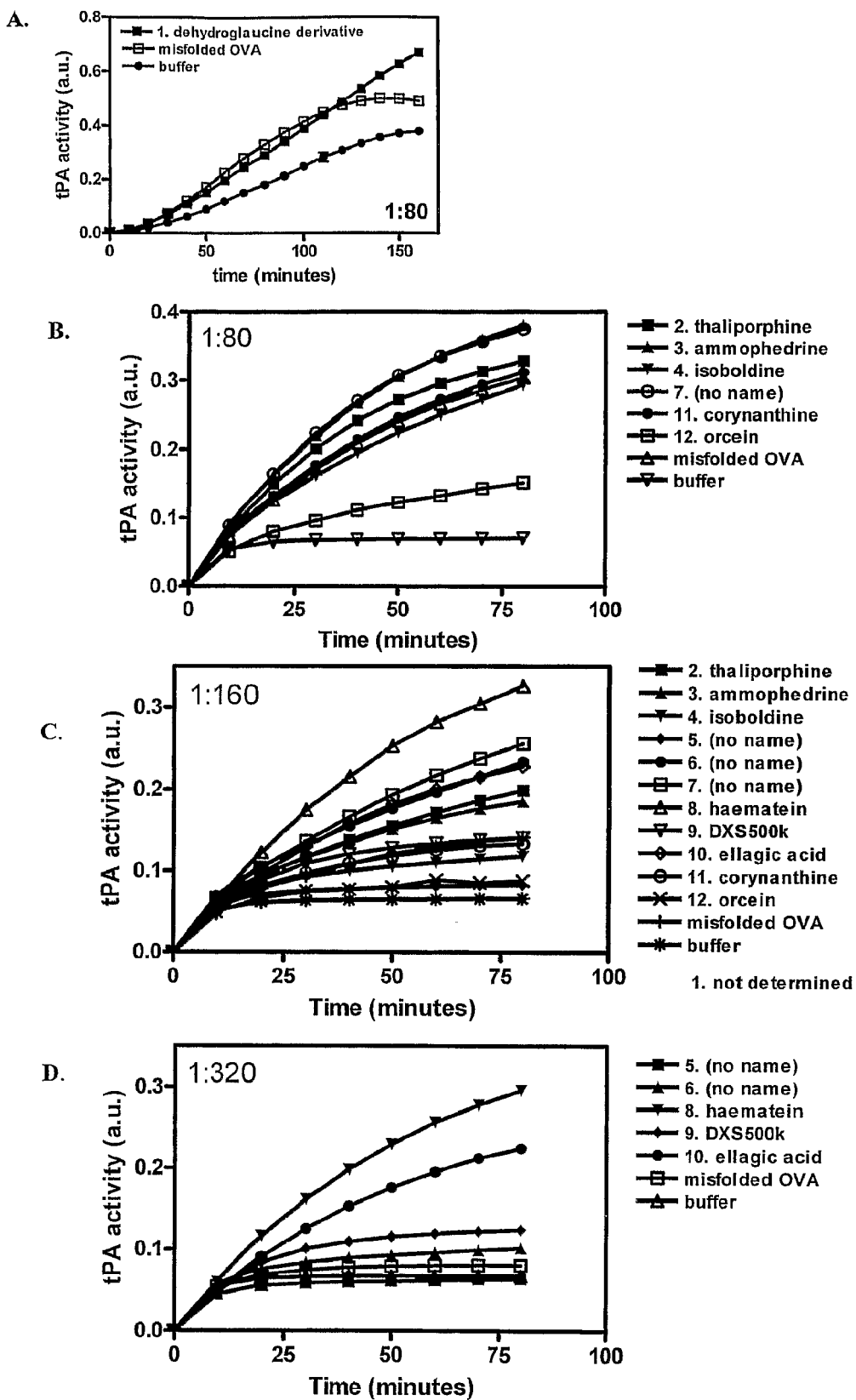
FIG. 20: Influence of ovalbumin heated in the presence of small compounds, on tPA serine protease activity. Ovalbumin, heated in buffer ("misfolded OVA") or in the presence of small compounds (indicated with the compound number according to Table 9 and its name) as indicated, was tested for its influence on the tPA serine protease activity. Stock solutions of 1 mg/ml ovalbumin in buffer or in the presence of 1 mg/ml compound were diluted in the assay as indicated. tPA activity was determined using chromogenic substrate S-2765.

Assessment of tPA/Plasmin Activity in the Presence of Small Compounds that Interact with Misfolded Proteins The influence of OVA that was heated in PBS in the presence of 1% DMSO, or in the presence of 1 mg/ml of compounds 1-12 (See Table 7), on tPA protease activity was analyzed using chromogenic tPA substrate S-2765 (FIG. 20). At 80-fold dilution, misfolded OVA stimulated tPA protease activity when compared to PBS/DMSO buffer control. OVA heated in the presence compounds 1, 2, 3, 4, 7 and 11 (Table 7) did hardly influence tPA stimulation, when compared to misfolded OVA, prepared in PBS/1% DMSO. Heating of OVA in the presence of compound 12 (orcein) results in less tPA activity. This indicates that orcein influenced misfolding of OVA and/or that orcein competes with tPA binding. At 160-fold dilution, compound 8 (haematein) induces further stimulation of tPA by OVA, a phenomenon that is more pronounced at 320-fold dilution. At 320-fold dilution also OVA heated in the presence of compound 10 (ellagic acid hydrate)

is a stimulator of tPA activity. These results further point to an interaction of the compounds with misfolded protein.

Figure 22:
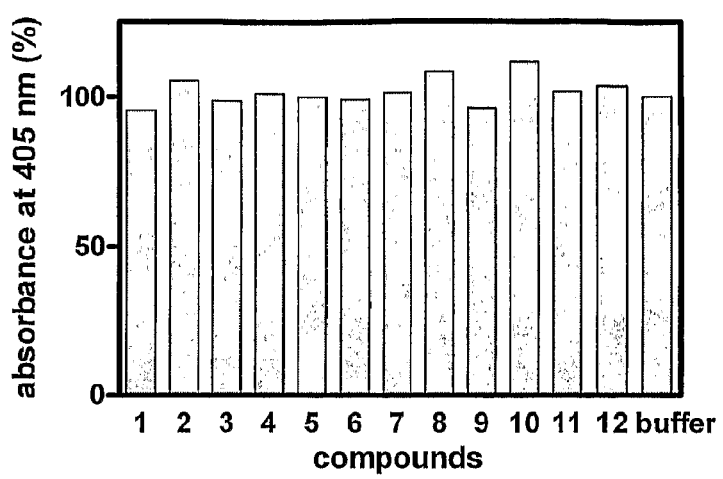
FIG. 22: Yellow color of plasmin-converted substrate PNAPEP1751 is not influenced by small compounds that interact with misfolded proteins. To test whether the twelve selected compounds (see Table 9) interfere with the absorbance readings at 405 nm in tPA and tPA/plasminogen chromogenic substrate conversion assays, absorbance was read at 405 nm of control solution with converted substrate PNAP1751, and of converted substrate with added compound at 80-fold or 160-fold dilution (1 mg/ml pre-diluted compound stocks).

To exclude any effect of a compound in a chromogenic assay on the absorbance signals read at 405 nm of the yellow converted substrates, diluted small compounds were added to yellow solutions of preformed converted substrate PNAPEP1751 (FIG. 22). An end-point absorbance reading at 405 nm revealed that none of the twelve compounds (Table 7) inhibits or increases signals, as compared to the buffer control. Therefore, any compound-mediated inhibition or acceleration of substrate conversion is not due to interactions of compounds with the substrate.

Next, influence of the small compounds on the capacity of ovalbumin to induce plasmin formation after heating of 1 mg/ml ovalbumin in PBS or in the presence of the twelve compounds at 1 mg/ml, was assessed. OVA concentration was 25 µg/ml, compound concentration was 25 µg/ml, DMSO concentration was 0.025%, in the activation assay. See FIG. 21. With the assay conditions tested, compounds 2 (thaliporphine), 3 (ammophedrine), 4 isoboldine, compound 7 (no name) and 11 (corynanthine) do not influence plasmin activity in the presence of OVA. Compounds 1 (dehydroglaucine derivative) and 12 (orcein) inhibit plasmin generation to some extent. Compounds 5 (no name), 6 (no name), 8 (haematein) and 10 (ellagic acid hydrate) strongly inhibit plasmin formation. This illustrates an interaction between misfolded OVA and the compounds. Either during heat-denaturation of OVA the compounds somehow prevent or shield misfolding of OVA, and/or in the tPA/plasminogen activation assay the compounds prevent tPA from interaction with misfolded OVA. Finally, compound 9 (DXS500k) strongly enhances tPA/plasminogen activation, illustrating an interaction between misfolded protein and DXS500k.

To obtain more detailed insight into the mechanism of binding to misfolded proteins, the influence of the twelve compounds on tPA/plasminogen activating properties of preformed misfolded OVA was analyzed. From FIG. 23 it can be clearly deduced that 8. haematein, 10. ellagic acid hydrate and 12. orcein are potent inhibitors of misfolded OVA-triggered plasmin generation. Compound 6. (no name) gave some delay of generation of maximum plasmin activity. Compound 9. DXS500k is also in this experimental set-up a potent activator of the tPA/plasminogen system. From these observations it is concluded that compounds 6, 8, 10 and 12 interact with misfolded OVA in a way that tPA binding/activation is influenced, thereby preventing efficient plasmin generation. The DXS500k is a potent activator of the system. This compound is well-known for its factor XII activating properties, although it is disclosed here that the presence of a defined amount of misfolded protein is required (see, FIG. 16).

Figure 21:
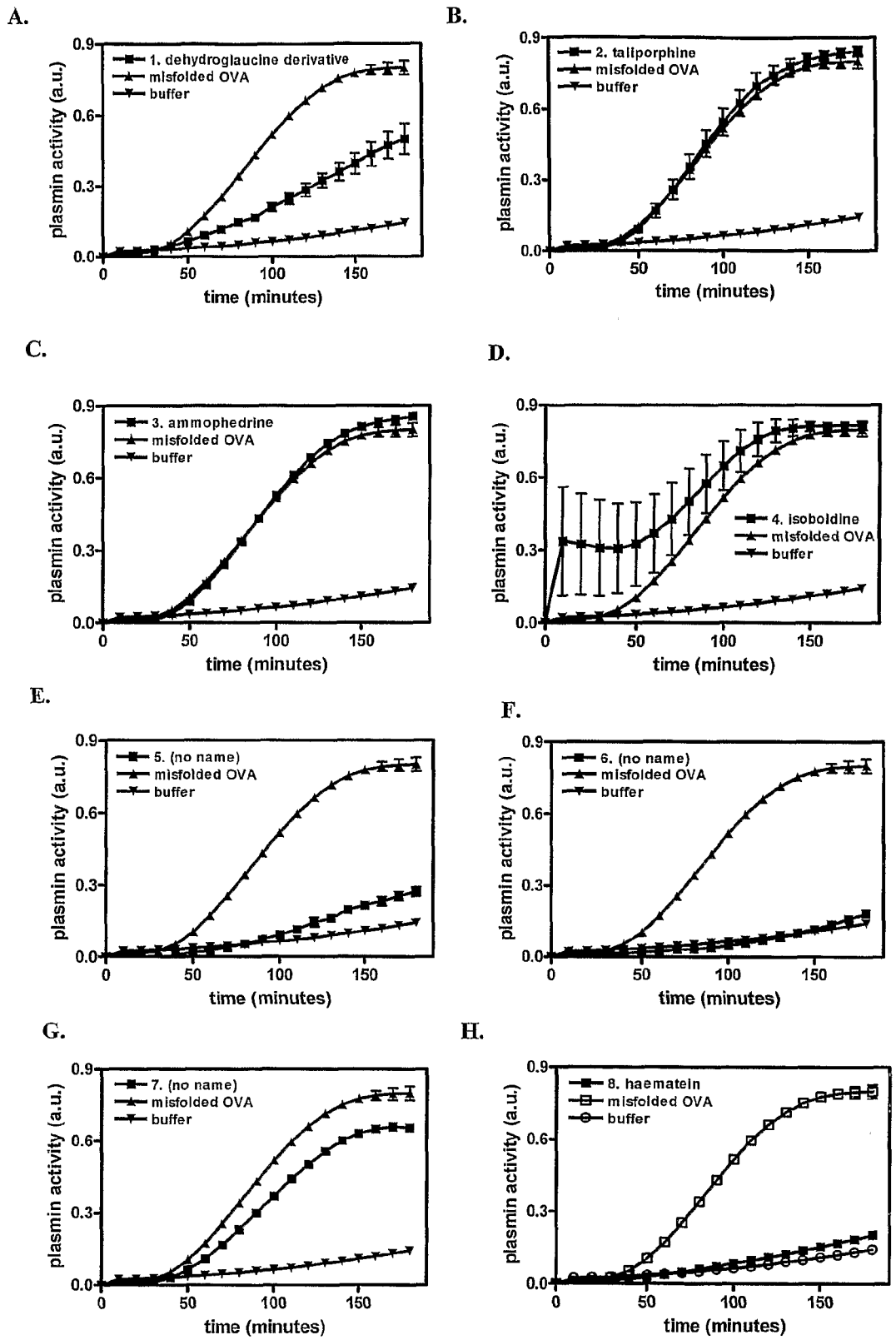
FIG. 21: Influence of ovalbumin heated in the presence of small compounds, on formation of plasmin. Plasmin substrate PNAPEP1751 conversion was followed in time with misfolded ovalbumin ("misfolded OVA") or with heated mixtures of ovalbumin and the indicated small compounds (indicated with the compound number and name, see Table 9).
Figure 23:
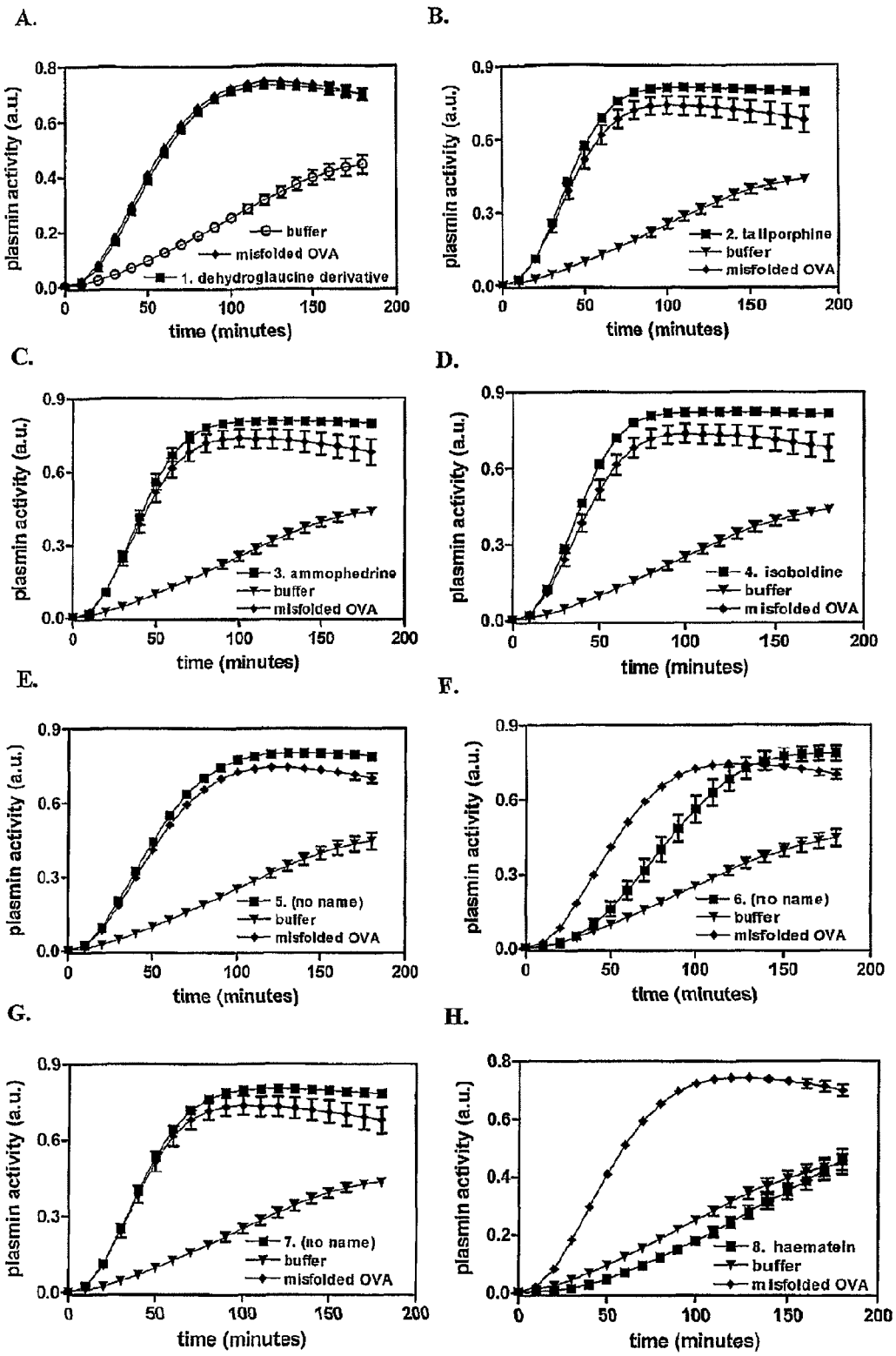
FIG. 23: Influence of misfolded protein-interacting small compounds on tPA/plasminogen activation by pre-misfolded ovalbumin. To test the influence of the indicated twelve compounds (see Table 9) at 80,000-fold (compound 2, 3, 4, 7, 11, 12) or 160,000-fold (compound 1, 5, 6, 8, 9, 10) dilution on potentiation of tPA/plasminogen activity by pre-formed misfolded ovalbumin (OVA), plasmin activity was assayed in a chromogenic assay. Compounds were included in the assay, or control buffer (80-fold or 160-fold diluted PBS/1% DMSO, compound buffer). In the figures, the compound number and name indicate assays with misfolded ovalbumin and the compound.
Figure 23:
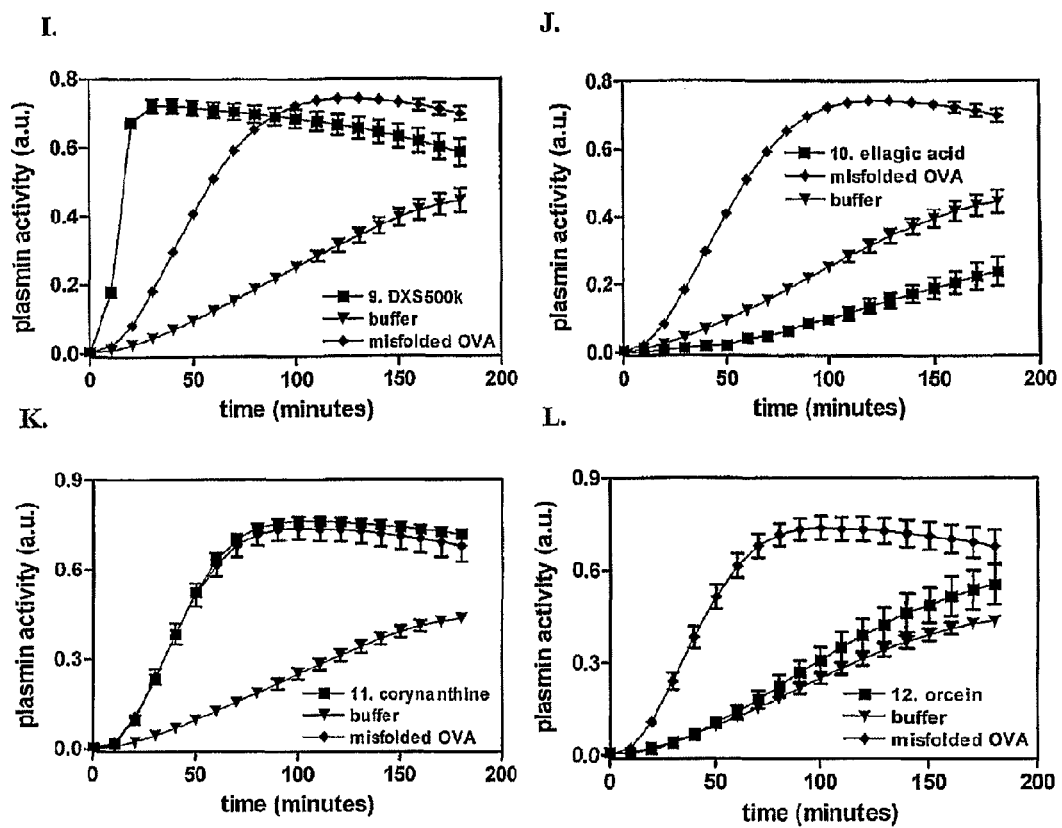

When compounds 3. ammophedrine HBr, 8. haematein and 10. ellagic acid hydrate are considered with respect to tPA activation and tPA/plasminogen activation, the following observations are striking. All three compounds induce increased tPA activity when combined with ovalbumin before heat-denaturation (FIG. 20). However, when ovalbumin that was misfolded first and then exposed to compounds 3, 8 and 10, or that was heated in the presence of these compounds, is included in the tPA/plasminogen activation assay, no stimulatory effect is seen (FIGS. 21 and 23). Actually, the contrary is seen: compound 3 does not exert any additional effect to the stimulating effect of ovalbumin, and compound 8 and 10 fully abolish plasmin activity. This discrepancy between increased tPA activating properties of the compounds combined with ovalbumin and inhibitory effects on ovalbumin mediated tPA/plasminogen activation points to an inhibitory role of the compounds on tPA-mediated plasmin generation from plasminogen, upon interaction with the tPA-activating misfolded protein. Apparently, the serine protease domain of tPA is not fully blocked when chromogenic substrate conversion is considered, but subsequent plasmin generation is effectively inhibited. These observations further strengthen the insight that misfolded protein specific blockers of tPA/plasmin activity are identified with the screening method.

Transmission Electron Microscopy Imaging with Ovalbumin Heated Together with Compounds Several of the twelve compounds that interact with misfolded protein (Table 7) influence tPA activity and/or tPA/plasminogen activation and/or interaction of Thioflavin T with misfolded protein (see above). Therefore, we wondered whether heating of ovalbumin in the presence of either of the compounds would result in less misfolded ovalbumin or a differently misfolded ovalbumin. For this purpose, the 1 mg/ml ovalbumin, either heated in the presence of the individual twelve small compounds, or in PBS control buffer, was subjected to TEM analyses (summarized in Table 10). Especially compounds 3. ammophedrine HBr, 8. haematein and 10. ellagic acid hydrate alter the macroscopic appearance of OVA. Unlike the appearance of ovalbumin control as many large aggregates in a background of small aggregates, with 3. ammophedrine only small aggregates are formed. With 8. haematein no large OVA aggregates are seen and the density of smaller aggregates is less than in control misfolded OVA. With 10. ellagic acid hydrate no (amorphous) aggregates are visible. However, clusters of needle-like structures are seen instead.

Based on the aforementioned data, it is concluded that IgIV, BiP and the eleven compounds selected from the set of small compounds are all newly identified molecules that interact with one or several different amyloid-like misfolded proteins. In Table 9, all data gathered with the eleven small compounds is summarized. From FIG. 10 a striking similarity between 2. thaliporphine and 4. isoboldine is recognized. This is indicative of a core chemical structure with affinity for a common structural aspect in the amyloid-like misfolded proteins tested, i.e., heat-denatured ovalbumin, glycated hemoglobin and amyloid-β. Further refinement using a specific library comprising compounds all related to these two identified compounds 2. and 4. provides lead compounds with improved characteristics with respect to binding to amyloid-like protein conformation or to protein conformation induced by the occurrence of amyloid-like conformation. More in general, further screening of compound libraries focused on any of the eleven identified compounds will reveal compounds related to the initially found compounds, with most likely even better binding characteristics. When all isoboldine/thaliporphine-related (aporphine) alkanoid compounds with the same core structure in our set of small compounds are considered (see Table 12), it is clear that the mode of influence on the interaction of tPA with misfolded protein is fully dependent on the atoms present at the periphery of the core chemical structure. Therefore, a further search within this family of alkanoids provides new lead drug compounds with interesting pharmacophore utility in medicine concerning appropriate therapy against problems related to the amyloid-like misfolded proteins. Interestingly, aporphine alkanoid boldine has already been mentioned with respect to its potential beneficial effect in the misfolding disease Parkinson's.

The applied screening methods showed that individual compounds can be identified from a compound library that have not yet been known for their ability to influence misfolded protein biology. The method is based on screening for compounds that influence the interaction between tPA and amyloid-like misfolded proteins. So, these results demonstrate a method for selecting a compound capable of binding to a cross-β structure or in general to amyloid-like misfolded protein conformation in a protein, comprising: contacting the compound with a first protein comprising amyloid-like conformation and allowing the compound and the protein to interact; determining whether the compound at least in part binds to the amyloid-like conformation; selecting the compound that at least in part binds to the amyloid-like misfolded protein. Within this method, the conformation recognized by the compound is either the amyloid-like conformation itself, or a conformation induced by the amyloid-like conformation, c.q. the cross-beta structure. Furthermore, our results show that the screening method is applicable for use with small compound libraries as well as with recombinant proteins and antibodies. With the screening technology chaperone BiP and human IgIV were identified as molecules with affinity for amyloid-like misfolded protein. Our selection methods were based on immobilized misfolded proteins as well as on misfolded proteins in solution. Thioflavin T and tPA binding experiments, and tPA and tPA/plasminogen activation assays provide tools for the different approaches with respect to the presentation of the misfolded protein, i.e., soluble versus immobilized on a carrier.

The robustness of this method is shown by the selection of ellagic acid hydrate from the set of small compounds. This compound is already known for its ability to stimulate factor XII, a serine protease that is activated by amyloid-like misfolded protein. It is furthermore clearly seen that individual compounds have specific abilities with respect to the various parameters related to tested protein misfolding approaches, related to misfolding and related to the identity of the target misfolded protein. This illustrates the usefulness of the screening method to identify lead compounds that either interact with any amyloid-like misfolded protein in general, irrespective of the underlying amino-acid sequence and/or length of the polypeptide, or interact more specifically to one or to a small range of misfolded molecules, and not to other misfolded proteins. This latter aspect is for instance important when targeting disease related misfolded proteins, without the necessity to interfere with normal functioning of the Cross-beta Pathway for clearance of obsolete proteins in general. In this way, pathological protein misfolding can be specifically targeted without interfering with physiological processes related to misfolded proteins.

When immobilized on a suitable carrier, compounds 1, 2, 4, 6, 9 and 10 (Table 7) are able to bind misfolded protein from solution. This result provides an example of a method for at least partly removing from a solution an amyloid-like misfolded protein comprising contacting a compound capable of binding to misfolded protein and/or a compound capable of binding to a protein conformation induced by misfolding in a protein, and removing the resulting complex from the solution.

For further validation of our screening method a first non-complete internet search was performed for available information on the biology of the eleven lead compounds that are selected from the set of small compounds based on their influence on interaction of tPA with amyloid-like disease-related misfolded proteins. Search key-words were the compound name, when known, and one or more of the key-words "coagulation," "amyloid," "aggregation," "fibril," "misfolding," "cell culture viability," "thrombosis," "NF-kappaB," "tPA," "factor XII," "Alzheimer," "amyloidosis," "protocol," "method," "review." The search was completed Spring 2006. A brief summary is given in Table 11.

In conclusion, the screening of the set of small compounds for lead compounds that influence binding of tPA to immobilized amyloid-like proteins has revealed target compounds that interact in various ways on activities of the misfolded proteins used for screening, as observed in the outlined series of in vitro assays. In addition, we identified chaperone BiP and human IgIV as new proteins with affinity and specificity for amyloid-like misfolded proteins.

TABLE 4

Small compound library used for screening for misfolded protein/misfolded protein binding protein - binding properties

| Compound # + name (if known) | Compound # + name (if known) | Compound # + name (if known) |
| --- | --- | --- |
| 1 | 2 | 3 |
| 4 | 5 | 6 |
| 7 | 8 Bucharaine | 9 |
| 10 | 11 | 12 |
| 13 Cytisine | 14 | 15 |
| 16 | 17 | 18 |
| 19 | 20 | 21 |
| 22 | 23 Anabasine | 24 Lupinine |
| 25 Podocarpic acid | 26 | 27 |
| 28 | 29 | 30 Harmalinehydrochloride dihydrate |
| 31 Papaverine | 32 | 33 |
| 34 Salsolidine | 35 | 36 |
| 37 | 38 | 39 |
| 40 | 41 | 42 |
| 43 | 44 | 45 |
| 46 | 47 | 48 |
| 49 | 50 | 51 |
| 52 | 53 | 54 |
| 55 | 56 kunurenic acid | 57 Protopine |
| 58 | 59 | 60 Dehydroglaucine |
| 61 Aconitine, 95% | 62 Pimaric acid | 63 Emodin |
| 64 | 65 Curcumine [458-37-7] (1,7-bis(4-hydroxy-3-methoxyphenyl)-1,6-heptadiene-3,5-dione) | 66 (S,R)-Noscapine |

TABLE 4-continued

Small compound library used for screening for misfolded protein/misfolded protein binding protein - binding properties

| Compound # + name (if known) | Compound # + name (if known) | Compound # + name (if known) |
| --- | --- | --- |
| 67 | 68 | 69 |
| 70 (−)Galanthamine | 71 | 72 |
| 73 | 74 | 75 |
| 76 | 77 | 78 |
| 79 | 80 | 81 |
| 82 | 83 | 84 |
| 85 | 86 | 87 |
| 88 | 89 | 90 |
| 91 | 92 | 93 |
| 94 | 95 | 96 (±)-Abscisic acid |
| 97 | 98 | 99 |
| 100 | 101 | 102 |
| 103 | 104 | 105 |
| 106 | 107 Dihydroergocristine mesylate | 108 Dihydroergotamine mesylate |
| 109 Metergoline phenylmethyl ester | 110 Galanthamine hydrobromide | 111 Rauwolscine hydrochloride |
| 112 Etoposide | 113 Colchicine | 114 |
| 115 | 116 | 117 Ellagic acid hydrate |
| 118 all-trans-Retinoic acid | 119 L-Carnosine | 120 Kinetin-9-riboside |
| 121 Vitamin D2 | 122 | 123 |
| 124 Ajmaline | 125 | 126 corynanthine |
| 127 (−)-Catinine | 128 | 129 gimkolide B |
| 130 karakoline from ranunculaceae family | 131 Noscapine hydrochloride hydrate (Narcotine) | 132 Oleanolic acid |
| 133 | 134 Phloretin | 135 |
| 136 | 137 | 138 |
| 139 | 140 dihydrofolic acid | 141 |
| 142 | 143 Fusaric acid from Gibberella fujikuroi | 144 |
| 145 | 146 | 147 |
| 148 | 149 | 150 DL-kynurenine sulfate salt, DL-2-Amino-4-(2-aminophenyl)-4-oxobutanoic acid |
| 151 | 152 Hematein | 153 Embelin [550-24-3] (2,5-Dihydroxy-3-undecyl-p-benzoquinone) |
| 154 Colchiceine | 155 Retinol, synthetic, 95.% | 156 |
| 157 | 158 Harmol | 159 |
| 160 | 161 | 162 |
| 163 | 164 Hesperidin, 80% | 165 (+/−)-Jasmonic acid |
| 166 Parthenolide | 167 Psoralen | 168 Resveratrol, 99% |
| 169 Strychnine | 170 Spectinomycin | 171 Caryophyllene oxide, 99% |
| 172 Monocrotaline | 173 5-Methoxypsoralen, 99% | 174 Melatonin |
| 175 Rotenone | 176 Kinetin, 98% | 177 Asiatic acis |
| 178 Norcantharidin | 179 Cinchonamine | 180 (−)-Eseroline, Fumarate salt |
| 181 Cycloheximide | 182 Caffeine | 183 Caffeic acid |
| 184 Prazosin hydrochloride | 185 Rifampicin | 186 Dihydrocapsacin |
| 187 Pergolide mesylate | 188 Lysergol | 189 (+)-Bicuculline |
| 190 (+)-Usnic acid from Usnea dasypoga | 191 alpha-Ergocryptine | 192 Andrographolide |
| 193 Ergocornine | 194 Ergocristine | 195 |
| 196 | 197 Orcein | 198 Thermopsine |
| 199 | 200 | 201 Thaliporphine, thalicmidine |
| 202 Isoboldine | 203 Bracteoline | 204 7-Oxoglaucine |
| 205 Seneciphylline | 206 Cryptopine | 207 N-methylcorydaldine |
| 208 Lagochiline | 209 dehydroglaucine derivative | 210 dehydroglaucine derivative |
| 211 berberine derivative | 212 berberine derivative | 213 dehydroglaucine derivative |
| 214 dehydroglaucine derivative | 215 dehydroglaucine derivative | 216 Matrine |
| 217 Ammophedrine HBr | 218 Otosenine | 219 Leontiformine HBr |
| 220 GOSSYPOL from cotton seeds | 221 L-abrine | 222 Sumaresinolic acid [559-64-8] (3b-6b-Dihydroxy olean-12-en-28-oice acid) |
| 223 Conessine [546-06-5] | 224 verapamil HCl | 225 (S)-(+)-ketoprofen |
| 226 Corynanthine hydrochloride | 227 Spectinomycin dihydrochloride pentahydrate | 228 Mevinolin from Aspergillus sp., minimum 98% |
| 229 Podophyllotoxin | | |

TABLE 6

Small compounds that influence the binding of tPA to immobilized Hb-AGE, when tPA and the compounds are mixed

| Inhibitors of tPA binding to Hb-AGE, when co-incubated with tPA (binding < 50% compared to buffer) | | | Stimulators of tPA binding to Hb-AGE, when co-incubated with tPA (binding > 100% compared to buffer) | |
|---|---|---|---|---|
| 4 | 74 | 164 | 51 | 152 |
| 15 | 78 | 166 | 68 | 157 |
| 18 | 80 | 167 | 69 | 171 |
| 19 | 92 | 169 | 72 | 187 |
| 20 | 99 | 172 | 79 | 199 |
| 23 | 101 | 173 | 84 | 202 |
| 24 | 119 | 177 | 85 | 205 |
| 26 | 126 | 179 | 96 | 211 |
| 32 | 127 | 197 | 100 | 212 |
| 34 | 130 | 198 | 117 | 220 |
| 36 | 140 | 201 | 134 | 225 |
| 43 | 146 | 208 | 150 | |
| 49 | 147 | 216 | | |
| 50 | 153 | 217 | | |
| 63 | 160 | 222 | | |
| 70 | 163 | 223 | | |

Numbers refer to compound numbers as listed in Table 4 and 5.

TABLE 7

Selected small compounds and DXS500k, that interact with misfolded proteins

| # | # according to Table 4, 5 | compound |
|---|---|---|
| 1 | 214 | Dehydroglaucine derivative |
| 2 | 201 | Thaliporphine, thalicmidine |
| 3 | 217 | Ammophedrine HBr |
| 4 | 202 | isoboldine |
| 5 | 51 | Compound 5 (no name) |
| 6 | 19 | Compound 6 (no name) |
| 7 | 15 | Compound 7 (no name) |
| 8 | 152 | haematein |
| 9 | — | DXS500k |
| 10 | 117 | ellagic acid hydrate |
| 11 | 126 | corynanthine |
| 12 | 197 | orcein |

Note:
DXS500k was included as a positive control in subsequent assays based on its known ability to bind to misfolded protein in solution, when immobilized, and based on its ability to denature proteins, which provides Thioflavin T binding sites and factor XII activating properties in the misfolded protein.

TABLE 8

Extraction with small compounds of misfolded protein ligands, glycated haemoglobin, and amyloid-β from solution

| # | Immobilized small compound | ELISA plate type | Coat concentration (μg/ml) | Misfolded protein ligand | Ligand concentration (μg/ml) | Signal (a.u.)[‡] |
|---|---|---|---|---|---|---|
| 1 | Dehydroglaucine derivative | Greiner Microlon | 100 | Aβ | 100 | 0.14 |
| 2 | Thaliporphine, thalicmidine | Nunc Maxisorp | 100 | Hb-AGE | 0.1 | 0.55 |
| 4 | isoboldine | Nunc amino Immobilizer | 1 | Hb-AGE | 10 | 0.20 |
| 4 | isoboldine | Nunc Maxisorp | 100 | Hb-AGE | 1 | 0.46 |
| 4 | isoboldine | Nunc amino Immobilizer | 1 | Aβ | 100 | 0.08 |
| 4 | isoboldine | Nunc Maxisorp | 100 | Aβ | 100 | 0.11 |
| 6 | Compound 6 (no name) | Nunc amino Immobilizer | 100 | Hb-AGE | 1 | 0.42 |
| 6 | Compound 6 (no name) | Nunc Maxisorp | 100 | Hb-AGE | 10 | 0.16 |
| 6 | Compound 6 (no name) | Nunc amino Immobilizer | 100 | Aβ | 10 | 0.03 |
| 6 | Compound 6 (no name) | Nunc amino Immobilizer | 100 | Aβ | 100 | 0.04 |
| 6 | Compound 6 (no name) | Nunc Maxisorp | 100 | Aβ | 100 | 0.08 |
| 9 | DXS500k | Nunc amino Immobilizer | 10 | Hb-AGE | 1 | 0.05 |
| 9 | DXS500k | Greiner Microlon | 100 | Hb-AGE | 10 | 0.13 |
| 10 | ellagic acid hydrate | Nunc Maxisorp | 100 | Hb-AGE | 10 | 0.15 |
| 10 | ellagic acid hydrate | Nunc Maxisorp | 100 | Aβ | 100 | 0.054 |
| 10 | ellagic acid hydrate | Greiner Microlon | 100 | Hb-AGE | 10 | 0.13 |

[‡]Background signals of 0 μg/ml misfolded protein ligand are subtracted.

Note:
immobilized compounds 3, 5, 7, 8, 11, 12 did not consistently extract misfolded proteins from solution and are therefore not listed. See Table 9 for compound names and numbers.

TABLE 9

Summary of observed activities of small compounds towards misfolded protein

| # | compound | Activity |
|---|---|---|
| 1 | Dehydroglaucine derivative | a. Inhibition of Thioflavin T fluorescence with misfolded OVA<br>b. Capture of misfolded protein from solution<br>c. Inhibition of tPA/plasminogen activation by OVA pre-heated in the presence of compound<br>d. Stimulated tPA binding to immobilized misfolded protein (misfolded OVA) |
| 2 | Thaliporphine, thalicmidine | a. Inhibition of Thioflavin T fluorescence with misfolded OVA<br>b. Capture of misfolded protein from solution<br>c. Stimulated tPA binding to immobilized misfolded protein (Hb-AGE) |
| 3 | Ammophedrine HBr | a. less OVA aggregates after heating in the presence of the compound, on TEM image<br>b. Inhibited tPA binding to immobilized misfolded protein (Hb-AGE, misfolded OVA) |
| 4 | isoboldine | a. Capture of misfolded protein from solution<br>b. Inhibition on Thioflavin T fluorescence with misfolded OVA<br>c. Stimulated tPA binding to immobilized misfolded protein (Aβ, Hb-AGE, misfolded OVA) |
| 5 | Compound 5 (no name) | a. Inhibition of tPA/plasminogen activation by OVA pre-heated in the presence of compound<br>b. Stimulated tPA binding to immobilized misfolded protein (misfolded OVA) |
| 6 | Compound 6 (no name) | a. Capture of misfolded protein from solution<br>b. Inhibition on Thioflavin T fluorescence with misfolded OVA<br>c. Inhibition of tPA/plasminogen activation by OVA pre-heated in the presence of compound<br>d. Stimulated tPA binding to immobilized misfolded protein (Hb-AGE, misfolded OVA)<br>e. Delayed tPA/plasminogen activation by misfolded OVA<br>f. Inhibited tPA binding to immobilized misfolded protein (misfolded OVA). Note: at a different concentration than in d. |
| 7 | Compound 7 (no name) | a. Inhibition on Thioflavin T fluorescence with misfolded OVA<br>b. Inhibited tPA binding to immobilized misfolded protein (Aβ) |
| 8 | haematein | a. less OVA aggregates after heating in the presence of the compound, on TEM image<br>b. Inhibition on Thioflavin T fluorescence with misfolded OVA<br>c. Inhibition of Aβ-induced platelet aggregation<br>d. Potentiation of tPA protease activity<br>e. Inhibition of tPA/plasminogen activation by OVA pre-heated in the presence of compound<br>f. Stimulated tPA binding to immobilized misfolded protein (Aβ, misfolded OVA)<br>g. Inhibited tPA binding to immobilized misfolded protein (Hb-AGE, misfolded OVA) Note: at a different concentration than in f.<br>h. Full block of tPA/plasminogen activation by misfolded OVA |
| 9 | DXS500k | a. Capture of misfolded protein from solution<br>b. Activation of factor XII<br>c. Potentiation of tPA/plasminogen activation by OVA pre-heated in the presence of compound<br>d. Stimulated tPA binding to immobilized misfolded protein (Aβ)<br>e. Potentiation of tPA/plasminogen activation by misfolded OVA |
| 10 | ellagic acid hydrate | a. less OVA aggregates after heating in the presence of the compound, on TEM image (needles instead of amorphous aggregates)<br>b. Capture of misfolded protein from solution<br>c. Activation of factor XII<br>d. Inhibition on Thioflavin T fluorescence with misfolded OVA<br>e. Inhibition of formation of Thioflavin T binding sites in heated OVA<br>f. Stimulation of platelet aggregation<br>g. Potentiation of tPA protease activity<br>h. Inhibition of tPA/plasminogen activation by OVA pre-heated in the presence of compound<br>i. Stimulated tPA binding to immobilized misfolded protein (Hb-AGE, Aβ, misfolded OVA)<br>j. Full block of tPA/plasminogen activation by misfolded OVA |
| 11 | corynanthine | a. Stimulated tPA binding to immobilized misfolded protein (misfolded OVA) |
| 12 | orcein | a. Inhibition on Thioflavin T fluorescence with misfolded OVA<br>b. Inhibition of tPA protease activity<br>c. Inhibition of tPA/plasminogen activation by OVA pre-heated in the presence of compound |

TABLE 9-continued

Summary of observed activities of small compounds towards misfolded protein

| # | compound | Activity |
|---|---|---|
| | | d. Stimulated tPA binding to immobilized misfolded protein (misfolded OVA) |
| | | e. Almost fully abolished activation of tPA/plasminogen by misfolded OVA |

Note:
DXS500k was included as a positive control in subsequent assays based on its known ability to bind to misfolded protein in solution, when immobilized, and based on its ability to denature proteins, which provides Thioflavin T binding sites and factor XII activating properties in the misfolded protein.

TABLE 10

Transmission electron microscopy imaging results with heated mixtures of ovalbumin + small compounds

| # | compound | |
|---|---|---|
| 0 | Control Misfolded OVA (1 mg/ml) with DMSO (1% v/v) | Aggregates are noticeable already on 1200x magnification. High incidence of aggregates. ~20 large amorphous aggregates per mesh with background of smaller amorphous aggregates. |
| 1 | Dehydroglaucine derivative | Smaller but more dense aggregates than in Control |
| 2 | Thaliporphine | Spherical aggregates with background of smaller amorphous aggregates like Control. |
| 3 | Ammophedrine HBr | Only small amorphous aggregates like Control background. |
| 4 | Isoboldine | Larger and more dense aggregates than control. Small dense aggregates in background. Shape of aggregates is similar to Control, but more dense. |
| 5 | Compound 5 (no name) | Very large aggregates shaped like those in Control but more dense. No aggregates are observed in the background. |
| 6 | Compound 6 (no name) | Background as in Control, but less aggregated. Also dense spherical aggregates. |
| 7 | Compound 7 (no name) | Similar to Control Misfolded OVA. |
| 8 | Haematein | No large aggregates. Small aggregates at a lower density than in Control. |
| 9 | DXS500k | Small aggregates similar to Control Misfolded OVA. |
| 10 | ellagic acid hydrate | Clusters of needle-like structures. No aggregates observed in background. |
| 11 | corynanthine | No protein visible |
| 12 | orcein | Dense amorphous aggregates, like in 4 and 5. |

TABLE 11

Use and activities with a link to amyloid-like misfolded proteins, of compounds that bind misfolded proteins

| # | compound | Use or activity in vitro/in vivo |
|---|---|---|
| 1 | Dehydroglaucine (derivative) | a. antimicrobial activity<br>b. decrease in the blood pressure after applying intravenously<br>c. bronchoconstrictor effect<br>d. inhibitory action on the central nervous system<br>e. inhibitory effect on lipopolysaccharide (LPS)-induced proliferation of splenocytes<br>f. protection of plants from invasion by micro-organisms |
| 2 | Thaliporphine, thalicmidine | a. increased survival rate of LPS-treated mice<br>b. attenuating endotoxin-induced circulatory failure and multiple organ injury<br>c. suppression of TNFα, NO. and $O^{2-}$ production.<br>d. stimulated splenocyte proliferation induced by LPS<br>e. may hold potential for the treatment of endotoxaemia<br>f. potent vasoconstrictor |
| 3 | Ammophedrine | {no information available} |
| 4 | isoboldine | a. potency to suppress LPS-induced proliferation in vitro<br>b. potent antiplasmodial activity<br>c. potential antiviral activity |
| 8 | haematein | a. inhibition of LPS/interferon-γ (IFNγ) induced NO production and iNOS expression in macrophages<br>b. inhibition of LPS/interferon-γ (IFNγ) induced NF-κB activation in macrophages |

TABLE 11-continued

Use and activities with a link to amyloid-like misfolded proteins, of compounds that bind misfolded proteins

| # | compound | Use or activity in vitro/in vivo |
|---|---|---|
| 10 | ellagic acid (hydrate) | a. anti-apoptotic activity<br>b. promote anti-inflammatory activities<br>c. activation of intrinsic pathway of coagulation by activation of factor XII<br>d. antibacterial properties<br>e. inhibition of the pathway that activates nuclear transcription factor κB,<br>f. cancer inhibitor which has the ability to cause apoptosis in cancer cells<br>g. antiviral properties<br>h. stabilize mast cells<br>i. promote anti-anaphylaxis activities<br>j. apoptosis for breast, pancreas, esophageal, skin, colon and prostate cancer cells |
| 11 | corynanthine | a. mediation of vasoconstriction |
| 12 | orcein | a. binding to elastin fibers<br>   I. Immunoreactivities of anti-vitronectin and anti-amyloid P component were found to co-localize with orcein-stainable fibers in adults<br>   II. acid-orcein-Giemsa stain: amyloid has a distinctive light-blue color<br>   III. stain of amyloid elastosis; amyloid deposits around elastic fibres<br>   IV. Elastic fibers are in the amyloid islands of primary systemic amyloidosis (familial amyloid polyneuropathy, macular amyloidosis)<br>b. no special affinity for elastin<br>c. staining mechanism is unclear<br>d. staining of negatively charged tissue components, including elastin<br>e. staining of 'viral inclusion bodies' inside host cells |

(Incomplete) Information found on the www by searching with combinations of key-word 'compound name' together with selections of key-words 'coagulation', 'amyloid', 'aggregation', 'fibril', 'misfolding', 'cell culture viability', 'thrombosis', 'NF-kappaB', 'tPA', 'factor XII', 'Alzheimer', 'amyloidosis', 'protocol', 'method', 'review'.

TABLE 12

Influence of isoboldine/thaliporphine-like alkaloid compounds on tPA binding when co-incubated or when first exposed to misfolded protein before binding of tPA

| compound | % tPA binding to Hb-AGE (co-incubation) | % tPA binding (after compound incubation) | compound | % tPA binding to Hb-AGE (co-incubated) | % tPA binding (after compound incubation) |
|---|---|---|---|---|---|
| Control (no compound) | 100 | HbAGE 100<br>Aβ 100<br>DOVA 100 | 201 thaliporphine | 30 | HbAGE 110<br>Aβ 400<br>DOVA 400 |
| 53 | 55 | | 202 isoboldine | 250 | HbAGE 250<br>Aβ 250<br>DOVA 420 |
| 71 | 50 | | 203 | 55 | Aβ 85<br>DOVA 105 |
| 84 | 135 | HbAGE 105 | 204 | 70 | Aβ 55<br>DOVA 80 |
| 85 | 195 | DOVA 135 | 210 | 80 | Aβ 30<br>DOVA 90 |

TABLE 12-continued

Influence of isoboldine/thaliporphine-like alkaloid compounds on tPA binding when co-incubated or when first exposed to misfolded protein before binding of tPA

| compound | % tPA binding to Hb-AGE (co-incubation) | % tPA binding (after compound incubation) | compound | % tPA binding to Hb-AGE (co-incubated) | % tPA binding (after compound incubation) |
|---|---|---|---|---|---|
| 138 | 50 | DOVA 65 | 213 | 60 | Aβ 210 DOVA 105 |

Core structure of isoboldine and thaliporphine/thalicmidine and the like aporphine alkaloid compounds, with R a variable chemical group.

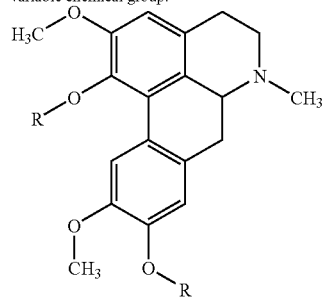

REFERENCE LIST

1. Bouma B., L. M. Kroon-Batenburg, Y. P. Wu et al. Glycation induces formation of amyloid cross-beta structure in albumin. *J. Biol. Chem.* 278, 41810-41819 (2003).
2. Townsend K. P. et al. CD40 signaling regulates innate and adaptive activation of microglia in response to amyloid beta-peptide. *Eur. J. Immunol.* 35, 901-910 (2005).
3. Subang R. et al. Phospholipid-bound beta 2-glycoprotein I induces the production of anti-phospholipid antibodies. *J. Autoimmun.* 15, 21-32 (2000).
4. Kranenburg O., B. Bouma, L. M. Kroon-Batenburg et al. Tissue-type plasminogen activator is a multiligand cross-beta structure receptor. *Curr. Biol.* 12, 1833-1839 (2002).
5. Gebbink M. F., D. Claessen, B. Bouma, L. Dijkhuizen and H. A. Wosten. Amyloids—a functional coat for microorganisms. *Nat. Rev. Microbiol.* 3, 333-341 (2005).
6. Schousboe I. Factor XIIa activation of plasminogen is enhanced by contact activating surfaces and Zn2+. *Blood Coagul. Fibrinolysis* 8, 97-104 (1997).
7. O'Nuallain B. and R. Wetzel. Conformational Abs recognizing a generic amyloid fibril epitope. *Proc. Natl. Acad. Sci. U.S.A.* 99, 1485-1490 (2002).
8. Kayed R. et al. Common structure of soluble amyloid oligomers implies common mechanism of pathogenesis. *Science* 300, 486-489 (2003).
9. Matzinger P. The danger model: a renewed sense of self. *Science* 296, 301-305 (2002).
10. Ashkar A. A. and K. L. Rosenthal. Toll-like receptor 9, CpG DNA and innate immunity. *Curr. Mol. Med.* 2, 545-556 (2002).
11. Sarvari M. et al. Inhibition of C1q-beta-amyloid binding protects hippocampal cells against complement mediated toxicity. *J. Neuroimmunol.* 137, 12-18 (2003).
12. Veerhuis R. et al. Activation of human microglia by fibrillar prion protein-related peptides is enhanced by amyloid-associated factors SAP and C1q. *Neurobiol. Dis.* 19, 273-282 (2005).
13. Bellotti V., P. Mangione and G. Merlini. Review: immunoglobulin light chain amyloidosis—the archetype of structural and pathogenic variability. *J. Struct. Biol.* 130, 280-289 (2000).
14. Buxbaum J. N. The systemic amyloidoses. *Curr. Opin. Rheumatol.* 16, 67-75 (2004).
15. de Laat B., R. H. Derksen, R. T. Urbanus, and P. G. de Groot. IgG antibodies that recognize epitope Gly40-Arg43 in domain I of {beta}2-glycoprotein I cause LAC and their presence correlates strongly with thrombosis. *Blood* (2004).
16. Horbach D. A., E. van Oort, R. C. Donders, R. H. Derksen, and P. G. de Groot. Lupus anticoagulant is the strongest risk factor for both venous and arterial thrombosis in patients with systemic lupus erythematosus. Comparison between different assays for the detection of antiphospholipid antibodies. *Thromb. Haemost.* 76, 916-924 (1996).
17. Horbach D. A., E. van Oort, M. J. Tempelman, R. H. Derksen, and P. G. de Groot. The prevalence of a non-phospholipid-binding form of beta2-glycoprotein I in human plasma-consequences for the development of anti-beta2-glycoprotein I antibodies. *Thromb. Haemost.* 80, 791-797 (1998).
18. de Laat H. B., R. H. Derksen, R. T. Urbanus, M. Roest, and P. G. de Groot. beta2-glycoprotein I-dependent lupus anticoagulant highly correlates with thrombosis in the antiphospholipid syndrome. *Blood* 104, 3598-3602 (2004).
19. Connor P. and B. J. Hunt. Cerebral haemostasis and antiphospholipid antibodies. *Lupus* 12, 929-934 (2003).
20. de Groot P. G., D. A. Horbach, and R. H. Derksen. Protein C and other cofactors involved in the binding of antiphospholipid antibodies: relation to the pathogenesis of thrombosis. *Lupus* 5, 488-493 (1996).
21. Matsuura E., Y. Igarashi, T. Yasuda, D. A. Triplett, and T. Koike. Anticardiolipin antibodies recognize beta 2-glycoprotein I structure altered by interacting with an oxygen modified solid phase surface. *J. Exp. Med.* 179, 457-462 (1994).

22. Levine J. S., R. Subang, J. S. Koh, and J. Rauch. Induction of anti-phospholipid autoantibodies by beta2-glycoprotein I bound to apoptotic thymocytes. *J. Autoimmun.* 11, 413-424 (1998).
23. Kuwana M. Beta2-glycoprotein I: antiphospholipid syndrome and T-cell reactivity. *Thromb. Res.* 114, 347-355 (2004).
24. Kuwana M. et al. Binding of beta 2-glycoprotein I to anionic phospholipids facilitates processing and presentation of a cryptic epitope that activates pathogenic autoreactive T cells. *Blood* 105, 1552-1557 (2005).
25. Matzinger P. An innate sense of danger. *Ann. N.Y. Acad. Sci.* 961:341-2, 341-342 (2002).
26. Bouma B. et al. Adhesion mechanism of human beta(2)-glycoprotein I to phospholipids based on its crystal structure. *EMBO J.* 18, 5166-5174 (1999).
27. Schielen H. P. Adams, M. Voskuilen, G. I. Tesser, and W. Nieuwenhuizen. The sequence A alpha-(154-159) of fibrinogen is capable of accelerating the t-PA catalysed activation of plasminogen. *Blood Coagul. Fibrinolysis* 2, 465-470 (1991).
28. Nelson R. et al. Structure of the cross-beta spine of amyloid-like fibrils. *Nature* 435, 773-778 (2005).
29. Kranenburg O., B. Bouma, Y. Y. Gent et al. Beta-amyloid (Abeta) causes detachment of N1E-115 neuroblastoma cells by acting as a scaffold for cell-associated plasminogen activation. *Mol. Cell. Neurosci.* 2005; 28:496-508.

The invention claimed is:

1. A method for selecting a compound able to bind directly to a cross-β structure induced epitope or binding site in a protein comprising a cross-β structure, the method comprising:

contacting said compound with a first protein comprising a cross-β structure, allowing said compound and said first protein to interact, determining with a competition assay with a molecule that binds or interacts with cross-β structure whether said compound binds to a cross-β structure induced conformation, selecting a compound that binds to a cross-β structure induced epitope or binding site, performing a second assay with the compound and a second protein comprising a cross-β structure, and selecting a compound that binds preferentially to the first protein in comparison to the second protein.

2. The method according to claim 1, wherein said compound is from a library, a recombinant protein library, a small compound library, or an antibody library.

3. The method according to claim 2, wherein the first protein is immobilized and/or labeled.

4. The method according to claim 3, wherein the selected compound able to bind directly to a cross-β structure induced epitope or binding site is a protein, antibody, small molecule, or antibody fragment.

5. The method according to claim 3, wherein the first protein is from a sample of body fluid, blood, or blood component.

6. The method according to claim 1, wherein the compound thus selected is a dehydroglaucine derivative, thaliporphine, isoboldine, bracteoline, or 7-oxoglaucine.

7. The method according to claim 1, wherein the compound enhances binding of the molecule to the cross-β structure in the competition assay.

8. The method according to claim 1, wherein the compound inhibits binding of the molecule to the cross-β structure in the competition assay.

* * * * *

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial sequence
<220> FEATURE:
<223> OTHER INFORMATION: Peptide FP13 from Homo Sapiens - fibrinogen
      alpha chain, amino acids 148-160
<220> FEATURE:
<221> NAME/KEY: MISC_FEATURE
<222> LOCATION: (10)..(10)
<223> OTHER INFORMATION: X can be:
      K for wildtype
      or mutations G or D

<400> SEQUENCE: 1

Lys Arg Leu Glu Val Asp Ile Asp Ile Xaa Ile Arg Ser
1               5                   10

<210> SEQ ID NO 2
<211> LENGTH: 13
<212> TYPE: PRT
<213> ORGANISM: Artificial sequence
<220> FEATURE:
<223> OTHER INFORMATION: Peptide FP13 from homo sapiens fibrinogen
      alpha chain amino acids 148-160 - mutation K to G at position 157
<220> FEATURE:
<221> NAME/KEY: MISC_FEATURE
<222> LOCATION: (10)..(10)
<223> OTHER INFORMATION: Substitution amino acid 157 - K to G

<400> SEQUENCE: 2

Lys Arg Leu Glu Val Asp Ile Asp Ile Gly Ile Arg Ser
1               5                   10

<210> SEQ ID NO 3
<211> LENGTH: 10
<212> TYPE: PRT
<213> ORGANISM: Artificial sequence
<220> FEATURE:
<223> OTHER INFORMATION: Peptide from homo sapiens fibrinogen alpha
      chain amino acids 148-157

<400> SEQUENCE: 3

Lys Arg Leu Glu Val Asp Ile Asp Ile Lys
1               5                   10

<210> SEQ ID NO 4
<211> LENGTH: 6
<212> TYPE: PRT
<213> ORGANISM: Artificial sequence
<220> FEATURE:
```

```
<223> OTHER INFORMATION: Peptide from homo sapiens fibrinogen alpha
      chain amino acids 154-159

<400> SEQUENCE: 4

Ile Asp Ile Lys Ile Arg
1               5

<210> SEQ ID NO 5
<211> LENGTH: 10
<212> TYPE: PRT
<213> ORGANISM: Artificial sequence
<220> FEATURE:
<223> OTHER INFORMATION: Linker peptide
<220> FEATURE:
<221> NAME/KEY: MISC_FEATURE
<223> OTHER INFORMATION: linker introduced in recombinantly produced
      protein

<400> SEQUENCE: 5

Lys Ser Lys Ser Lys Ser Met Met Ala Ala
1               5                   10

<210> SEQ ID NO 6
<211> LENGTH: 8
<212> TYPE: PRT
<213> ORGANISM: Artificial sequence
<220> FEATURE:
<223> OTHER INFORMATION: Sequence for tags for detection with
      antibodies specific for this sequence
<220> FEATURE:
<221> NAME/KEY: MISC_FEATURE
<223> OTHER INFORMATION: FLAG-tags are frequently used in
      recombinantly purified proteins for detection and purification
      purpose

<400> SEQUENCE: 6

Asp Tyr Lys Asp Asp Asp Asp Lys
1               5

<210> SEQ ID NO 7
<211> LENGTH: 6
<212> TYPE: PRT
<213> ORGANISM: Artificial sequence
<220> FEATURE:
<223> OTHER INFORMATION: 6 histidine residues tag for affinity
      purification of proteins
<220> FEATURE:
<221> NAME/KEY: MISC_FEATURE
<223> OTHER INFORMATION: Histidine tags comprising 6 amino acids are
      frequently used in recombinantly produced proteins for
      purification purpose

<400> SEQUENCE: 7

His His His His His His
1               5
```